United States Patent
Yedwab et al.

(10) Patent No.: US 10,614,919 B1
(45) Date of Patent: Apr. 7, 2020

(54) AUTOMATED MEDICAL DIAGNOSIS, RISK MANAGEMENT, AND DECISION SUPPORT SYSTEMS AND METHODS

(71) Applicant: NANTHEALTH, INC., Culver City, CA (US)

(72) Inventors: Erik H. Yedwab, Cream Ridge, NJ (US); William A. Flood, Landisville, PA (US)

(73) Assignee: NANTHEALTH, INC., Culver City, CA (US)

( * ) Notice: Subject to any disclaimer, the term of this patent is extended or adjusted under 35 U.S.C. 154(b) by 0 days.

(21) Appl. No.: 14/047,621

(22) Filed: Oct. 7, 2013

Related U.S. Application Data

(63) Continuation-in-part of application No. 12/632,426, filed on Dec. 7, 2009, now abandoned, and a continuation-in-part of application No. 12/271,315, filed on Nov. 14, 2008, now abandoned.

(60) Provisional application No. 61/003,062, filed on Nov. 14, 2007, provisional application No. 61/710,382, filed on Oct. 5, 2012.

(51) Int. Cl.
*G16H 50/20* (2018.01)

(52) U.S. Cl.
CPC .................. *G16H 50/20* (2018.01)

(58) Field of Classification Search
CPC .............. G06Q 50/22–24; G06Q 40/08; G06F 19/322–328; G16H 50/20
See application file for complete search history.

(56) References Cited

U.S. PATENT DOCUMENTS

| | | | |
|---|---|---|---|
| 6,047,259 A * | 4/2000 | Campbell et al. ............... 705/3 |
| 7,072,840 B1 | 7/2006 | Mayaud | |
| 7,630,788 B1 | 12/2009 | Reese | |
| 7,801,591 B1 | 9/2010 | Shusterman | |
| 8,032,394 B1 * | 10/2011 | Ghouri ............................. 705/2 |
| 2002/0019749 A1 * | 2/2002 | Becker ................. G06F 19/325 |
| | | | 705/2 |
| 2002/0091546 A1 * | 7/2002 | Christakis ............ G06F 19/322 |
| | | | 705/2 |
| 2002/0143579 A1 * | 10/2002 | Docherty ............. G06F 19/325 |
| | | | 705/2 |
| 2002/0147616 A1 | 10/2002 | Pollard et al. | |
| 2002/0184050 A1 | 12/2002 | Papageorge | |

(Continued)

*Primary Examiner* — Sheetal R Paulson
(74) *Attorney, Agent, or Firm* — Stetina Brunda Garred and Brucker

(57) ABSTRACT

In one aspect, the invention relates to method and systems for automating medical data processing and counseling. A method may include receiving a selection of a condition associated with a plurality of diagnosis possibilities for a patient. The method may further include displaying candidate treatment options based upon, at least in part, the condition associated with the plurality of diagnosis possibilities for the patient. The method may also include receiving a selection of a candidate treatment option from the candidate treatment options displayed and a regimen associated with the candidate treatment option selected. The method may additionally include determining a diagnosis for the patient based upon, at least in part, the condition associated with the plurality of diagnosis possibilities for the patient, the candidate treatment option, and the regimen. The diagnosis may be one of the plurality of diagnosis possibilities for the patient.

20 Claims, 44 Drawing Sheets

(56) References Cited

U.S. PATENT DOCUMENTS

| | | | |
|---|---|---|---|
| 2003/0195774 A1* | 10/2003 | Abbo ................................. | 705/3 |
| 2004/0117126 A1 | 6/2004 | Fetterman et al. | |
| 2004/0260155 A1 | 12/2004 | Ciarniello et al. | |
| 2006/0080139 A1 | 4/2006 | Mainzer | |
| 2006/0235280 A1 | 10/2006 | Vonk et al. | |
| 2007/0033073 A1* | 2/2007 | Tajaliawal ............. | G06Q 50/24 |
| | | | 705/3 |
| 2008/0103836 A1* | 5/2008 | Park ...................... | G06F 19/328 |
| | | | 705/4 |
| 2011/0282690 A1* | 11/2011 | Patel et al. ........................ | 705/3 |

* cited by examiner

Name and Demographics

First Name:
Middle Name:
Last Name:

Gender: ○ Male  ○ Female
Date of Birth:
SSN:

Contact Information

Home Phone:
Business Phone:
Mobil Phone:
Best Time to contact: Any ▼
Contact instructions:

Fax Number:
Email address:
Preferred Contact Method: Home Phone ▼

Primary Address

Street 1:
Street 2:
Zip Code:

City:
State: Select State ▼

FIG. 3A

| Your Account | ☐ Knowledge Base | 🎲 OncolQ System Management | | wcooper |
|---|---|---|---|---|
| Enrollment call 1 to: Rachel Rabbitt3 | | | | |
| Call Date: | 9/9/2009 | | | |
| Contact Made: | YES ▼ | | | |
| Gender: | ● Male  ○ Female | | | |
| DOB: | 3/11/1969 | | | |
| Cancer Type: | Select Cancer Type<br>Adrenal<br>Ampulla of Vader<br>Anal Canal | | | |

FIG. 3B

| Cancer Type: | Breast<br>Cervix<br>Colon<br>Esophagus |
|---|---|
| Cancer Path: | Select Pathology ▼ |
| Cancer Stage: | Select Pathology<br>Adenocarcinoma - Inflammatory Carcinoma |
| Date Diagnosed: | |
| Have you ever had, or will you have surgery? | |
| Have you ever had, or will you have chemo? | Unknown |
| Clinical trial? | Select Clinical Trail ▼ |

FIG. 3E surgery?
Have you ever had, or will you have chemo?

Yes, Past Known Date

Date

Select Frequency
- Select Frequency
- Daily
- Bi-weekly
- Weekly
- Every two weeks Clinical Trail?

...e of chemo drugs.
7 and 3 Daunorubicin and Cytarabine and GM-CSF for Elderly Patients with AML

FIG. 3F

Chemo Drugs?

Taxol
Taxotere
Temodar
Temozolamide

>>

Adriamycin, Cytoxan, Taxol

Clear

FIG. 3G

Have you ever had, or will you have xrt?

Select xrt
- Select xrt
- No
- Yes, Past Known Date
- Yes, Past Unknown Date
- Yes, Future Unknown Date
- Yes, Future Known Date
- Not yet determined

FIG. 3H

| | |
|---|---|
| Supportive Drugs? | Neulasta<br>Neumega<br>Neupogen<br>Ondansetron  >> <br>Aloxi, Neulasta.  Clear |

FIG. 3I

Create New Task:

| | |
|---|---|
| Select Patient: | Rabbit3, Rachel |
| Task Type: | Phone Call |
| Communication Type: | Patient |
| Communication Description: | Select Desc |
| | Select Desc |
| Task Due Date: | Discharge of patient |
| Task Priority: | Discuss applications for pharmaceutical patient assistance programs |
| Task Assigned to: | |

Submit

FIG. 4A

| | |
|---|---|
| Call Date: | 6/2/2008 |
| Call Initiation: | Outgoing |
| Phone Number of call: | 888- |
| Contact Made: | Yes |
| Name of Person spoke to: | |

Call Details:
☐ Review anticipated side effects of therapy
☐ Reinforce side effect management and self-care measures

FIG. 4B

ICD9  Select ICD9
Molecular Markers: Select ICD9
174.0 Malignant neoplasm of nipple and areola of female breast
174.1 Malignant neoplasm of central portion of female breast Metastasis:

FIG. 5D

Metastasis: Lung    Met Date: 8/8/08
Add metastasis
Bone    6/28/2008 12:00:00 AM    Remove
Lung    8/8/2008 12:00:00 AM    Remove
Add Above Diagnosis

FIG. 5E

```
Rachel Rabbitt3  (CAS-1092)
| Admin | Notes | Contacts | Status | Diagnosis | Treatment Plan | Prognosis | Savings | Reports |

No Treatment Plans Entered

[ Add New Treatment Plan ]
```

FIG. 6A

```
Add New Treatment Plan                                              [X]
Diagnosis:   [Select Diagnosis  ▼]   Treatment Goal: [Select Goal  ▼]
Study:       [Select Study      ▼]   Line of
                                     Treatment:      [Select Line  ▼]
Conclusion
Treatment Plan  [                    ]   Conclusion
Conclusion                               Reason:      [Select Reason ▼]
Compliance
Compliant with Policy:      [Select Compliance  ▼]
T.P. Consistent w/ E.B.M:   [Select Consistency ▼]
(M.O. Only)
Add Treatments:             [Select Treatment  ▼]  [>>]
Add Regimen:                [               ▼]    [>>]

No Regimens
[ Toggle Open/Close All ]
No Tx Options
                            [ Add Above Treatment Plan ]
```

Add New Treatment Plan

Diagnosis: [Breast ▼]   Treatment Goal: [Curative ▼]
Study: [Select Study ▼]   Line of Treatment: [Adjuvant ▼]

Conclusion

Treatment Plan Conclusion: [          ]   Conclusion Reason: [Select Reason ▼]

Compliance

Compliant with Policy: [Yes ▼]
T.P. Consistent w/ E.B.M. (M.O. Only): [Select Consistency ▼]
Add Treatments: [Select Treatment ▼]   [>>]
Add Regimen: [DD-AC-P ▼]   [>>]
No Regimens

[Toggle Open/Close All]   [Add Above Treatment Plan]
No Tx Options

FIG. 6G

Product Name

Welcome Dr. Smith

| Select Patient | Enter Diagnosis | Enter Treatment |

Select a Patient

Patient First Name: Jane
Patient Last Name: Public
Patient Zip Code: 92019
Patient Insurance ID: 123-45-6789

[Search]

Jane Public
Female
DOB: 7/21/1961

Address:

Insurance:
Group Number: 10043
Policy Number: 123-45-6789

[Continue>>]

Review Eligibility Information | Update Patient Demographics

Product Name

Welcome Dr. Smith

| Select Patient | Enter Diagnosis | Enter Treatment |

Patient: Jane L. Public
Diagnosis: Breast Cancer. Adenocarcinoma - Invasive Ductal Carcinoma - Stage IV
Treatment Plan:
The following regimens are compliant with the patient's plan language, and are considered to be Evidence Based Medicine based on the Diagnosis of:
Breast Cancer. Adenocarcinoma - Invasive Ductal Carcinoma - Stage IV In completing this wizard you will build an evidence based treatment for your patient and will receive an EBM "plan code" to submit with your claims for automatic payment.

Select EBM Treatment Plan:

(Select Treatment Plan)
Albumin-bound Paclitaxel (Abraxane) in Recurrent/Metastatic Breast Cancer
CAF in Recurrent/Metastatic Breast Cancer
Capecitabine in Recurrent/Metastatic Breast Cancer Select a different Treatment Plan:  [ Other ]

If the treatment you wish to prescribe is NOT in the EBM list above, you may enter another regimen. HOWEVER, please be advised that using the 'Other' button will not automatically result in an evi# code and your claims may be subject to the normal review process.

[ << Back ]   [ Continue >> ]

FIG. 9F

Product Name

Welcome Dr. Smith

| Select Patient | Enter Diagnosis | Enter Treatment |

Patient: Jane L. Public

Diagnosis: Breast Cancer: Adenocarcinoma - Invasive Ductal Carcinoma - Stage IV

Treatment Plan: Albumin-bound Paclitaxel (Abraxane) in Recurrent/Metastatic Breast Cancer You will now be walked through our EBM Wizard in which you will be asked a series of questions about the treatment plan you are prescribing. Any answer accepted WILL result in a plan code.

Albumin-bound Paclitaxel (Abraxane) Dosing
Select the Per Unit Dose: [ 260 ] [+] [−] $mg/m^2$ This regimen states Albumin-bound Paclitaxel (Abraxane) PUD must be between 234 and 286

[<< Back]  [Continue >>]

FIG. 9G

Product Name

Welcome Dr. Smith

| Select Patient | Enter Diagnosis | Enter Treatment |

Patient: Jane L. Public

Diagnosis: Breast Cancer, Adenocarcinoma - Invasive Ductal Carcinoma - Stage IV

Treatment Plan: Albumin-bound Paclitaxel (Abraxane) in Recurrent/Metastatic Breast Cancer You will now be walked through our EBM Wizard in which you will be asked a series of questions about the treatment plan you are prescribing. Any answer accepted WILL result in a plan code.

Albumin-bound Paclitaxel (Abraxane) Dosing
Select the per Unit Dose

[220] Invalid PUD Range!

[+] [−] mg/m²

This regimen states Albumin-bound Paclitaxel (Abraxane) PUD must be between 234 and 286

[<< Back] [Continue >>]

Product Name

Welcome Dr. Smith

| Select Patient | Enter Diagnosis | Enter Treatment |

Patient: Jane L. Public
Diagnosis: Breast Cancer: Adenocarcinoma - Invasive Ductal Carcinoma - Stage IV Treatment Plan: Albumin-bound Paclitaxel (Abraxane) in Recurrent/Metastatic Breast Cancer You will now be walked through our EBM Wizard in which you will be asked a series of questions about the treatment plan you are prescribing. Any answer accepted WILL result in a plan code.

Albumin-bound Paclitaxel (Abraxane) Dosing
Select the per Unit Dose  [260]  [+] [-] mg/m²  This regimen states Albumin-bound Paclitaxel (Abraxane) PUD must be between 234 and 286

[<< Back]   [Continue >>]

FIG. 9I

Product Name

Welcome Dr. Smith

| Select Patient | Enter Diagnosis | Enter Treatment |

Patient: Jane L. Public
Diagnosis: Breast Cancer Adenocarcinoma - Invasive Ductal Carcinoma - Stage IV Treatment Plan: Albumin-bound Paclitaxel (Abraxane) in Recurrent/Metastatic Breast Cancer Antiemetic Selection:
This regimen has a low emetogenicity, therefore an antiemetic is optional.

Select one of the Antiemetics (optional):

[ No Antiemetic  ▼ ]
      No Antiemetic
      Prochlorperazine - 10mg
      Metoclopramide - 10mg
      Dexamethasone/Decadron - 12mg

[ << Back ]    [ Continue >> ]

FIG. 9J

Select Patient | Enter Diagnosis | Enter Treatment

Patient: Jane L. Public
Diagnosis: Breast Cancer Adenocarcinoma - Invasive Ductal Carcinoma - Stage IV Treatment Plan: Albumin-bound Paclitaxel (Abraxane) in Recurrent/Metastatic Breast Cancer Other Supportive Selection:
This regimen has optional supportive drugs.

Select one of the other supportive drugs (optional):

No Other Supportives
Lorazepam/Ativan 0.5 mg
Diphenhydramine HCl/Benadryl - 50 mg
Cimetidine/Tagamet - 300 mg
Famotidine/Pepcid - 20 mg Product Name Welcome Dr. Smith

FIG. 9K

| Select Patient | Enter Diagnosis | Enter Treatment |

Patient: Jane L. Public
Diagnosis: Breast Cancer: Adenocarcinoma - Invasive Ductal Carcinoma - Stage IV Treatment Plan: Albumin-bound Paclitaxel (Abraxane) in Recurrent/Metastatic Breast Cancer Review: In accordance with the regimens article, and upon your completion of the questions, the system has generated the following evidence based treatment plan. Please review all treatments and make sure these are the treatments you wish to administer to your patient.

Cycle: cycle 1 of UNTIL DISEASE PROGRESSION, Cycle length: 21, Median cycles: 8
Systemic Drug: Drug: Paclitaxel protein bound/Abraxane, PUD: 260 mg/m², PDS: QD, Schedule: Cycle Day 1
Antiemetic Drug: Prochlorperazine/, Rt: IV/Oral, Dose: 10 mg, PDS: QID
OtherSupportiveDrug: Drug: Lorazepam/Ativan, Rt: IV/Oral, Dose: 0.5 mg, PDS: QD If you would like to make any changes to the evidence based treatment plan above, please click '<< Back' and you will re-enter the wizard. If you are satisfied with the treatment plan, click 'Complete >>' to complete your treatment plan and receive your exit code.

[ << Back ]   [ Complete >> ]

Product Name

Welcome Dr. Smith

Select Patient | Enter Diagnosis | Enter Treatment

Patient: Jane L. Public
Diagnosis: Breast Cancer: Adenocarcinoma - Invasive Ductal Carcinoma - Stage IV Treatment Plan: Albumin-bound Paclitaxel (Abraxane) in Recurrent/Metastatic Breast Cancer Treatment Plan Complete!
Here is your treatment Plan code for this treatment plan

EV-10002345

Submit this code with the electronic claims associated with this treatment

FIG. 9M

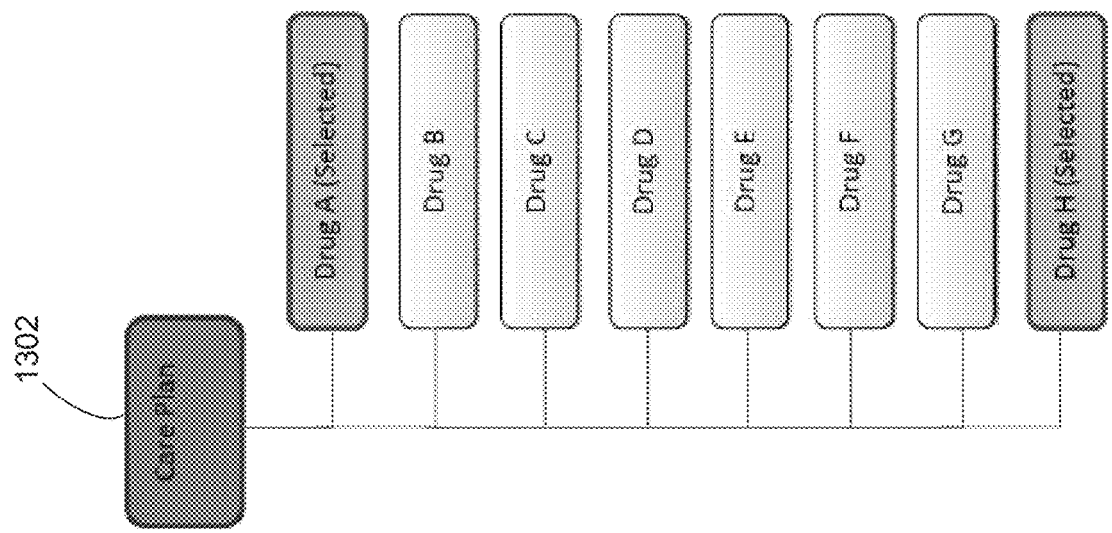
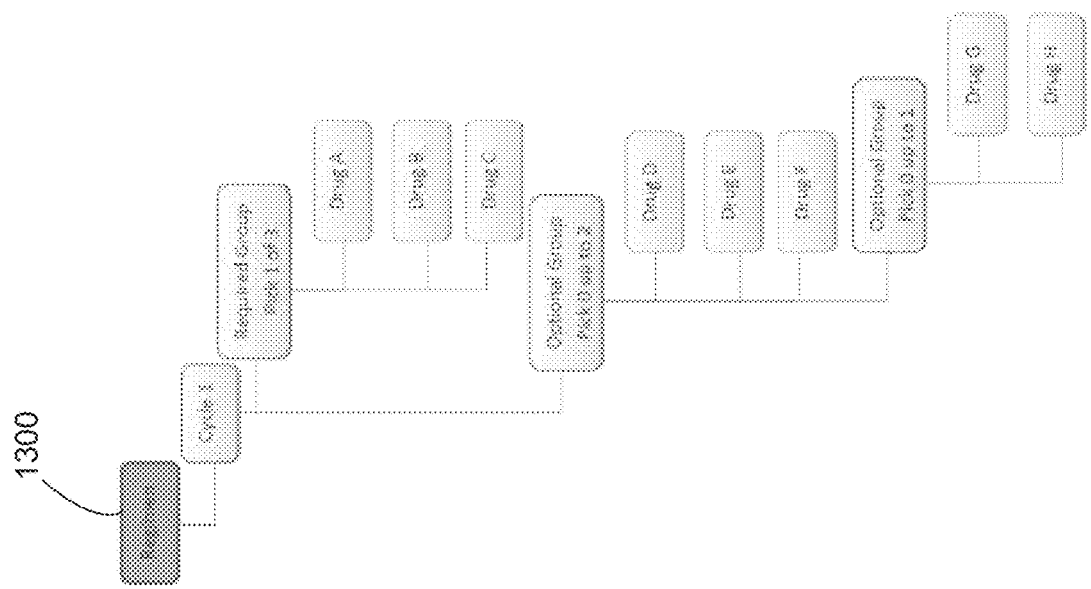
Figure 11F

AUTOMATED MEDICAL DIAGNOSIS, RISK MANAGEMENT, AND DECISION SUPPORT SYSTEMS AND METHODS

REFERENCE RELATED APPLICATIONS

This application is a continuation-in-part of U.S. Non-Provisional patent application Ser. No. 12/632,426, filed on Dec. 7, 2009, which is a continuation-in-part of U.S. Non-Provisional patent application Ser. No. 12/271,315, filed on Nov. 14, 2008, which claims priority to and the benefit of U.S. Provisional Patent Application No. 61/003,062, filed on Nov. 14, 2007 and also claims priority to and the benefit of U.S. Provisional Patent Application No. 61/710,382, filed on Oct. 5, 2012, the disclosures of each of which are herein incorporated by reference in their entireties.

FIELD OF INVENTION

This invention relates to automated decision support systems and specifically support systems for generating treatment plans, supporting medical and financial decisions, and delivering medical treatment data using a computer.

BACKGROUND

The insurance and health industries are in a state of systemic change. Rising healthcare costs are compelling new business models and drawing new businesses into the marketplace as never before. Concurrently, improvements in medical results from treatment advances, coupled with an increasing aging population, are driving demand for new and better services. Some estimates of expected healthcare expenditures as a percentage of GDP are 25% by 2016. These realities have placed an enormous burden on the third party payer system. As incidences have increased, so has the exposure of insurers to catastrophic diseases.

What is desired is a method and system to improve medical and financial outcomes in cancer and other diseases.

SUMMARY OF THE INVENTION

The different aspects and embodiments disclosed herein use a computer or other processor-based device to transform patient related data (and other types of data) into treatment data, insurance data, treatment plans, decision data, and other types of data using various interfaces and processing steps. Information and reports are generated or displayed in response to the various steps described herein. One or more users are able to interact with various systems implementing the various methods described herein. The relevant systems automate the process of guiding users to the correct decisions by analyzing large volumes of data in combination with various knowledge bases, filters, software components, comparators, search engines, and other technical features described herein. In part, one system embodiment determines the intersection of relevant payer plan language and evidence-based medicine treatment options to facilitate generating a treatment plan for a patient having one or more conditions.

In one aspect, the invention relates to systems and methods of automating medical data processing and counseling. The method can be implemented using a computer.

In an embodiment, a method of automating medical data processing and counseling may be implemented using one or more computing devices. The method may include receiving, at the one or more computing devices, a selection of a condition associated with a plurality of diagnosis possibilities for a patient. The method may also include displaying, at the one or more computing devices, candidate treatment options based upon, at least in part, a condition associated with the plurality of diagnosis possibilities for the patient. The condition may be associated with the plurality of diagnosis possibilities for the patient. The methods may further include receiving, at the one or more computing devices, a selection of a candidate treatment option from the candidate treatment options displayed and a regimen associated with the candidate treatment option selected/The method may additionally include determining, at the one or more computing devices, a diagnosis for the patient based upon, at least in part, the condition associated with the plurality of diagnosis possibilities for the patient, the candidate treatment option, and the regimen. The diagnosis may be one of the plurality of diagnosis possibilities for the patient. Moreover, the method may include displaying, at the one or more computing devices, the diagnosis for the patient.

In an implementation, the method may include comparing, at the one or more computing devices, components of the candidate treatment option and the regimen associated with the diagnosis for the patient with evidence-based medicine criteria for treating a patient with the diagnosis. The method may further include displaying, at the one or more computing devices, a violation of the evidence-based medicine criteria for treating the patient with the diagnosis and an explanation of the violation. The method may also include receiving, at the one or more computing devices, a corrected candidate treatment and regimen.

In an implementation, the method may include generating an evidence-based medicine treatment plan using the one or more computing devices, for the patient, consistent with payment guidelines of a payer in response to receiving the corrected candidate treatment and regimen. The method may also include generating a treatment plan code, using the one or more computing devices, the treatment plan code associated with the evidence-based medicine treatment plan generated for the patient. The treatment plan code may be unique and specific to the patient and the evidence-based medicine treatment plan. Comparing the components of the candidate treatment option and the regimen associated with the diagnosis for the patient with the evidence-based medicine criteria for treating the patient with the diagnosis may also include comparing granular deviations of the candidate treatment option and the regimen associated with the diagnosis for the patient with the evidence-based medicine criteria. This may be done, for example, by comparing at least one of a dose, a treatment cycle, a drug, and a drug group associated with the candidate treatment option and the regimen associated with the diagnosis for the patient with a corresponding dose, treatment cycle, drug, or drug group associated with the evidence-based medicine criteria.

In an embodiment, a system for automating medical data processing and counseling may comprise one or more processors. The one or more processors may be configured to receive, at one or more computing devices, a selection of a condition associated with a plurality of diagnosis possibilities for a patient. The one or more processors may also be configured to display, at the one or more computing devices, candidate treatment options based upon, at least in part, a condition associated with the plurality of diagnosis possibilities for the patient. The one or more processors may further be configured to receive, at the one or more computing devices, a selection of a candidate treatment option from the candidate treatment options displayed and a regimen associated with the candidate treatment option selected. The one or more processors may additionally be configured to determine, at the one or more computing devices, a diagnosis for the patient based upon, at least in part, the condition associated with the plurality of diagnosis possibilities for the patient, the candidate treatment option, and the regimen. The diagnosis may be one of the plurality of diagnosis possibilities for a patient. Moreover, the one or more processors may be configured display, at the one or more computing devices, the diagnosis for the patient.

In an implementation, the one or more processors may be configured to compare, at the one or more computing devices, components of the candidate treatment option and the regimen associated with the diagnosis for the patient with evidence-based medicine criteria for treating the patient with the diagnosis. The one or more processors may also be configured to display, at the one or more computing devices, a violation of the evidence-based medicine criteria for treating the patient with the diagnosis and an explanation of the violation. The one or more processors may further be configured to receive, at the one or more computing devices, a corrected candidate treatment and regimen.

In an implementation, the one or more processors may be configured to generate an evidence-based medicine treatment plan using the one or more computing devices, for the patient, consistent with payment guidelines of a payer in response to receiving the corrected candidate treatment and regimen. The one or more processors may further be configured to generate a treatment plan code, using the one or more computing devices, the treatment plan code associated with the evidence-based medicine treatment plan generated for the patient, wherein the treatment plan code is unique and specific to the patient and the evidence-based medicine treatment plan. Comparing the components of the candidate treatment option and the regimen associated with the diagnosis for the patient with the evidence-based medicine criteria for treating a patient with the diagnosis may further include comparing granular deviations of the candidate treatment option and the regimen associated with the diagnosis for the patient with the evidence-based medicine criteria. This may be done by comparing at least one of a dose, a treatment cycle, a drug, and a drug group associated with the candidate treatment option and the regimen associated with the diagnosis for the patient with a corresponding dose, treatment cycle, drug, or drug group associated with the evidence-based medicine criteria.

In an embodiment, a system may include an analyzer module. The analyzer module may be configured to compare a treatment plan for a diagnosis with evidence based medicine criteria corresponding to the diagnosis at one or more computing devices. The analyzer module may include an analyzer engine configured to receive a configuration at the one or more computing devices. The analyzer engine may be further configured to run one or more analyzer rules in parallel based upon the configuration. The one or more analyzer rules may be associated with the evidence based medicine criteria. The analyzer module may also include an analyzer rules module including the one or more analyzer rules configured to run at the one or more computing devices. The one or more analyzer rules may be associated with one or more flags. The one or more flags may be associated with one or more violations of the evidence based medicine criteria. The analyzer module may further include a flags module including the one or more flags. The one or more flags may be associated with the one or more analyzer rules and may utilize one or more predefined error codes each having a unique code associated with an evidence based medicine criteria violation. The analyzer module may additionally include an analyzer configuration module configured to communicate, via the one or more computing devices, the configuration to the analyzer engine. The analyzer configuration module may include data representing which analyzer rules from the analyzer rules module to run for an analyzer engine instance.

In an embodiment the analyzer module may be further configured to store, at the one or more computing devices, an analyzer run including data representative of the configuration used during an analyzer engine execution run, a date and time of the an analyzer engine execution run, a duration of the analyzer engine execution run, parameters tied to a patient associated with the analyzer engine execution run, and a number of flags generated during the analyzer engine execution run. The analyzer rules module may include a care plan analyzer. The care plan analyzer may include setup logic and a base analyzer related to the evidence based medicine criteria. The analyzer rules module may further include a property analyzer configured to analyze, at the one or more computing devices, one or more properties of the treatment plan for the diagnosis. The analyzer rules module may additionally include a container requirements analyzer configured to analyze, at the one or more computing devices, one or more drugs or drug groups associated with the treatment plan for the diagnosis. The analyzer engine may be further configured to transfer, at the one or more computing devices, analyzer data associated with the one or more flags associated with the one or more analyzer rules, to a master flag list. The master flag list may include the flags occurring during an analyzer execution run, the flags occurring based on evidence based medicine criteria violations.

In one aspect, the invention relates to methods and system of automating medical data processing and counseling. The method can be implemented using a computer. The method includes the steps of obtaining parameters related to a patient's health using a computer interface; obtaining a proposed treatment plan for the patient using the computer interface; comparing the proposed treatment plan for the patient with a set of medically-based criteria for treatment to determine if the proposed treatment plan meets the requirements for treating the patient, the set of medically-based criteria resident in a database, the comparison performed using a comparator resident in the computer; generating a patient prognosis in response to the proposed treatment plan and the patient parameters; generating a risk management assessment in response to the proposed treatment plan and the patient prognosis; and displaying information selected from the group consisting of the treatment plan, the patient prognosis, and the risk management assessment.

In one embodiment, the method includes step of modifying the proposed treatment plan to form a new treatment plan if the comparing step indicates that the proposed treatment plan does not meet the requirements for treating a patient. The steps of generating the patient prognosis and the risk management assessment are performed in response to the new treatment plan, in one embodiment. The proposed treatment plan can be prepared by the patient's health care provider. The risk management assessment can be provided to a patient's health care insurer, patient, and/or the provider. In one embodiment, the method includes the step of obtaining insurance plan data for a patient and comparing the insurance plan data to the proposed treatment plan. Further, the method can include the step of generating at least one of a justified conflict or an unjustified conflict in response to the insurance plan data. The method can include the step of resolving an unjustified conflict through consultation with an insurer. In another embodiment the method can include the step of generating an action list for advising a user of proposed courses of action for the patient.

In one aspect, the invention relates to a system for automating medical data processing and counseling. The system includes at least one input device for inputting parameters related to a patient's health and a proposed treatment plan for the patient; a database includes a set of medically-based criteria for treatment of patients; a comparator in communication with the database for comparing the proposed treatment plan for the patient with the set of medically-based criteria for treatment in the database and generating a comparison output; a requirements processor in communication with the comparator to determine if the proposed treatment plan meets the requirements for treating the patient in response to the comparison output of the comparator and producing the results of the determination at an output; a prognosis processor in communication with the requirements processor and the database for generating a patient prognosis in response to the proposed treatment plan; the results of the determination by the requirements processor and the patient parameters; and a risk processor in communication with the prognosis processor for generating a risk management assessment in response to the proposed treatment plan and the prognosis output of the prognosis processor. In one embodiment, the system includes a data analysis module for estimating treatment exposure for calculating an actuarial reserve at a micro-level.

In another aspect, the invention relates to a system for risk management and decision support in medical treatment. In one embodiment, the system includes at least one input device for inputting parameters related to a patient's health and a proposed treatment plan for the patient; a database includes a set of medically-based criteria for treatment of patients; a means for comparing the proposed treatment plan for the patient with the set of medically-based criteria for treatment in the database and generating a comparison output, said means for comparing in communication with the database; a first means for processing, in communication with the means for comparing, to determine if the proposed treatment plan meets the requirements for treating the patient in response to the comparison output of the means for comparing and producing the results of the determination at an output; a second means for processing, in communication with the first means for processing and the database, for generating a patient prognosis in response to the proposed treatment plan; the results of the determination by the first means for processing and the patient parameters; and a third means for processing, in communication with the second means for processing, for generating a risk management assessment in response to the proposed treatment plan and the prognosis output of the second means for processing. In one embodiment, the database includes an element selected from the group consisting of clinical standards of care, expected clinical outcomes, related financial data, disease progression rate data and disease cost data. In another embodiment, the third means generates predicted future risk exposure reports in response to the disease progression rate data and disease cost data.

In one aspect, the invention relates to a system for evaluating future patient risk exposure. The system includes at least one input device for inputting parameters related to a patient's health; a database includes a set of disease progression rates and a set of related disease treatment costs; a comparator in communication with the database for comparing a treatment scenario in which a follow on treatment is performed relative to a non-treatment scenarios in which the follow on treatment is not performed, the comparator configured to compare functional relationships between non-follow on disease progression rates and non-follow on disease treatment costs associated with the first scenario and follow on disease progression rates and follow on disease treatment costs associated with the second scenario; and a graphic user interface configured to display a future risk exposure report, the future risk exposure report identifying benefits associated with performing the follow on treatment relative to not performing the follow on treatment.

In part, various embodiments of the invention relate to generating a treatment plan with an associated plan code such that the plan complies with payer guidelines and treatment options that are consistent with evidence-based medicine.

In one aspect, the invention relates to method of automating medical data processing and counseling, the method implemented using a computer. The method includes the steps of identifying a first subset of candidate treatment options from a set of potential treatments for a condition such that the first subset satisfies a set of evidence-based criteria for treating the condition, the condition associated with a plurality of diagnosis parameters of a patient, and filtering the first subset to identify preferred candidate treatment options that are consistent with payer plan language to generate a second subset of candidate treatment options, the second subset selected based upon (1) the plurality of diagnosis parameters associated with the patient and (2) compliance with payer plan language relevant to the patient; displaying a user interface that comprises a list of treatment plan options that are user selectable, the list of treatment plan options selected from the second subset using the computer; and generating an evidence-based medicine treatment plan using the computer, for the patient, consistent with payment guidelines of a payer in response to selecting treatment plan options from the list of treatment plan options.

In one embodiment, the method further includes the steps of obtaining the diagnosis parameters from a user; and obtaining the payer plan language from a database, the payer plan language comprising a plurality of payer plan language portions, wherein the evidence-based medicine treatment plan is consistent with the plurality of payer plan language portions. The plurality of payer plan language portions can be selected from a group consisting of a database encoded definition of medical necessity, a database encoded definition of experimental medicine, and a database encoded definition of unproven medical treatment. The payer can be selected from a group consisting of an insurer, a governmental entity, a third party administrator, a user, and an employer group.

In one embodiment, the method further includes the steps of generating a treatment plan code associated with the evidence-based medicine treatment plan generated for the patient. In one embodiment, the method further includes the steps of transmitting the treatment plan code to the user; and transmitting the treatment plan code and the evidence-based medicine treatment plan to the payer, such that when the code is presented by the user to the payer the evidence-based treatment plan for the patient will be processed and cost associated with the plan will be settled.

The user interface can include a form with a plurality of drop down menus comprising embedded questions and potential answers to the embedded questions generated in response to at least one of the diagnosis parameters. In one embodiment, the potential answers are consistent with evidence-based medicine guidelines based on the diagnosis parameters and previously selected treatment plan options for the patient.

Further, the user interface can include a form with fields for entering variable treatment information on a per patient basis, the variable treatment information automatically constrained to a predetermined set of possible inputs by the user interface in response to the condition and evidence-based medicine guidelines. In one embodiment, the variable treatment information is selected from the group consisting of medical procedures, radiation therapy parameters, drug selection, surgical procedures, drug dosing ranges, treatment scheduling parameters, chemotherapy parameters, numerical ranges, and pre-populated menus.

In one aspect, the invention relates to a system for automating medical data processing and counseling. The system includes a database that includes (1) a first set of medically-based criteria for treatment of patients; and (2) a plurality of payer plan language portions; a query module configured to receive diagnosis information, the query module programmed to identify a treatment set constructed in response to the first set and the second set, the treatment set comprising a plurality of evidence-based medicine selected treatment options that comply with at least one of the plurality of payer plan language portions; and a user interface arranged to display questions relating to the diagnosis information and treatment information and display a treatment plan, the treatment plan comprising at least a portion of the treatment set.

In one embodiment, the user interface includes a form with fields for entering the diagnosis information on a per patient basis, the diagnosis information automatically constrained to a predetermined set of possible inputs by the user interface in response to a medical condition and evidence-based medicine guidelines. The diagnosis information can be selected from a group consisting of patient specific parameters, symptoms, laboratory data, pathology information, prior treatments, test results, temperature, weight, blood pressure, imaging data, and patient data. The system can further include a treatment plan code module, the treatment plan code module programmed to generate a code associated with the treatment plan. In addition, the system can further include a code processing module that is programmed to receive the code and settle costs associated with the treatment plan if the code was previously authorized. The system can further include a report generation module programmed to generate a report in response to a user action or automatically in response to the system generating a treatment plan. In one embodiment, the report is selected from the group consisting of diagnosis checklist comprising items necessary to generate a treatment plan, a chemotherapy order, a prescription, patient instructions, payer forms, drug interaction guidance and cost breakdown of treatment options.

In one aspect, the invention relates to a computer system for automating medical data processing and counseling. The computer system includes an electronic memory device; and an electronic processor in communication with the memory device, wherein the memory device comprises instructions that when executed by the processor cause the processor to: display fields and receive patient diagnosis information and treatment options within a browser, and generate a treatment plan constructed in response to the diagnosis information and the treatment options, the treatment plan comprising an intersection of a set of evidence-based medicine accepted treatment options and a set of payment guidelines of a payer. In one embodiment, the patient diagnosis information is selected from a group consisting of patient specific parameters, symptoms, laboratory data, pathology information, prior treatments, test results, temperature, weight, blood pressure, imaging data, and other patient data.

In one embodiment, the treatment options are selected from a group consisting of medical procedures, radiation therapy parameters, drug selection, surgical procedures, drug dosing ranges, treatment scheduling parameters, chemotherapy parameters, numerical ranges, and pre-populated menus. The memory device can include instructions that when executed by the processor cause the processor to generate a plan code for the treatment plan. Further, in one embodiment, the plan code is transmitted by the computer and stored in a database such that when the plan code is presented to a payer a treatment payment results.

In one embodiment, the fields are programmed to receive the diagnosis information and treatment options on a per patient basis, the treatment options automatically constrained to a predetermined set of possible inputs by the processor in response to a diagnosis of a medical condition and evidence-based medicine guidelines. The memory device can also include instructions that when executed by the processor cause the processor to display a set of user interface queries in response to a user request to deviate from proposed treatment plan options, and compare responses to the queries to a database of medically justified treatment plan exceptions to determine if the request to deviate complies with evidence-based medicine guidelines. In one embodiment, the user interface queries relate to a query category selected from the group consisting of rationale for deviation, drug substitution, drug removal, addition of new drug, dosage modification, scheduling modification, radiation therapy modification, and surgery modification.

In one aspect, the invention relates to one or more tangible computer readable media encoded with software. The software includes computer-readable instructions operable, when executed, to cause one or more processors to: display fields and receive patient diagnosis information, and generate a treatment plan constructed in response to the diagnosis information, the treatment plan comprising treatment options selected from a database that satisfy payment conditions of a payer and are consistent with evidence-based medicine guidelines relevant to the diagnosis parameters.

The software can include computer-readable instructions operable, when executed, to cause one or more processors to generate a plan code for the treatment plan, the plan code is unique and specific to a patient, wherein the diagnosis information is specific to the patient. In one embodiment, the software comprises computer-readable instructions operable, when executed, to cause one or more processors to settle cost associated with the treatment plan when the plan code is electronically presented.

In one aspect, the invention relates to a processor-based method of collecting diagnosis information for a patient and generating a treatment plan for the patient. The method includes (a) inputting diagnosis information related to the patient using a graphic user interface and storing the diagnosis information; (b) selecting a set of evidence-based medicine accepted treatment options and a set of payer plan language conditions, each of the selected sets defined in response to the diagnosis information related to the patient using an electronic processor; (c) automatically filtering a set of general treatment options using the processor, the filtering performed using the set of evidence-based medicine accepted treatment options and the set of payer plan language conditions; and (d) generating a treatment plan comprising a subset of the set of general treatment options that result from step (c), the treatment plan reciting treatment options that satisfy payment conditions of a payer and are consistent with evidence-based medicine guidelines relevant to the diagnosis parameters.

In one embodiment, the cardinality of the set of general treatment options is larger than the cardinality of the set of evidence-based medicine accepted treatment options. The method can further include the steps of generating a treatment plan code associated with the treatment plan generated for the patient. In one embodiment, the method further includes the steps of transmitting the treatment plan code to a user; and transmitting the treatment plan code and the treatment plan to the payer, such that when the code is presented by the user to the payer cost associated with the treatment plan for the patient will be settled.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. The drawings associated with the disclosure are addressed on an individual basis within the disclosure as they are introduced.

FIGS. 3A-3I are a series of on-screen representations relating to enrolling a user in an automated medical data processing and counseling system, in accordance with an embodiment of the invention.

FIGS. 4A-4B are a series of on-screen representations relating to task generation in an automated medical data processing and counseling system, in accordance with an embodiment of the invention.

FIGS. 5A-5E are a series of on-screen representations relating to a diagnosis process flow in an automated medical data processing and counseling system, in accordance with an embodiment of the invention.

FIGS. 6A-6G are a series of on-screen representations relating to a computer-based treatment plan as implemented in an automated medical data processing and counseling system, in accordance with an embodiment of the invention.

FIGS. 9A-9M are a plurality of display screens depicting user interfaces for collecting and transmitting information relating to treatment plan options and other user information of interest, in accordance with an embodiment of the invention.

FIGS. 11A-11I are example software-based modules, frameworks, and/or APIs in accordance with an embodiment the invention.

DETAILED DESCRIPTION OF THE PREFERRED EMBODIMENT

Figure 1:
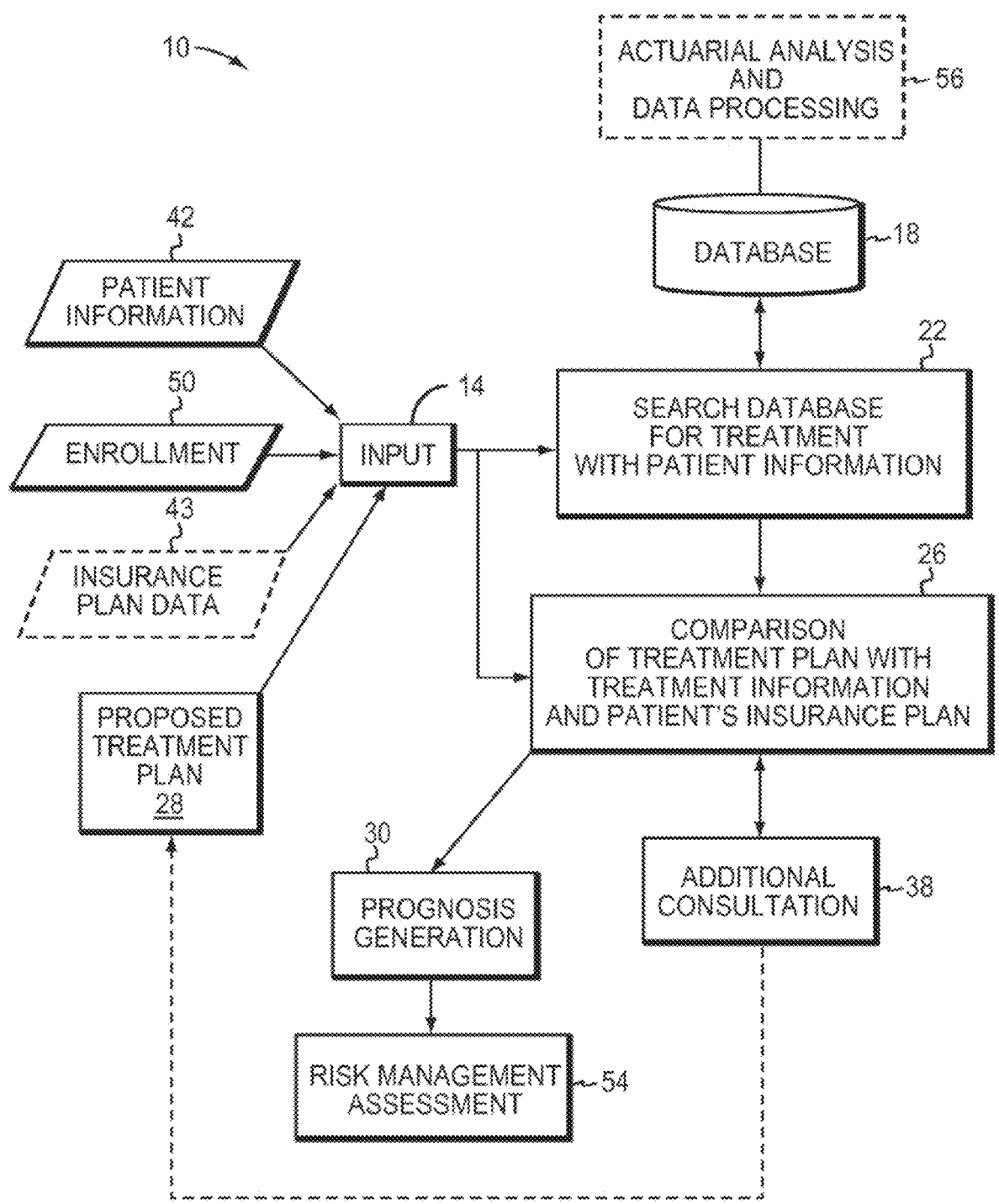
FIG. 1 is a block diagram of an embodiment of an automated system and method constructed, in accordance with an embodiment the invention.

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention, rather the scope of the present invention is defined by the claims.

It should be understood that the order of the steps of the methods of the invention is immaterial so long as the invention remains operable. Moreover, two or more steps may be conducted simultaneously or in a different order than recited herein unless otherwise specified.

The use of sections or headings in the application is not meant to limit the invention; each section and heading can apply to any aspect, embodiment, or feature of the invention.

It should be understood that the order of the steps of the methods of the invention is immaterial so long as the invention remains operable. Moreover, two or more steps may be conducted simultaneously or in a different order than recited herein unless otherwise specified.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The terms "a," "an," and "the" mean "one or more," unless expressly specified otherwise.

The foregoing, and other features and advantages of the invention, as well as the invention itself, will be more fully understood from the description, drawings, and claims.

One of the purposes of the system and method embodiments of the invention is to compare patient medical condition information, a proposed treatment plan for the patient and good practice standards to determine if the patient is getting the prescribed best practices treatment for his or her medical condition, such as a disease or other trauma. If the proposed treatment plan meets the best practices for treatment, the prognosis of the patient under the treatment plan is produced and a cost and outcome report is generated for the patient's insurer.

Another purpose of the system and methods embodiments described herein is to streamline the process of generating a treatment plan for a patient diagnosed with a condition by presenting a user interface to a physician, medical service provider, or other user that receives diagnosis information and generates a filtered list of treatment options. Further, the list of filtered treatment options satisfies evidence-based medicine criteria. In addition, the list also satisfies plan language requirements of a payer, such as a payer's payment guidelines. As used herein, a payer refers to any individual person, entity or organization that provides (1) plan language, regulations or guidelines or (2) financial consideration or other consideration for the services and materials provided by a medical service provider. Examples of a payer include, but are not limited to an insurer, a governmental entity, a third party administrator, a financial institution, a corporate entity, a user, and an employer group.

In general, physical data associated with a patient and their treatment regimen is processed using one or more computers and underlying software components to generate on-screen and other electronic media-based guidance, recommendations, and reports. Diagnosis information is collected using a user interface such as a browser based interface. Various knowledge bases (KBs) that include rules and best practices from evidence-based medicine (EBM) are used in conjunction with various components described herein to provide an automated system to support various treatment, diagnosis and case management (CM) functions. EBM is the conscientious, explicit and judicious use of current best evidence in making decisions about the care of individual patients. The practice of evidence-based medicine requires the integration of individual clinical expertise with the best available external clinical evidence from systematic research and the patient's unique values and circumstances.

In contrast, if the proposed plan does not correspond to best practices, then a discussion with the treatment plan provider may occur in an attempt to induce him to or her to modify the plan to correspond to the best treatment practices. The evidence for this discussion is on-screen or other guidance generated by one or more of the automated medical data processing and counseling systems (an related methods) described herein.

Typically, the systems and methods described herein are implemented using computer-based medical and business decision making that uses real world treatment and patient data. Further, the system components, modules, subsystems, databases, methods and other components described herein can be arranged in any suitable order or actuated in any suitable sequence, as appropriate. A client-server based approach is used in one preferred embodiment. Typically, the server has a database and various software components or modules and applications which are accessed and interfaced with using a local or remote client, such as a browser-based application.

Although various individuals and entities are described herein as using the systems and methods described herein, in general, the system and methods can be accessed and used by a wide range of users. An exemplary class of users of the systems and methods disclosed herein include, but are not limited to medical staff, doctors, nurses, HMOs, hospitals, oncology care providers, renal care providers, cardiac care providers, care givers, sales personnel, financial services personnel, insurance company personnel, underwriters, actuaries, patients and assessors of medical risk and treatment.

In one embodiment, the methods and systems described herein can also compare patient treatment plan data relative to the rules, conditions, and limitations, recited within a payer's plan language which may correspond to a patient's insurance policy or plan. This payer plan data or insurance plan data can be stored and processed in various suitable formats and file configurations. Thus, payer plan data or language can include payment guidelines, payer plan language portions, definitions specific to a payer's business, and other criteria or requirements of a payer.

If the proposed treatment plan generated by the system conflicts with the insurance plan, the system will alert at least one of the patient's care givers or case managers, such that the party receiving the alert may contact the patient's treating physician or the insurer to adjust one of the physician treatment plan or the requirements of the insurer's plan. Once a treating physician has been contacted, the treatment plan can be modified to comport with the insurance policy language. In contrast, if the system contacts the insurer, the administrator of the relevant patient's treatment plan can explain why the proposed treatment plan is beneficial and can suggest that the insurer cover the costs of the proposed treatment plan and accept the deviation from the insurance policy.

In some embodiments, this alert and reconciliation process is carried out automatically using an automated conflict resolution system. Thus, the system can process justified conflicts and alert a user to a problem, such as with an on-screen message, email, or other alert type. In turn, after processing an unjustified conflict, the system can inform a user that consultation with a member of the medical staff and/or an insurer is required. This allows resolution of the unjustified conflict to benefit of the patient in some embodiments.

In general, "best practices" are a widely accepted set of practices which represent the standard of care for the particular disease state as defined by the medical profession and which are generated in response to at least one of medical data, actuarial data, insurer data, treatment data, cost data, patient data, statistical models, and relational data.

A related, but conceptually different aspect of the invention relates to systems and methods that enable a provider to automatically or substantially develop an evidence-based treatment plan by filtering an evidence-based medicine knowledge base relative to the diagnosis information and certain payer plan language to provide a list of treatment plan options that are evidence-based and meet payer plan language guidelines. Typically, the plans that result from the selection of treatment options by a provider will automatically be settled or settled on an expedited basis given the fact that they are tailored to comply with the applicable payer's guidelines. A code can be created and associated with each plan, such as a plan code. In one embodiment, such a code indicates compliance with payer plan language which enables a payer to automatically or substantially automatically settle certain patient costs when the code is presented.

In brief conceptual overview and referring to FIG. 1, an exemplary automated system 10 constructed in accordance with the invention includes at least one input device 14, such as a computer, mobile device, or other device with an electronic interface suitable for receiving real world data, a database 18, and a search engine 22. The search engine 22 receives its input data from both the input device 14 and the database 18. The results of the query by the search engine 22 are the best practices for the patient's medical condition and are the input data to a comparator 26.

In one embodiment, the comparator is implemented in software as a browser based system created using a web application framework such as, but not limited to Microsoft ASP.NET. The other input data to the comparator 26 is a proposed treatment plan from the input device. In another embodiment, the acceptable practices and other requirements associated with a particular insurer's insurance plan can also serve as an input to the comparator 26.

Accordingly, in one embodiment, comparing the treatment plan relative to a standard of care and the requirements of a given applicable insurance policy allows both business and patient needs to be evaluated. If a conflict exists, the system notifies staff to contact the insurance company to resolve the conflict. During the process of resolving a conflict, primary insurers may make an exception based on the recommendation that a particular treatment approach, such as the off label use of a new drug, is appropriate for the treatment plan. Further, to the extent that proper medical treatment risk outweighs strict compliance with the restrictions of typical insurance plan, the comparative approach described herein allows both patients and insurers to achieve mutually beneficial outcomes.

The output of the comparator 26, which can be a determination as to whether the proposed treatment plan corresponds to best practices, is passed to the input of a prognosis generator 30 whose output data is the input data to a risk management assessment generator 34. The risk management assessment generator 34, in response to the patient data, the best practices determination and the proposed treatment plan produces a prognosis for the patient and a risk assessment, such as the cost of the treatment proposed, to an insurer, hospital, or other cost bearing entity.

If more information is desired or if the comparator 26 determines that a proposed patient treatment plan 28 does not comport with current best practice standards, or the requirements and conditions of a particular insurer's insurance plan, as found in the database 18, additional consultation 38 may occur with the provider of the proposed treatment plan.

In more detail, a patient undergoes an enrollment process 50 in the system either at the behest of a provider, for example a doctor or insurer, and as a result, the patient's medical information 42 and proposed treatment plan 28 from the medical care provider, doctor or other clinician are input 14 into the system. The treatment plan can also be created using the systems of FIGS. 7A-8B. This data may be input into the system electronically through file sharing over a secure network, through manual input on a terminal, through facsimile or any other data transfer mechanism that provides for the secure transfer of data. For the purpose of FIG. 1, this information is shown as coming into and being retained in the input device, although such data storage would typically be in a secure memory or database.

The patient medical diagnosis and medical data is one input to a search engine 22 which searches a treatment database 18 for the treatments available to a patient with the patient's diagnosis. The treatment database 18 can include treatments relative to various disease pathologies, elective surgeries, physical trauma, such as burns, and various other ailments. The medical data of the patient may also have an effect in determining what the best course of treatment is for the patient. Thus, in one embodiment, patient medical data is also an input into the search engine 22. The search engine may simply use the diagnosis as the search term in a relational database to return the best practices treatment plan or may start with the diagnosis and, using the patient medical data, refine the search to determine the best practice treatment not only for the patient's medical condition, but also taking in account the present stage of the medical condition, such as a disease, in the patient.

The proposed treatment plan 28 from the medical care provider is then compared with the best practices treatment plan obtained by the search engine 22 from the database 18. This comparison is typically performed by an algorithmic module in a processor programmed to compare the various aspects of the treatment plans. In one embodiment, the comparison is performed by an expert system as is known to one skilled in the art.

If the output of the comparison is that the proposed treatment plan and the best practices treatment plan substantially correspond, the correspondence then permits the patient's prognosis to be generated 30 by another module of the computer. Again, in one embodiment this is performed by an expert system. Once the prognosis has been generated, a risk management assessment module 34, typically implemented as memory resident software, is then able to calculate what the cost of treatment will be and issue a report to the patient's insurer or other entity of interest.

If the proposed treatment plan and the best practices do not substantially agree, the system alerts a user 38 who can then contact the medical service provider who prepared the plan and discuss the fact that the provider may not be using best practices. If the medical provider agrees and changes the proposed treatment plan to correspond to best practices, the comparison 26 is rerun and the prognosis is generated 30 as described previously. If the medical provider disagrees and does not wish to change his or her proposed treatment plan this is reported to the insurance provider.

Figure 1A:
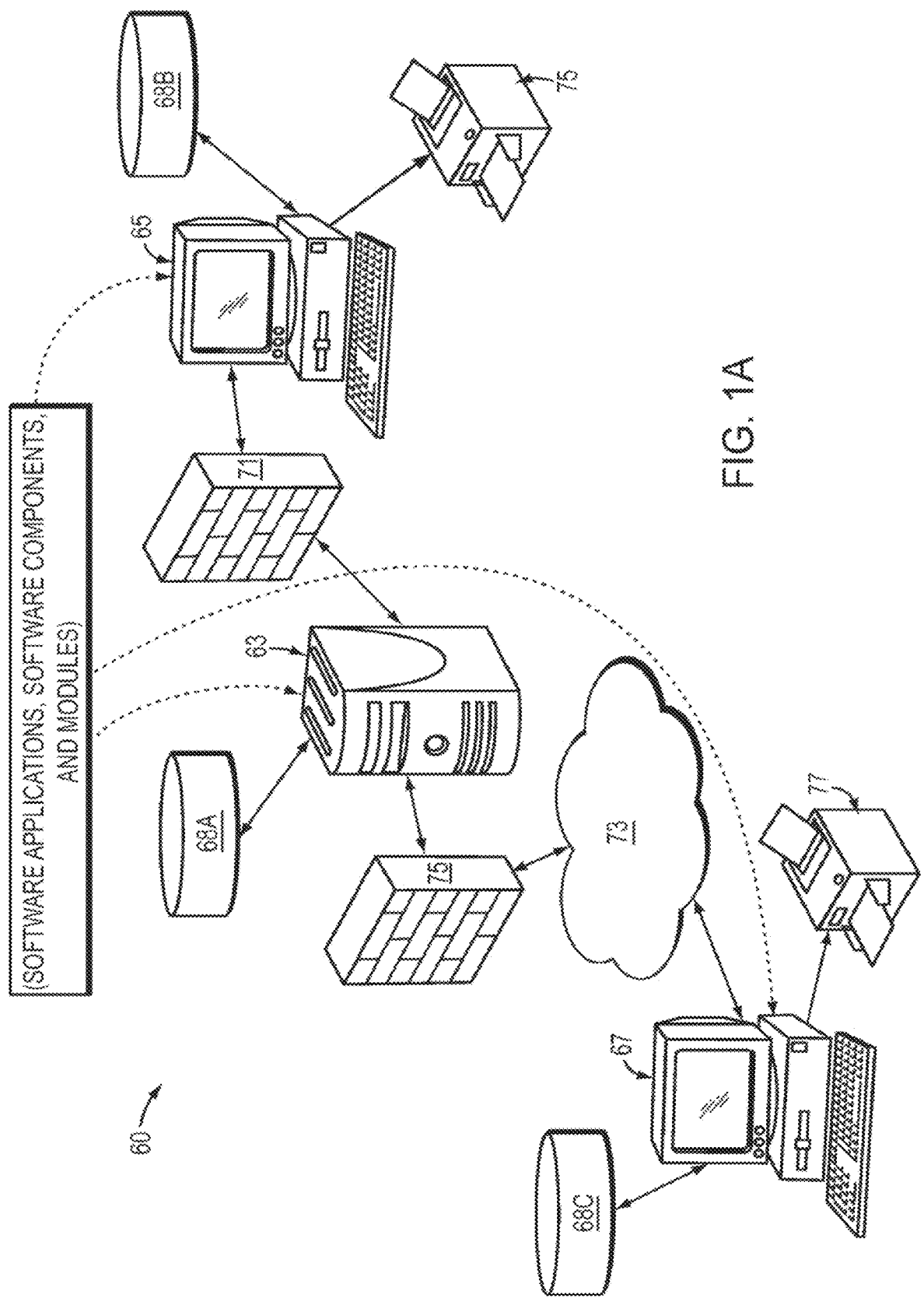
FIG. 1A is a block diagram of a various automated computer-based system implementations suitable for performing the process flow of FIG. 1, in accordance with an embodiment of the invention.

An exemplary computer-based system 60 for implementing an automated medical data processing and counseling system embodiment of the invention is shown in FIG. 1A. As shown in the figure, a central server 63 which includes a memory, network interface, and processor (not shown) directly or indirectly executes or interfaces with various software components/software modules. In one embodiment, the system API resides on server 63 along with a software platform or engine, such as Microsoft .net. The SQL server database 65 and 67 use a browser to access, and a reader to view reports. Various system and method embodiments described are or use web browser based asp-.net software systems. In one embodiment, the central server is accessed via a direct or remote connection by another computer 65, 67, such as a workstation, a terminal, or a device running a browser or interface application suitable for exchanging information with the server 63.

Alternatively, all of the software components/software modules necessary to run the methods and processes described herein can be directly installed on individual computers 65, 67 in other embodiments. Further, the software and modules described herein can be combined with other software systems as appropriate and offered as stand alone products. This feature is discussed in more detail below.

Embodiments of the invention also include search engines, automated decision making modules, filters, user interfaces, and other computer-based technologies that can be implemented using various software components, such as modules, programs, scripts, and routines. Typically, these are resident on a central server 63. However, in one embodiment, local versions can be configured on individual computers or terminals 65, 67. As used herein a software component or module refers to a software application (or portion thereof), routine, API, program, or data structure suitable for performing a specific task or responding to a certain command, signal or instruction. In one embodiment, the software components receive data relating to a physical scenario in the real world such as a patient receiving or about to receive treatment for a specific medical condition, such as cancer, renal disease, cardiac disease, etc. Further, this patient related data is transformed by the relevant software components to produce reports, guidance, recommendations or other tangible output to help the patient recover and to guide insurance providers and other parties of interest.

Thus, in one embodiment consistent with the treatment plan generation features described below, a patient diagnosis is transformed into a treatment plan that satisfies plan language requirements of a payer and evidence-based medicine treatment guidelines. Transforming a patient diagnosis into a treatment plan using a graphic user interface and related software modules enables efficiencies and improved patient outcomes that would otherwise be subject to greater uncertainty, risk, and non-compliance with payer plan requirements.

Typically, in a preferred embodiment a software component or module refers to a software routine, program, script, or other memory resident application suitable for receiving and processing instructions or various types of data with respect to automating medical and insurer counseling, medical treatment plan review, and insurer counseling.

Returning to FIG. 1A, in one embodiment, each of the server 63, and computers 65, 67 have an associated database, 68a, 68b, and 68c. In one embodiment, only one database is necessary. In another embodiment, only one server is necessary. As discussed in more detail below with respect to FIG. 2, the database includes various data that is electronically received using various on-screen interfaces and other technologies or otherwise generated to facilitate decision making and the operation of the embodiments described herein such as those depicted in FIGS. 1A-1C and in FIGS. 7A-9M.

With respect to computer 65, in the embodiment shown, this computer accesses the server 63 through a firewall 71 without accessing the internet 73. Alternatively, computer 67 accesses the central server 63 via the internet through firewall 75. As shown, firewalls, VPNs, and other encrypted or secure data transmission protocols are typically used in light of the sensitivity of patient data. Optionally, the computers 65, 67 can communicate with printers 75, 77 or other electronic media-based output devices to print, generate, display or otherwise archive on-screen alerts, guidance, plans, information, or reports generated by the system 60.

Figure 1B:
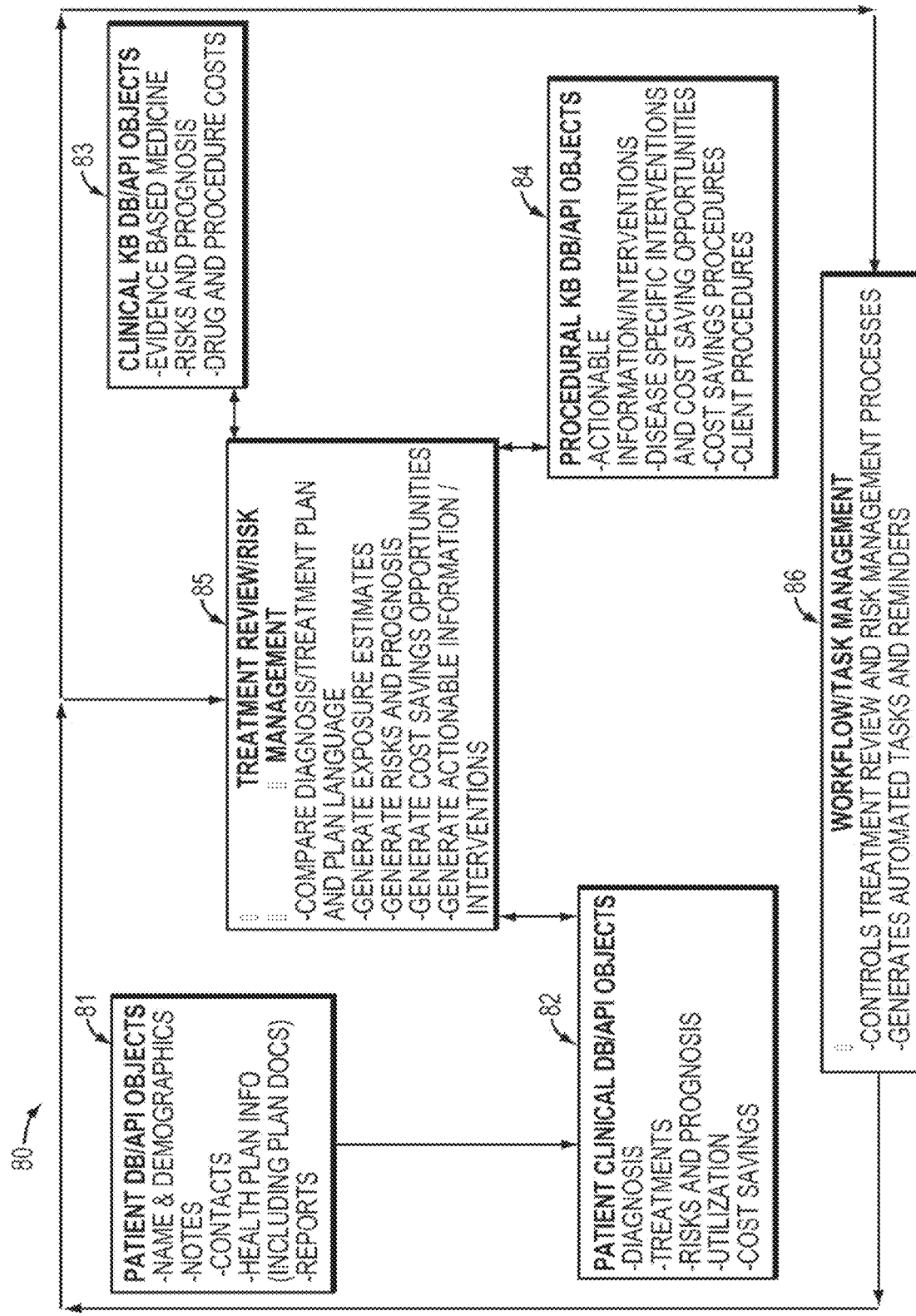
FIG. 1B is a process flow showing how tangible patient data and treatment data is transformed into reports and guidance using the automated embodiments of FIG. 1 and FIG. 1A, in accordance with an embodiment of the invention.
Figure 1C:
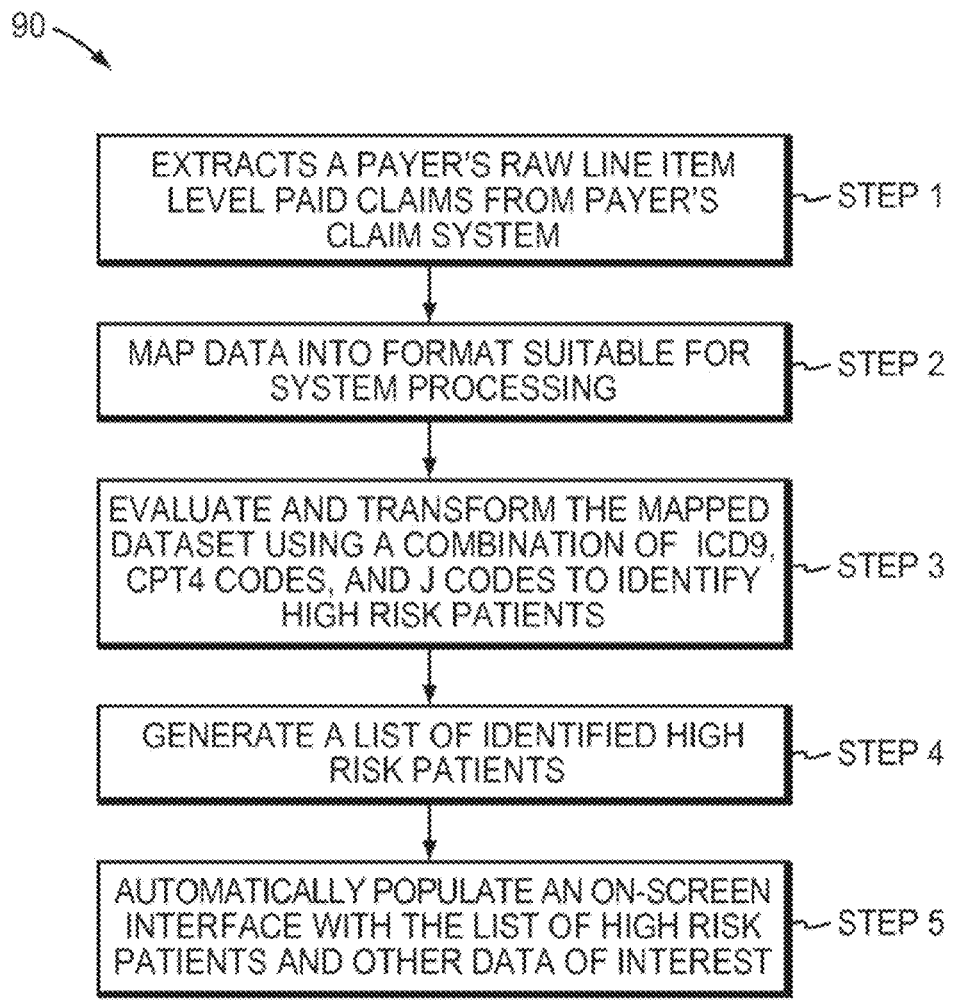
FIG. 1C is a process flow suitable for identifying certain candidate patients within an automated medical data processing and counseling system, in accordance with an embodiment of the invention.

The systems and methods shown in FIGS. 1A-1C and otherwise described herein can be implemented as stand alone applications or integrated with other software-based systems. Specifically, exemplary systems suitable for integrating with the embodiments disclosed herein include, but are not limited to a payer's enrollment system, a payer's claim system; a payer's underwriting system/data warehouse; and a provider's system. In one embodiment, a payer refers to an insurer including HMO, PPO, re-insurer, TPA, a self-insured employer, or other entities as appropriate. Similarly, in this context provider refers to a physician, technician, nurse practitioner, hospital or health services institution, pharmacy, or other entities as appropriate.

In one embodiment, the automated systems and methods described herein use the eligibility system to ensure the identified patient has benefits with a given payer. Similarly, when the embodiments described herein are integrated with a payer's claim system numerous new abilities and system features are possible. These include adjudicating billings with automated system or system provider approved treatments, billing thresholds, and recommended procedures based on diagnosis/treatment; automation of patient identification for risk management using the process flow of FIG. 1C; ensuring screening and recommended procedures are taking place based on patient demographic and diagnosis specific characteristics; the ability to review submitted claims prior to approval to ensure billings follow approved treatment plans; the ability to review claims history to ensure that all members who need risk management have been identified; and the ability to check to see if post-treatment diagnostic procedures are being performed in accordance with evidenced-based medicine guidelines.

Furthermore, when the embodiments described herein are integrated with a payer's underwriting system or data warehouse numerous new abilities and system features are possible. These include the ability to assign risk factors to individuals as well as populations for use in underwriting and reserving and the ability to assign a case reserve amount to individuals as well as populations for use in underwriting and reserving. Creating a case reserve refers to the ability to assign retrospective risk factors to explain prior experience as well as prospective risk factors to predict future experience to be taken into account in the underwriting process. Thus, the case reserve amount can be equivalent to expected future liabilities for payer.

In addition, when the embodiments described herein are integrated with a provider's system, numerous new abilities and system features are possible. These include the ability to check if a treatment will be reimbursed by a particular payer; the ability to check if a treatment will meet evidenced-based medicine criteria (typically, EBM criteria are selected parameters that apply evidence gained from available research and real world data to certain parts of medical practice); the ability to notify provider of treatment received by a patient by other providers, forming a patient record; and the ability to identify potentially harmful drug interactions.

In one embodiment, the automated systems and methods described herein use some or a subset of the components shown in the system of FIG. 1A to receive diagnosis information from a medical provider using an interface, such as a browser based interface and display treatment options to the provider. In turn, the treatment options are filtered to comply with plan language portions and evidence-based medicine guidelines. In one embodiment, the provider may elect to deviate from the propose treatment options. In such an embodiment, various analysis steps such as those described herein relating to third party plan review can be triggered. In addition, in one embodiment, a set of anticipated deviations that are compliant or non-compliant with evidence-based medicine guidelines are stored to facilitate automated evaluation of the provider's selected deviation from the presented treatment plan options. In yet another embodiment, the various components of FIG. 1A are used to electronically or otherwise transmit a treatment plan code or plan code that indicates that a particular treatment plan has been generated for a given patient and that such plan complies with the relevant plan language for that patient's payer as well as complies with the applicable evidence-based medicine guidelines.

The embodiments shown in FIGS. 1 and 1A operate using various process flows (such as those depicted in FIGS. 1B and 1C and FIGS. 7A-8B) and various on-screen interfaces, guidance, and other information (such as those depicted in FIGS. 3A-6G and FIGS. 9A-9M).

In FIG. 1B, a process flow 80 showing the types of data and the flow and transformation of such data in an exemplary automated medical and risk counseling system is shown. Specifically, a patient specific software module or component 81 includes or interfaces with a plurality of patient related database objects or application programming interface (API) objects. Thus, in part, in one embodiment, the system can be configured as a closed loop implementation of a risk management process for catastrophic illness risk management.

The exemplary, non-limiting set of patient specific database or API objects includes name & demographics, notes, contacts, health plan information, plan documentation, and reports. The patient specific software component 81 and related patient data are used by a related patient clinical information specific software module or component 82. In one embodiment component 82 is an extension of component 81, having the properties of component 81. Generally, the APIs discussed herein refer to software objects that interact with both the graphic user interfaces and any databases used that contain all necessary business logic.

A patient clinical information specific software module or component 82 includes or interfaces with a plurality of patient clinical information related database objects or application programming interface (API) objects. The exemplary, non-limiting set of patient clinical information related database objects or API objects includes diagnosis, treatments, risk and prognosis, utilization, cost savings.

Further, a clinical knowledge base specific software module or component 83 includes or interfaces with a plurality of clinical knowledge base related database objects or application programming interface (API) objects. The exemplary, non-limiting set of clinical knowledge base related database objects or API objects includes evidence-based medicine, risks and prognosis, and drug and procedure costs. In one embodiment, either the clinical knowledge base or an additional knowledge base is used that includes a set of medically justified exceptions and logic for validating the applicability of such exceptions relative to the treatment plan generated using the systems and methods described herein.

In addition, a procedural knowledge base specific software module or component 84 includes or interfaces with a plurality of procedural knowledge base related database objects or application programming interface (API) objects. The exemplary, non-limiting set of procedural knowledge base related database objects or API objects includes case management guidance, disease specific interventions and cost saving opportunities; and client procedures.

A central component of the process flow 80 is a treatment review/risk management software component 85. This management component 80 exchanges information with each of components 82, 83, 84 and the underlying database objects and APIs associated with each of these components 82, 83, 84.

The treatment review/risk management software component 85 performs various data comparison and processing steps. One step performed by the component 85 is to compare diagnosis/treatment plan and plan language with EBM. The step of comparing a provider's proposed treatment related specifically to the patient's diagnosis is performed relative to accepted evidence-based medicine treatments relating to a specific diagnosis, along with payer's plan language.

As a result of this comparison and the identification of compatible features and discrepancies between the management component 85 generates various on-screen outputs and guidance. In one embodiment, as a result of the comparison, the component 85 generates one or more of the following: exposure estimates, risks and prognosis, cost savings opportunities, and actionable information/interventions. With respect to the generation of actionable information/interventions, the system (or a component thereof) generates patient specific risk management interventions including diagnosis and treatment education, cost saving opportunities that are based on diagnosis, treatment, and prognosis.

In turn the management component 80 is controlled or regulated using a software-based workflow/task management software component 86. This component 86 controls the treatment review and risk management software component 85 and any underlying processes. Further, this work/flow task management component 86 also generates automated tasks and reminders.

Another specific process flow embodiment that relates to identifying high risk patients using an embodiment of an automated medical counseling system is shown in FIG. 1C. The process flow 90 shown in FIG. 1C includes various underlying steps. Initially, a program extracts a payer's raw line item level paid claims from payer's claim system (Step 1). Next, data is mapped into a specific format suitable for use by the automated medical counseling system embodiment (Step 2). The format of the data at this stage includes, but is not limited to include: Unique Patient Identification number, Date of Service, Procedure Codes 1-10 (cpt4, HCPC Level III including J codes, NDC codes, ICD9 procedure codes, and Diagnosis Codes 1-10 (ICD9 diagnosis codes, with the ability to adapt to ICD10).

Another step in the process flow is to evaluate and transform the mapped dataset using a combination of ICD9 codes, CPT4 codes, and J codes to identify high risk patients (Step 3). In one embodiment, a diagnosis code is a primary indicator of a disease the system or its user seeks to identify. By itself, in some embodiments diagnosis codes are supplemented because a given code may not be sufficient due to vagueness of codes, or common coding errors. Thus, in one embodiment, the system and methods use a procedure code (in concert with a diagnosis code) to ensure that expected treatments for that diagnosis are occurring. This also facilitates greater confidence that the identified patient is a suitable candidate for risk management. Further, in one embodiment a procedure code may be insufficient by itself because some procedures can be used for multiple diagnoses. Also, technical detail will vary greatly based on illness, in some embodiments, that can limit the effectiveness of only using one code.

After this process, a list of identified high risk patients is generated (Step 4). Finally, as another step the system automatically populates an on-screen interface with the list of high risk patients and other data of interest (Step 5).

Figure 2:
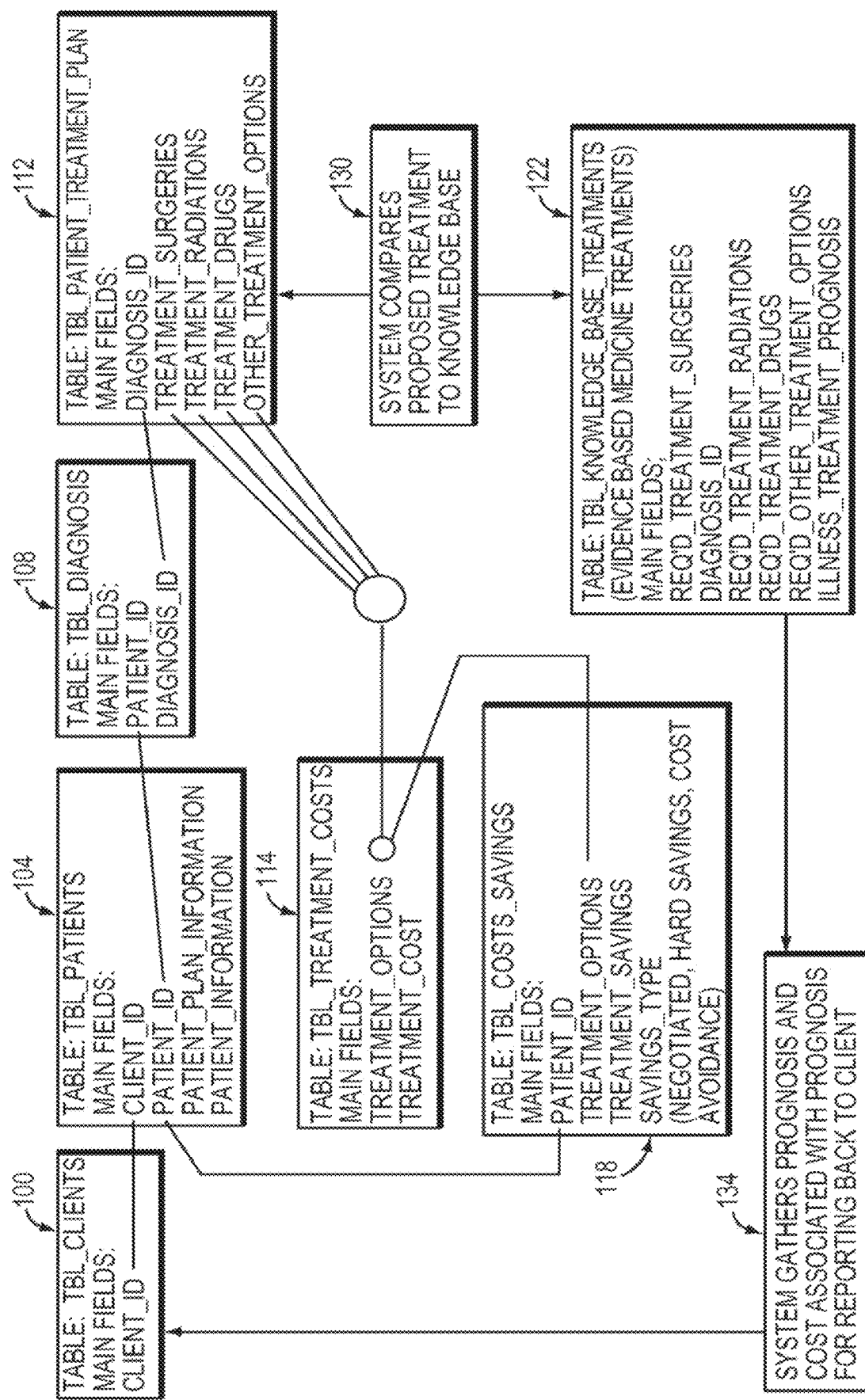
FIG. 2 is a block diagram of an embodiment of a database structure and relationships constructed, in accordance with an embodiment of the invention.

Referring to FIG. 2, an embodiment of a database structure suitable for use in embodiments of the invention is shown. This database structure (or another compatible structure) can be replicated in one or all of the databases 68a, 68b, or 68c in a given embodiment. Although this structure is referred to as a database structure, it may also include a series of tables, as shown in the embodiment of FIG. 2. In this embodiment, the database system includes seven tables: table of clients (tbl_clients) 100, table of patients (tbl_patients) 104, diagnosis table (tbl_diagnosis) 108, table of the patient's treatment plan (tbl_patient treatment_plan) 112, table of treatment costs (tbl_treatment_costs) 114, table of cost savings (tbl_costs_savings) 118 and table of knowledge base treatments (tbl_knowledge_base_treatments) 122 which correspond to the treatments corresponding to best practices in the knowledge database. Each table includes several fields or variables. These various tables can be cross-sorted and filtered to generate the various sets and subsets depicted in FIG. 7A on a per patient basis or as part of a batch process for multiple patients with diagnosis information.

The table of clients 100 is a table which primarily lists the client's identity and contact data, for example an insurer's, identification number can be used in one embodiment of the table of clients 100. This client identification number links the table of clients 100 to the table of patients 104. The table of patients 104 includes not only the client identification number, but the patient's identification number, the patient plan information and a link to the specific medical information about the patient. The patient identification number links the table of patients with the diagnosis table 108 and the table of cost savings 118.

The table of cost savings 118 includes, but is not limited to treatment options, treatment savings, and savings type. The savings type is typically one of negotiated savings, hard savings and cost avoidance. The treatment options links the table of cost savings 118 to the table of treatment costs 114. The table of treatment costs 114 includes, but is not limited to treatment options and treatment costs for that option.

The diagnosis table 108 includes not only the patient identification number but the diagnosis identification number for the patient. The diagnosis identification number links the diagnosis table 108 with the table of the patient's treatment plan 112. Similarly, the treatment options of the table of treatment costs 114 also link the table of treatment costs 114 to the table of the patient's treatment plan 112. This diagnosis and treatment information can be filtered using payer plan language as described herein.

The table of the patient's treatment plan 112 includes the various treatment options. For example, in the case of a patient with cancer, the potential treatment plans are surgical, radiation, drugs and other.

The last table is a table of best practices treatments 122 for the medical condition affecting the patient and the prognosis resulting from them. This table includes required treatments in surgery, radiation, drugs and other treatment options as well as a treatment prognosis if those treatments are used. When diagnosis information is generated by a provider, this information is used to select treatment options from table 122 that comply with applicable payer plan language which is also stored or encoded in a table.

In use, the client table 100, the patients table 104, the table of diagnosis 108 and the patient's treatment plan 112 are populated with information entered when the patient is enrolled and the client engaged. In one embodiment, a patient eligibility determination process can be performed using the automated systems and methods described herein. In one embodiment, a patient is eligible if they are listed as members in the payer's census, database or other records.

The treatment cost table 114, the cost savings table 118 and the best practices table 122 are the same for all patients and clients and are entered when the system is constructed and updated as needed.

The system compares 130 the best practices data for the diagnosis identification number in the best practices table 122 to the treatment plan data for the same diagnosis identification number in the patient's treatment plan table 112. The system then gathers 134 the prognosis information and the costs associated with the prognosis and reports the prognosis and costs to the insurer.

In certain embodiments, where insurer policy restrictions are also considered, the system identifies the relevant policy language in conflict with a particular treatment plan. This language can be transmitted to the insurer to help understand the nature of any conflict with their policy. In some circumstances, resolving these conflicts in favor of the treatment plan is often beneficial to both the patient and the insurer because failing to treat a patient using the best practices may far exceed the costs associated with deviating from the insurance plan.

In another embodiment, the systems and methods described herein can also provide a user of the system, such as a patient or medical practitioner, with guidance regarding appropriate educational information for a particular patient. The guidance is typically displayed or transmitted using an electronic representation such as an email or on-screen image. In one embodiment, the educational information can be an action list for a medical practitioner or other system user to review with the patient. The action list can include, but is not limited to educating the patient about dietary changes, self-care, and drug interactions; providing information about when to call his or her treating physician; how to prevent or alleviate side effects; and preparing the patient to communicate with his/her treating physician.

In some embodiments, the system also can identify cost savings opportunities for the user. Examples of cost savings opportunities include locating a less expensive supplier of a certain medication or providing the data necessary to negotiate a cost savings with certain medical goods or drug suppliers.

In another embodiment, the systems and methods described herein can also provide a user of the system, such as a patient, a case worker, an auditor, or a medical practitioner, with case management information, clinical information, or any related cost information regarding the various types of data and information described throughout and in the figures.

The system also includes functionality relating to actuarial analysis and data processing. In one embodiment, the data processing and actuarial analysis discussed below is performed using processing module 56. In another embodiment, the system also can provide estimates of remainder-of-care costs. These cost estimates may be provided to the insurer and can permit the insurer to calculate their actuarial reserves. The actuarial reserves are monetary allocations by insurers for future patient medical liabilities for treatment costs. The system can provide accurate treatment estimates on a per patient basis, which can increase the accuracy of the actuarial reserve allocations. Given the detailed information regarding the costs of the treatment plans, the systems and databases described herein allow for actuarial reserves to be calculated on a micro-level on a per patient basis. This approach provides greater accuracy relative to existing prior art approaches.

The system also can generate detailed cost savings for insurers and other users of the system such that the benefits of using the system relative to not using it are clearly demonstrable. In addition, the system and databases described herein can be used to determine cost avoidance data. Such data is valuable to insurers and other business entities. For example, if the system provided educational material or generated a treatment plan that prevented a week long hospital stay, with an associated cost of approximately $14,000, the system can report the savings to the insurer. The system also can predict the cost savings through the remainder of treatment or care. Thus, the system includes numerous actuarial and statistical modules that allow actuarial data and other numerical data of interest to insurers to be calculated and extrapolated upon.

Although this data structure captures all the information necessary to permit the system to function, other data structures are possible. Also although the system is described in terms of multiple processor modules, the functions of the system may be equivalently performed by a single module/software component or combinations of modules/software components.

Figure 10:
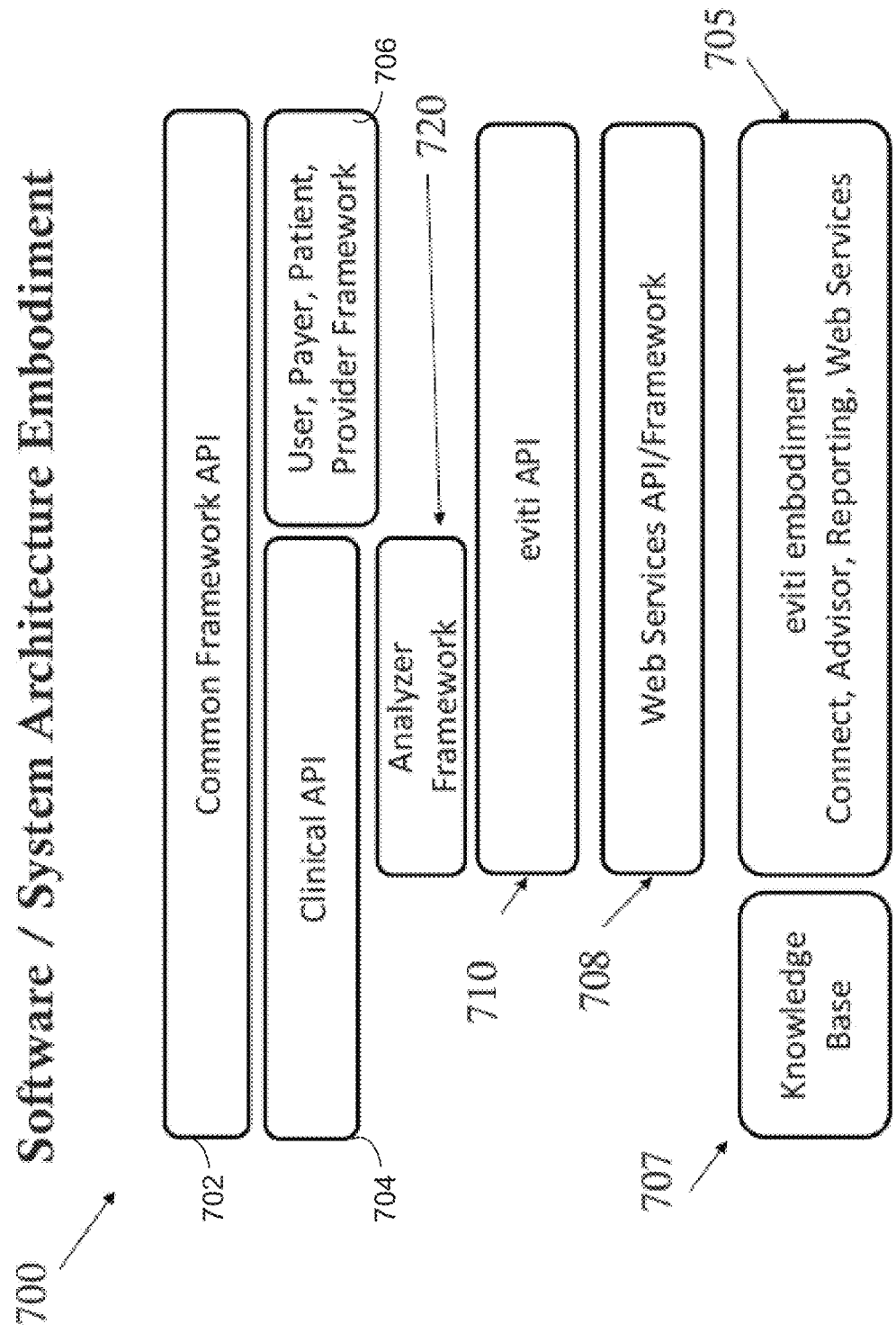
FIG. 10 is an example of a software and system architecture in accordance with an embodiment the invention.

Referring now to FIG. 10, a software and system architecture 700 in accordance with the present disclosure is shown. Software and system architecture 700 may include one or more modules, frameworks, and/or APIs that may be utilized for automating medical data processing and counseling and evidenced-based medicine. For example, architecture 700 may include common framework API 702, and clinical API 704. Architecture 700 may include various branded interfaces and system tools such as provided by eviti or another services provider. Examples of such embodiments, branding with regard to eviti as an example, are the Connect, Advisor, Reporting, and Web Services 705. Architecture 700 may also include user, payer, patient, and provider framework 706. Architecture 700 may further include knowledge base 707, web services API and framework 708, system API 710, and analyzer framework 720. Additional details relating to a system API 710 such as eviti API 710, as an exemplary system API, are shown in FIG. 11E.

Figure 11A:
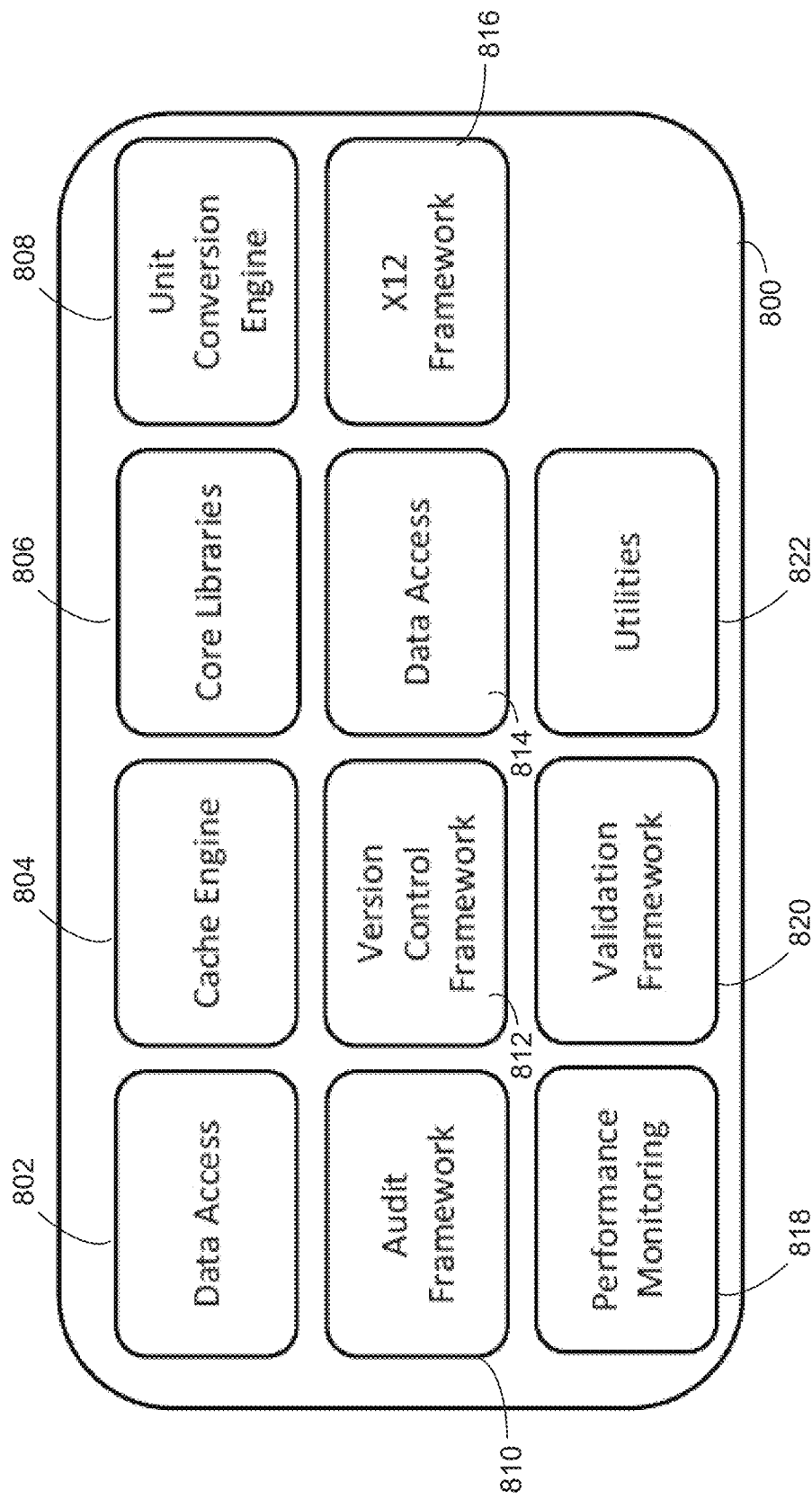

Referring now to FIG. 11A, the common framework API may include one or more modules that may facilitate automating medical data processing and counseling and evidenced-based medicine. For example, common framework 800 may include data access module 802, cache engine 804, core libraries 806, unit conversion engine 808, audit framework 810, version control 812, data access 814, X12 framework 816, performance monitoring 818, validation framework 820, and utilities 822.

Figure 11B:
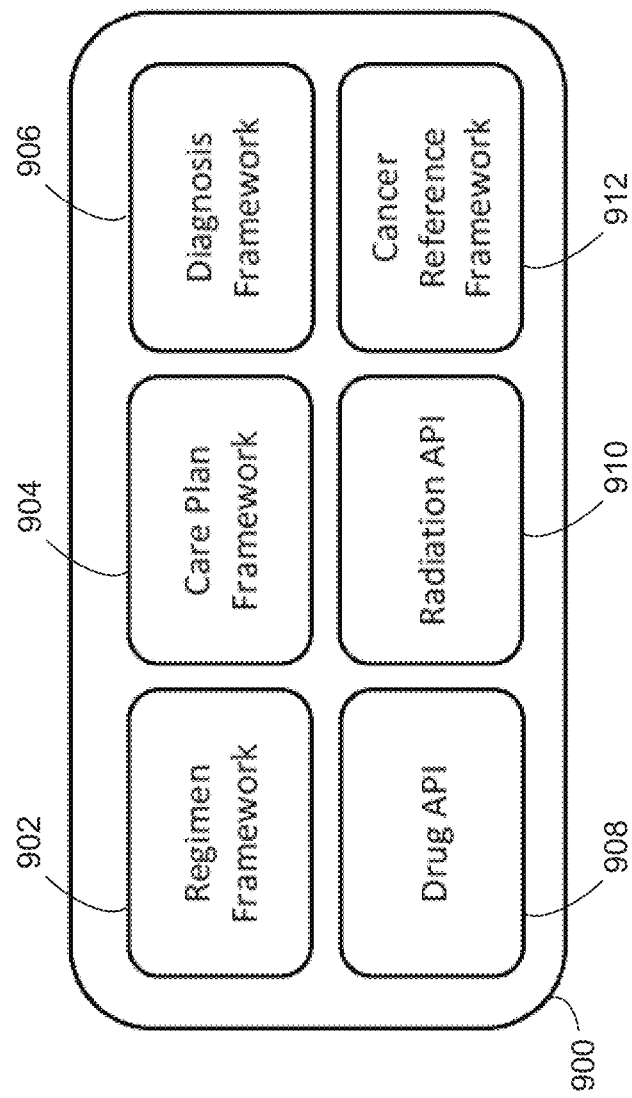

Referring now to FIG. 11B, the clinical API 704 may include one or more modules that may facilitate automating medical data processing and counseling and evidenced-based medicine. For example, clinical API 900 may include regimen framework 902, care plan framework 904, diagnosis framework 906, drug API 908, radiation framework API 910, and cancer reference framework 912.

Figure 11C:
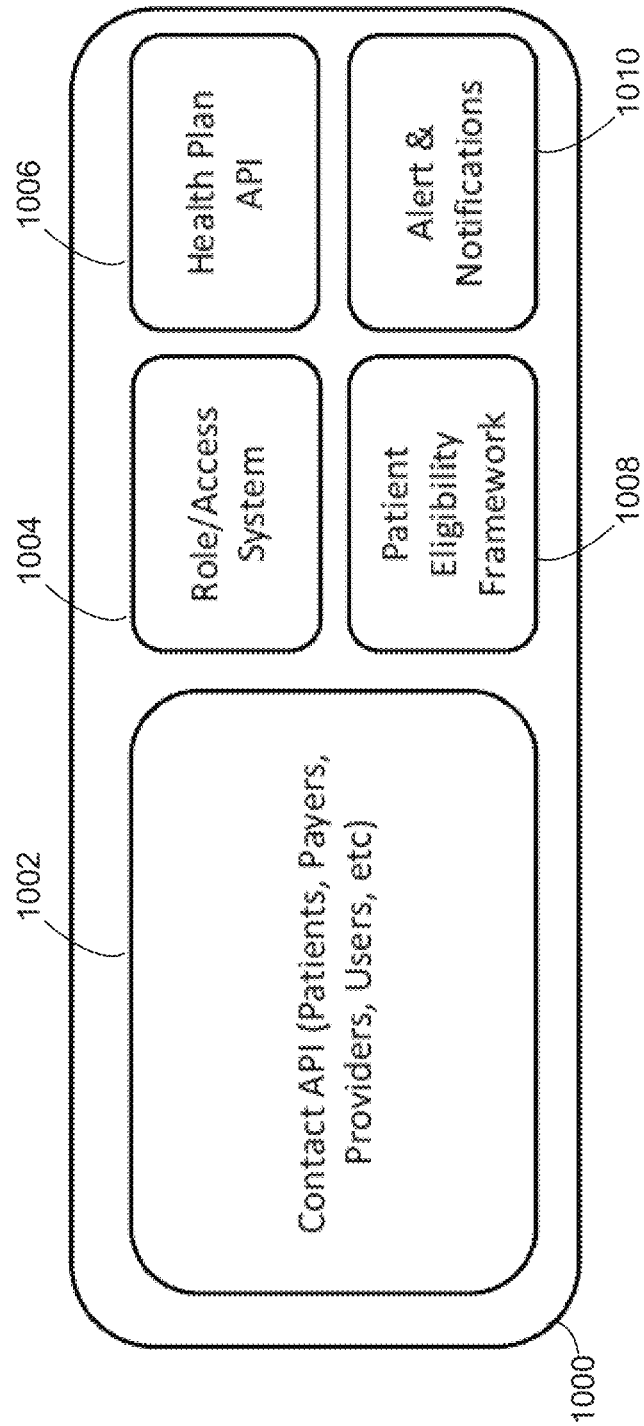

Referring now to FIG. 11C, the user, payer, patient, and provider API 1000 may include one or more modules that may facilitate automating medical data processing and counseling using evidenced-based medicine. For example, user, payer, patient, and provider API 1000 may include contact API 1002, role/access system 1004, health plan API 1006, patient eligibility framework 1008, and alert and notifications framework 1010.

Referring now to FIG. 11F, a regimen may be a series of well-defined treatment requirements and options that have been studied and approved by the medical or cancer community as evidenced-based medicine and may be appropriate for care under given circumstances. In a given system embodiment, such as for example, the eviti system, a regimen may be an object graph that may include treatments from a simple list of drug options, to a very large deep hierarchy of drugs, cycles, radiation, groups of drugs that define the requirements of a regimen. There may be no limit to how deep the hierarchy needs to go to define requirements. An example hierarchy 1300 that may define requirements of a regimen is shown on the left hand side of FIG. 11F.

In one embodiment, the system is configured via the input user interface to receive the treatment options a user has selected for a patient in response to their condition. Thus, a patient with a condition such as cancer is asked to enter drug treatments that are intended to be used as part of a treatment plan for a specific diagnosis (e.g., breast cancer, stage III) relating to a particular condition (e.g., cancer). In one embodiment, the treatment options are selected prior to entering a specific diagnosis. This also for errors to be generated in responses to the treatments selected by analyzing them relative to a subsequently enter diagnosis. After the drugs or other components of the treatment plan are entered, analyzer rules described herein can be used to flag errors based on deviations from evidence-based medicine or payer plan language. Once the errors are corrected, a payer code such as an eviti code can be generated for a given treatment plan for a given diagnosis. Additional details relating to this processor-based method and error flagging is described herein, including with regard to FIG. 12.

A care plan may be a simplified and flattened version of the regimen graph that may represent most or all treatment options available to the doctor. The doctor may select which options to use for the current patient's treatment. If a drug in the regimen shows up more than one time, the system may "merge" the drug. As a result of being merged, the drug only shows up once for the doctor's selection. An example care plan 1302 is shown on the right hand side of FIG. 11F.

An analyzer can include one or more rules engines that may take in and process most if not all types of data in an organized and parallel manner, and may output flags of various types (e.g., error, warning, info, etc.) with information about possible errors, violations, information about the data passed in.

Figure 11D:
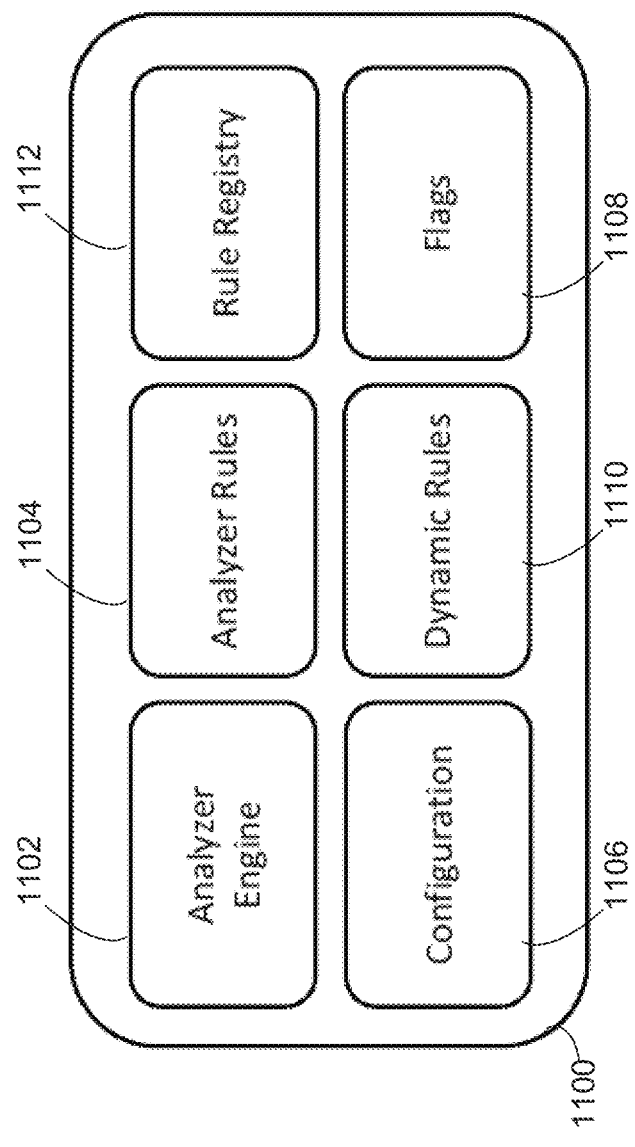
Figure 11E:
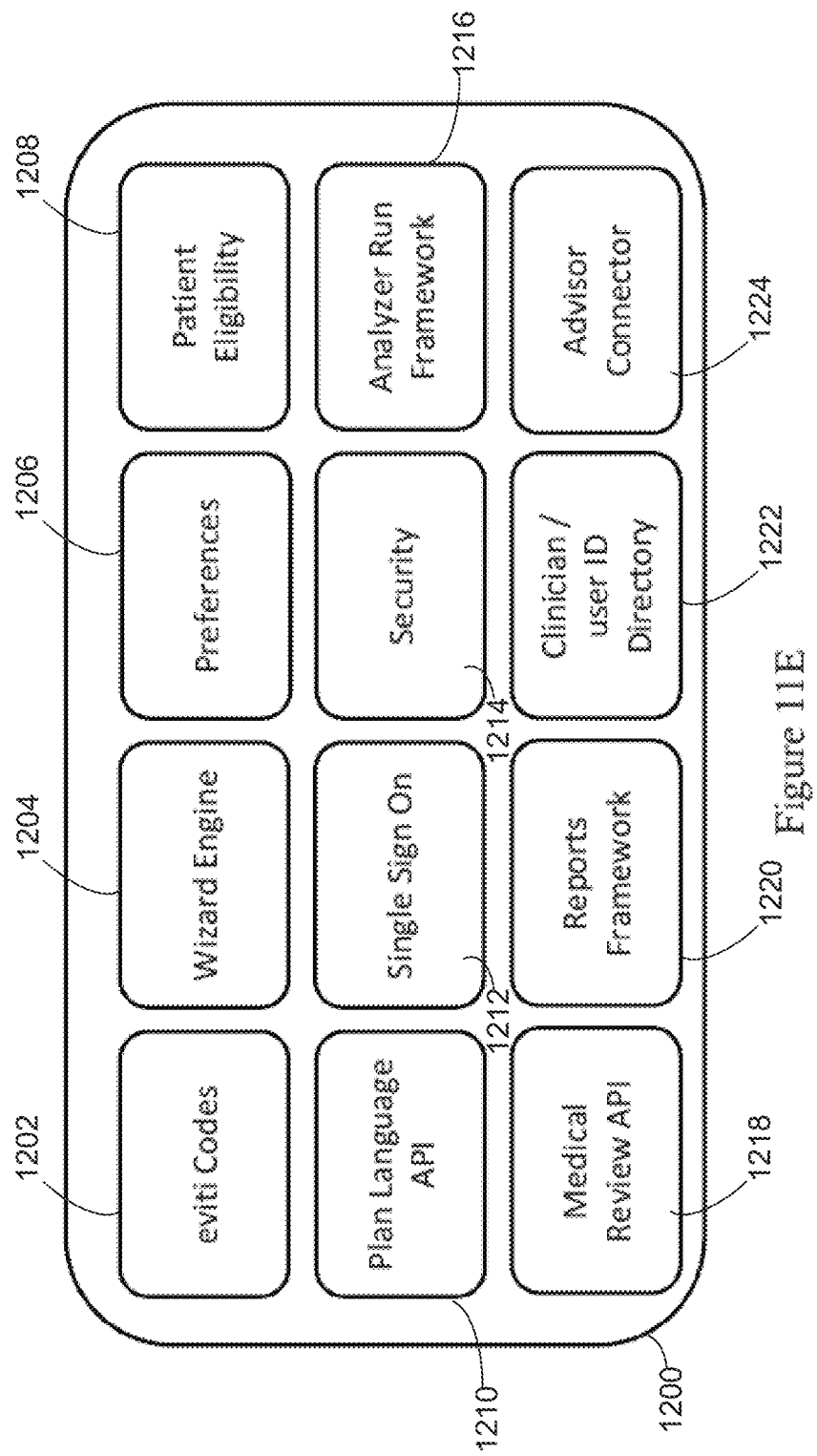

Referring now also to FIG. 11D, an analyzer framework in accordance with the present disclosure is shown. The analyzer framework may include one or more modules that may facilitate automating medical data processing and counseling and evidenced-based medicine.

The analyzer may be analyzer module 1100 and may include of various components that make up the analyzer. The components and rules of analyzer module 1100 may be based on evidence-based medicine criteria and payer plan language. Analyzer module 1100 may be configured to compare a treatment plan for a diagnosis with evidence based medicine criteria corresponding to the diagnosis and a given payer's plan requirements or language. For example, analyzer rule module 1104 may include analyzer rules, which may be definable and/or codable components where a business rule may be defined and in which any violations of this rule may be flagged. Analyzer rules may be customizable and may take in any kind of data to process or analyze. An analyzer rule may take in any data required via a parameter list. A given drug may not be in compliance with evidence based medicine for a particular diagnosis. This can be an example where a flag would be generated based on a rule violation. Similar violations of payer plan terms can also be used.

Further, an analyzer rule may have a list of flags that are associated with the rule. The analyzer rule may be, and in some cases is required to be defined in advance, and any flags that might be used as violations. Flags module 1108 may include one or more flags. The one or more flags may be associated with the one or more analyzer rules and may utilize one or more predefined error codes each having a unique code associated with an evidence based medicine criteria violation. Flags may be data driven, utilizing predefined error codes which may enable the flag text to be customizable with a user interface after compilation. Each error code may have a unique code that may be associated with a particular violation. This may enable easy searching and identification of errors.

Figure 11G:
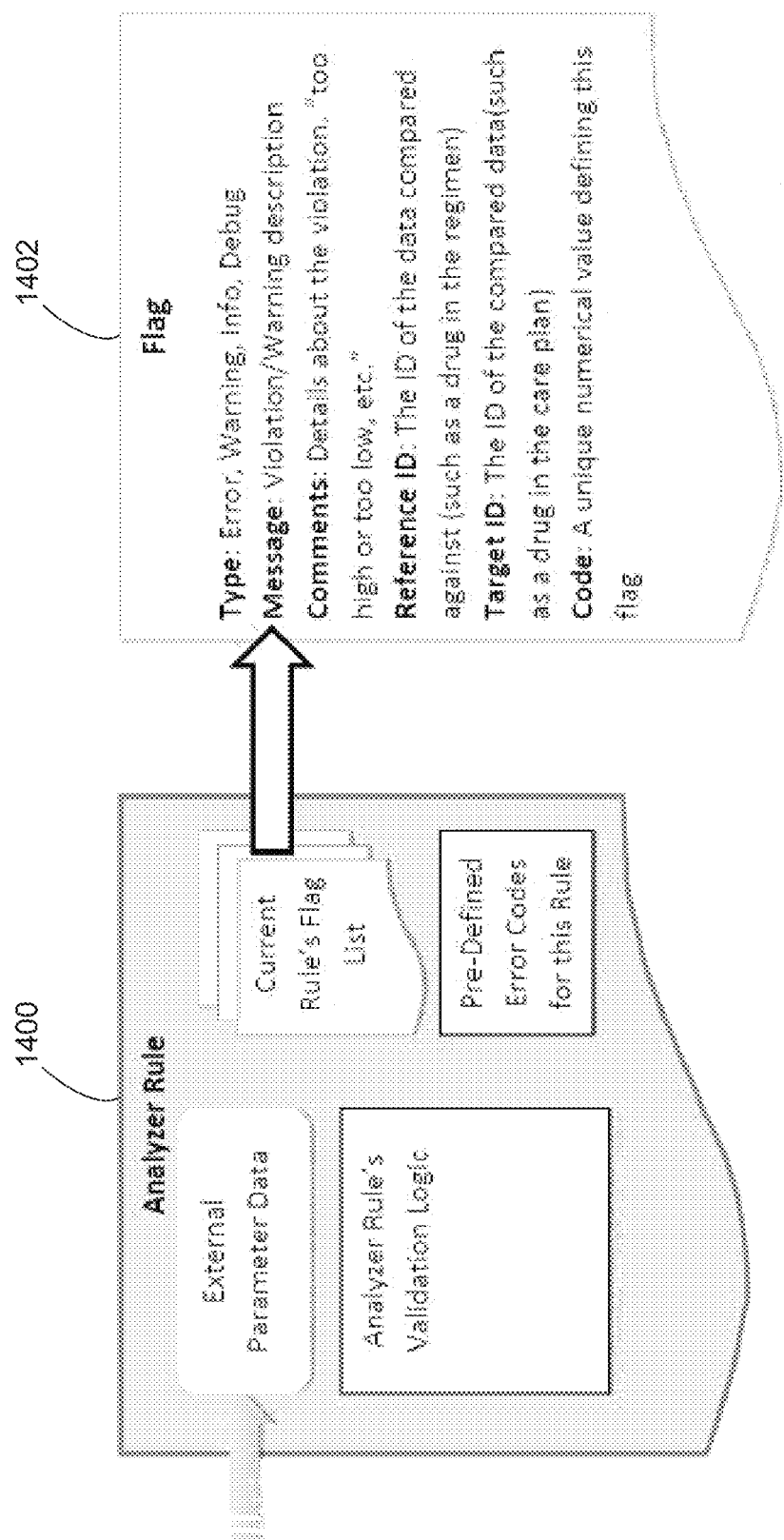

Analyzer rules module 1104 may include the one or more analyzer rules configured to run. The one or more analyzer rules may be associated with one or more flags. The one or more flags may be associated with one or more violations of the evidence based medicine criteria. Referring now to FIG. 11G, an example of an analyzer rule 1400 and an example of a flag 1402 in accordance with the present disclosure are shown, and various components of analyzer rule 1400 are also shown. For example, analyzer rule 1400 may include external parameter data, validation logic, a flag list, and error codes. Flag 1402 may include a flag type, a message describing the violation, comments on the violation, a reference ID, and a target ID. The reference ID may be related to the ID of the data compared against (e.g., a drug in the regimen). Further, the target ID may be the ID of the compared data (e.g., a drug in the care plan).

Analyzer rules may not be aware of other analyzer rules or the analyzer engine, which may allow for parallel processing. Further, analyzer rules may be customized for certain objects, in preparation for more specific analyzer rules (i.e., reusability). Examples include a care plan analyzer which may include setup logic such as a base analyzer, a property analyzer which may analyzer properties of a care plan, and a container requirements analyzer, which may analyze drugs and groups.

Figure 11H:
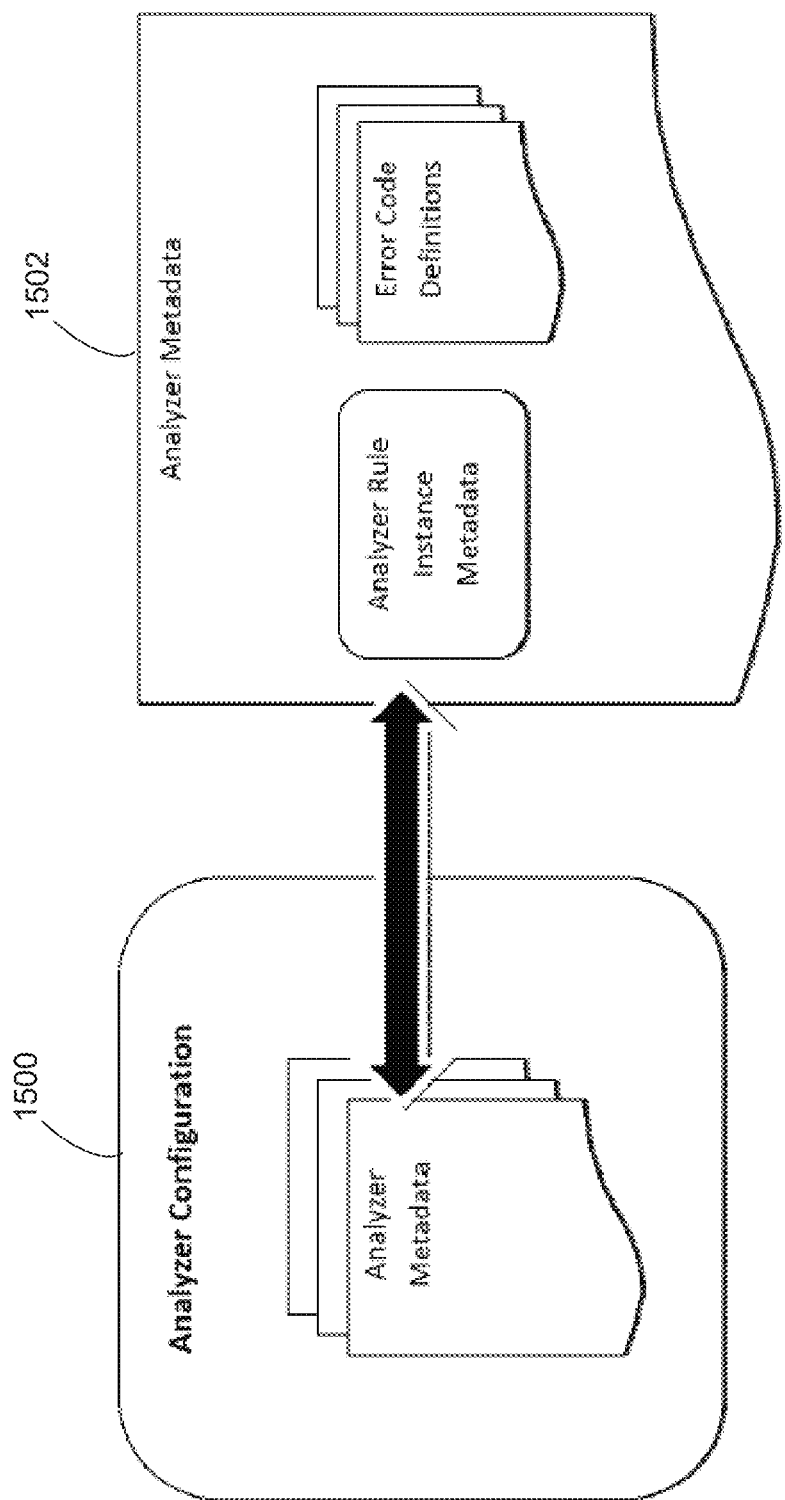

Analyzer configuration module 1106 may be configured to communicate the configuration to analyzer engine 1102. Analyzer configuration module 1106 may include data representing (e.g., metadata) which analyzer rules from the analyzer rules module to run for an analyzer engine instance. Analyzer configuration and metadata may include information about a series of analyzer rules to run along and which order, if applicable for a current analyzer engine's instance. Analyzer metadata may be information about analyzer rules such as IDs and any associated error codes that may be utilized by the rule. Analyzer configuration may be a container for analyzer metadata, and may group metadata to inform the analyzer engine on which rules to load & run. Referring now to FIG. 11H, an example analyzer configuration 1500 and metadata 1502 in accordance with the present disclosure are shown.

Figure 11I:
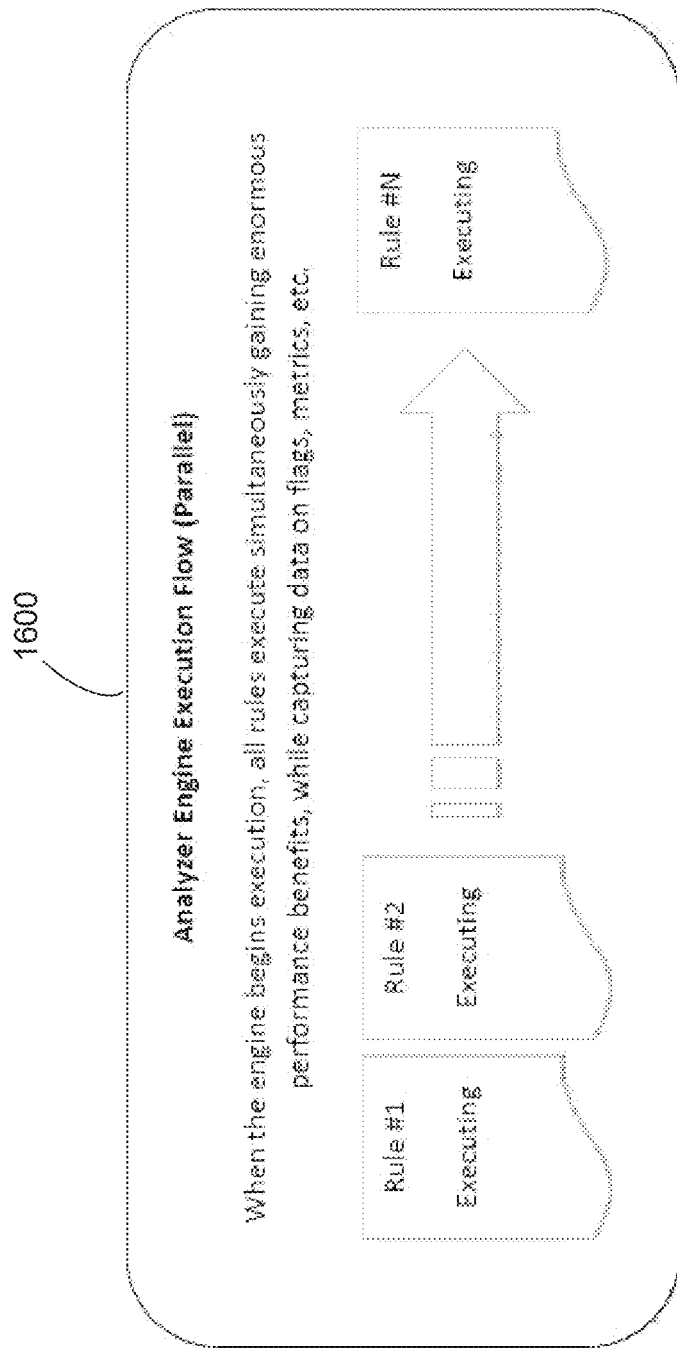

Analyzer engine 1102 may be configured to receive a configuration from analyzer configuration module 1106. Analyzer engine 1102 may be further configured to run one or more analyzer rules in parallel based upon the configuration. The one or more analyzer rules may be associated with the evidence based medicine criteria. Analyzer engine 1102 may be the core and executer of the analyzer system. The engine may take in a configuration which may instruct the engine on which analyzer rules to load and prepare for processing. Once loaded, the analyzer may run each analyzer rule in parallel. Referring now to FIG. 11I, an example analyzer engine execution flow 1600 in accordance with the present disclosure is shown.

While each rule is running, each analyzer rule's flag list may grow based on the rules logic. Analyzer engine 1102 may be further configured to transfer analyzer data associated with the one or more flags associated with the one or more analyzer rules to a master flag list. The master flag list may include the flags occurring during an analyzer execution run. The flags may occur based on evidence based medicine criteria violations. At the end of processing, the engine may transfer each analyzer flag data over to the engines master flag list. This list now may include all flags based on all analyzers that have run. Metrics on the analyzer rules performance may be gathered as well.

Analyzer module 1100 may be further configured to store an analyzer run including data representative of the configuration used during an analyzer engine execution run. Each engine execution run and its results may be stored in what may be called "analyzer run". The information stored may be based on the configuration used, date/time, duration of run, which parameters/data were used and tied to patients, and/or number of flags generated. Data may also be captured on each analyzer itself, duration, and flags generated. The actual flag data captured during the run may be stored and tied to the "analyzer run" data. This data allows us to run reports on what errors occurred and why they occurred. The flag data also allows report to be in aggregate based on the unique error codes that may allow reports such as percentage of failures over time, or other reports to users of the system and to eviti administrators. Analyzer module 1100 may also include rule registry module 1112 and dynamic rule module 1110.

Referring now to FIG. 11E, the eviti API 1200 may include one or more modules that may facilitate automating medical data processing and counseling and evidenced-based medicine. Again, references to eviti are exemplary and can be replaced with the name of the service providing offering one or more of the evidence-based method software tools described herein. For example, eviti API 1000 may include eviti codes module 1202, wizard engine 1204, preferences module 1206, patient eligibility module 1208, plan language API 1210, single sign on module 1212, security module 1214, analyzer run framework 1216, medical review API 1218, reports framework 1220, clinician user IP directory 1222, and advisor connector 1224. In one embodiment, an eviti code is generated to indicate compliance with evidence-based medicine and payer plan language for a particular output such as a treatment plan.

In an embodiment in accordance with the present disclosure, one or more processes, methods, and systems may facilitate automating medical data processing and counseling and the practice of evidence based medicine. In some systems, a user may enter a specific treatment and/or regimen that deviates from known evidence based treatment. In these situations, the system may be unable to match the treatment and/or regimen to a particular diagnosis. As such, information entered into the system may be difficult for a care processor to handle.

Figure 12:
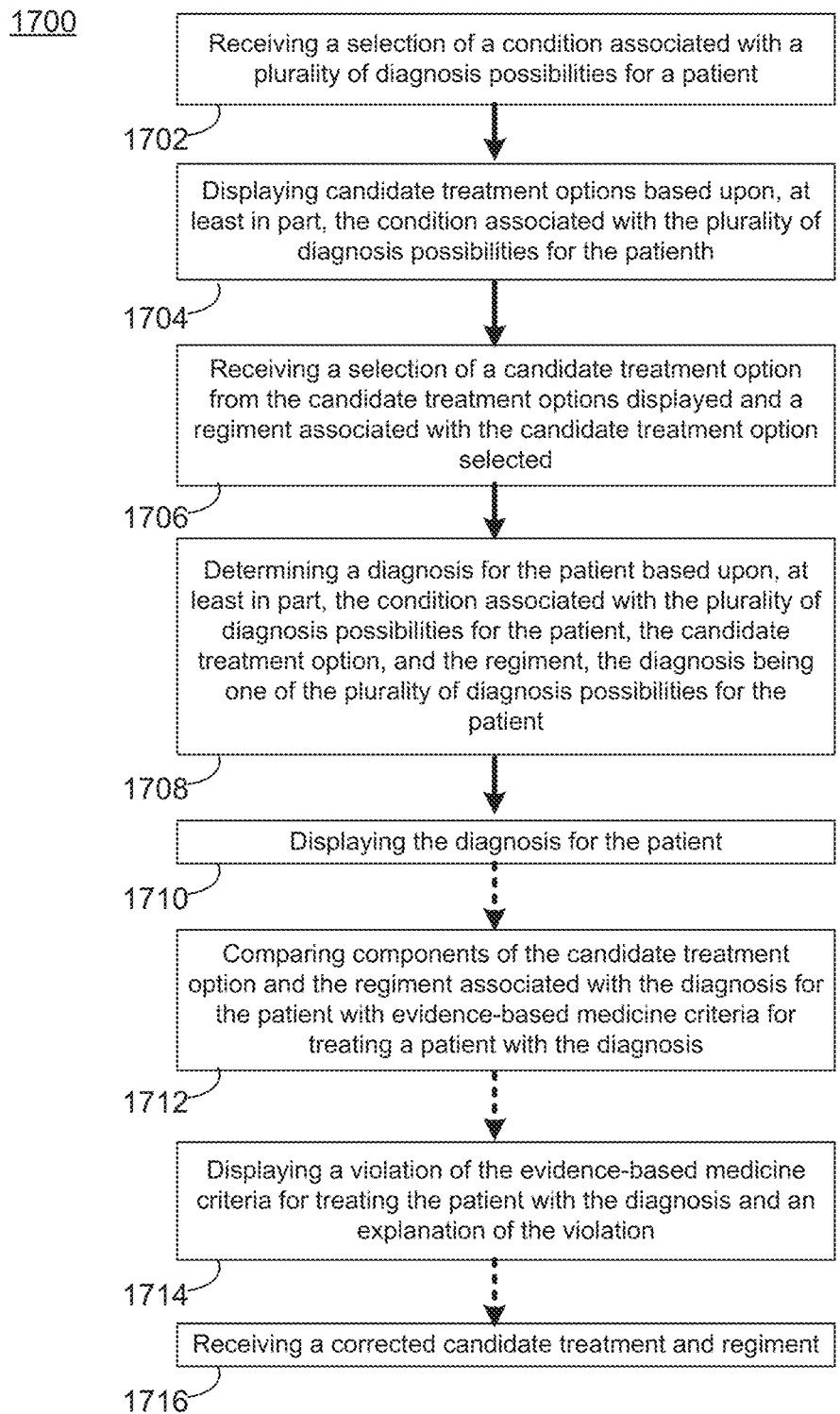
FIG. 12 is an example process flow in accordance with an embodiment the invention.

Referring now to FIG. 12 a process 1700 may be configured to receive 1702 a selection of a condition associated with a plurality of diagnosis possibilities for a patient.

Process 1700 may display 1704 candidate treatment options based upon, at least in part, the condition associated with the plurality of diagnosis possibilities for the patient. Further, process 1700 may receive 1706 a selection of a candidate treatment option from the candidate treatment options displayed and a regimen associated with the candidate treatment option selected. Additionally, process 1700 may determine 1708 a diagnosis for the patient based upon, at least in part, the condition associated with the plurality of diagnosis possibilities for the patient, the candidate treatment option, and the regimen. The diagnosis may be one of the plurality of diagnosis possibilities for the patient. Process 1700 may display 1710 the diagnosis for the patient.

In an embodiment, process 1700 may compare 1712 components of the candidate treatment option and the regimen associated with the diagnosis for the patient with evidence-based medicine criteria for treating a patient with the diagnosis. Process 1700 may also display 1714 a violation of the evidence-based medicine criteria for treating the patient with the diagnosis and an explanation of the violation. Further, process 1700 may receive 1716 a corrected candidate treatment and regime[0001] n. In an embodiment, process 1700 may compare 1712 components of the candidate treatment option and the regimen associated with the diagnosis for the patient with payer plan language to identify deviations therefrom or compliance therewith.

In an implementation, process 1700 may generate an evidence-based medicine treatment plan for the patient. The evidence-based medicine treatment plan may be consistent with payment guidelines of a payer and may be generated in response to receiving the corrected candidate treatment and regimen. Further, process 1700 may generate a treatment plan code. The treatment plan code may be associated with the evidence-based medicine treatment plan generated for the patient. The treatment plan code may be unique and specific to the patient and the evidence-based medicine treatment plan. An eviti code is an example of such a treatment plan code.

In an implementation, comparing the components of the candidate treatment option and the regimen associated with the diagnosis for the patient with the evidence-based medicine criteria for treating the patient with the diagnosis may further include comparing granular deviations of the candidate treatment option and the regimen associated with the diagnosis for the patient with the evidence-based medicine criteria. For example, process 1200 may compare at least one of a dose, a treatment cycle, a drug, and a drug group associated with the candidate treatment option and the regimen associated with the diagnosis for the patient with a corresponding dose, treatment cycle, drug, or drug group associated with the evidence-based medicine criteria.

Since embodiments of the invention, relate in part, to displaying guidance, data, or other items of interest using an electronic representation, such as an on-screen depiction, email, or other electronic delivery means, various screenshots relating to different subsystem are described below. These figures include point and click and drop down interface elements in one embodiment. Although in some of the illustrative embodiments described below cancer is identified as a disease state with much of the underlying interface screen containing cancer specific options, the embodiments described herein are extendible to any disease state or patient condition.

Figures 3D, 3E:
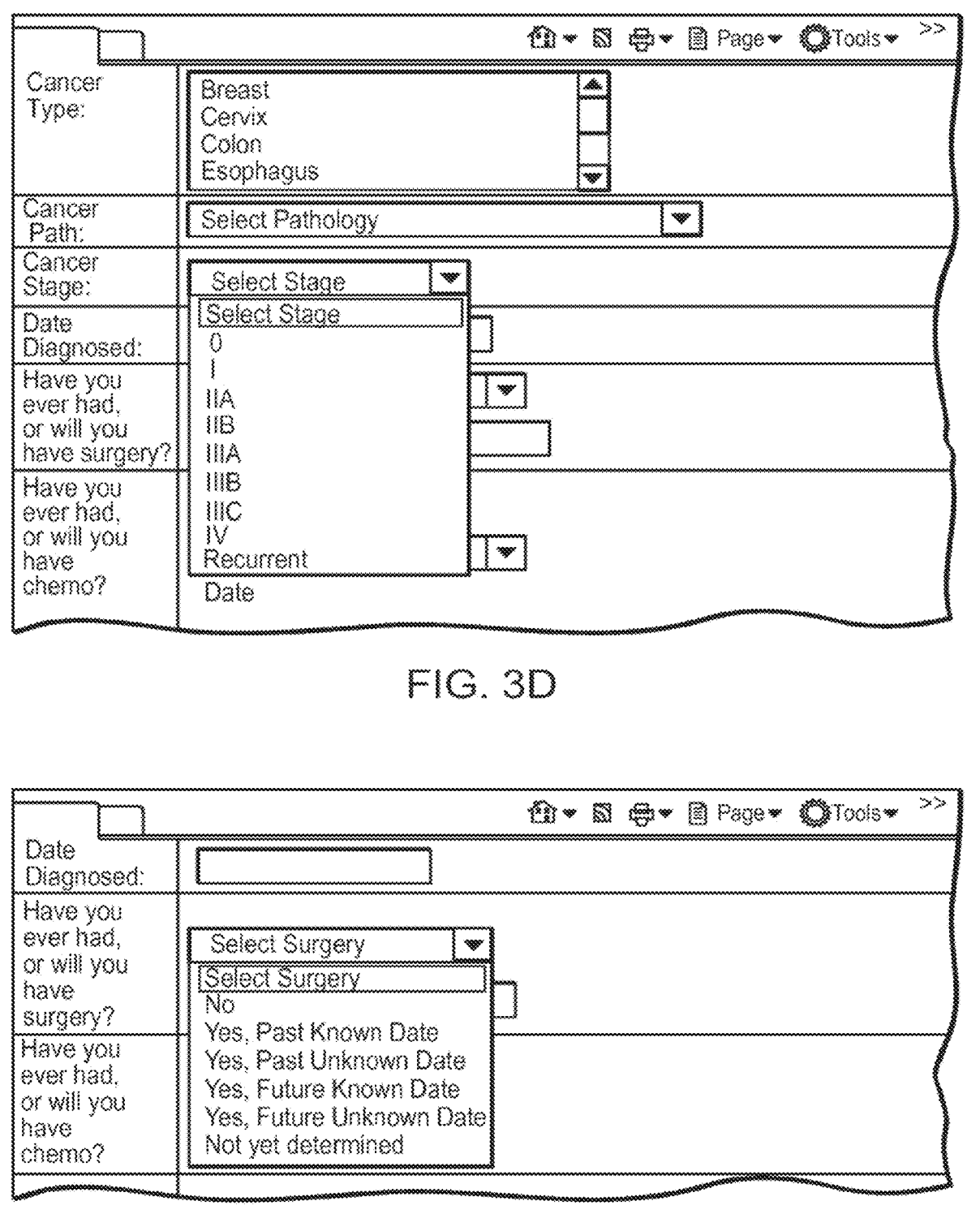

Specifically, in FIGS. 3A-3I various on-screen interfaces or information displays relating to the process of enrolling a patient in an automated system to facilitate medical decision making and risk analysis are shown. In FIG. 3A, various cells for entering patient data, such as patient demographic data, are part of the on-screen interface. FIGS. 3B and 3C show an on-screen interface suitable for entering specific medical information, such as cancer related information, for a given patient suffering with the disease. FIGS. 3D-3I include additional interface screens suitable for capturing and transmitting various disease, drug, and treatment relate patient data to a database.

FIGS. 4A-4B are a series of on-screen representations relating to task generation in an automated medical data processing and counseling system in accordance with an embodiment of the invention. As part of the case management functions of the systems and methods described herein in FIG. 4A, various tasks associated with a given patient are shown. Similarly, action items that need to be addressed with the client to assist with their treatment are shown in FIG. 4B.

Figure 5A:
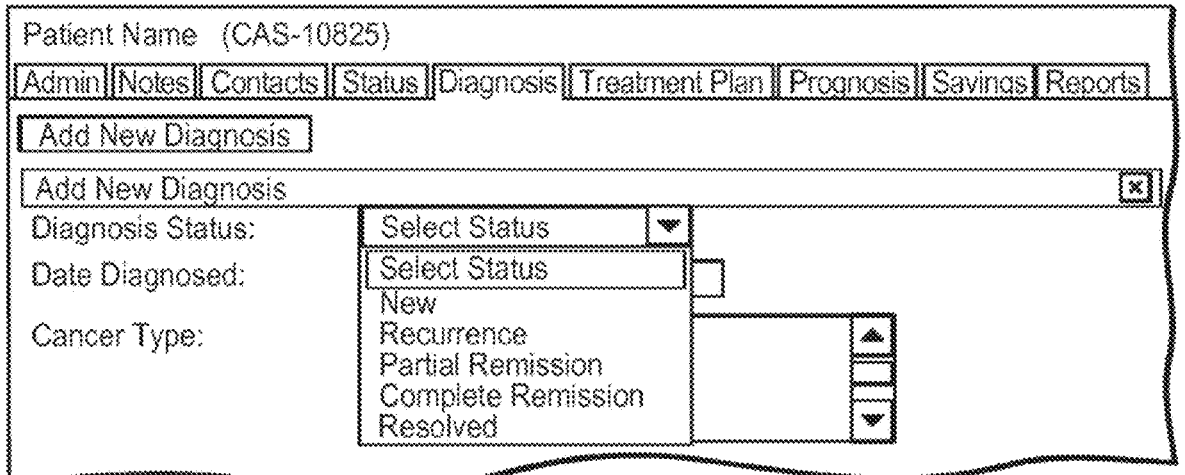
Figure 5B:
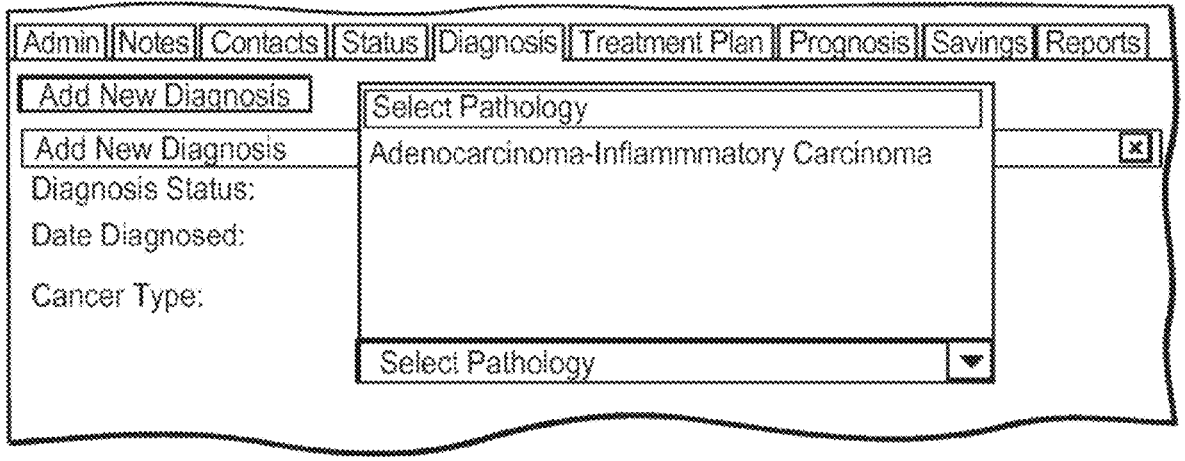
Figure 5C:
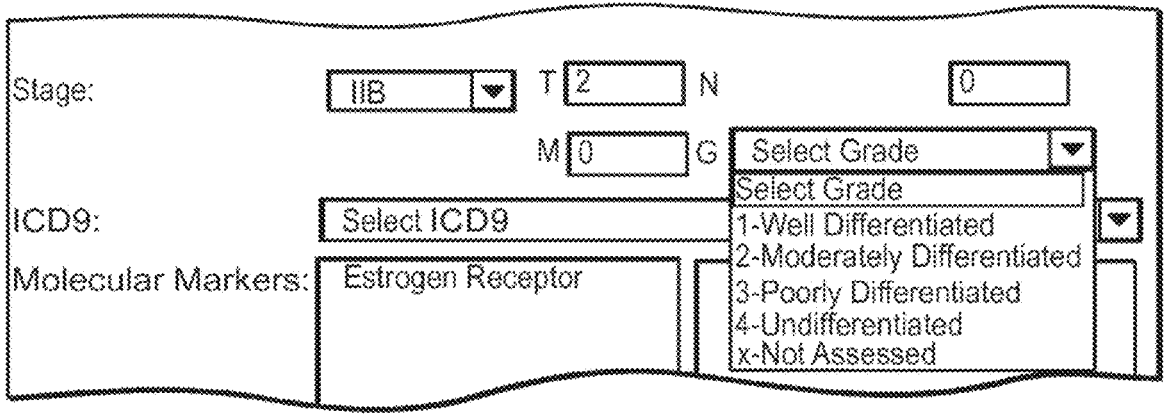

FIGS. 5A-5E are a series of on-screen representations relating to a diagnosis process flow in an automated medical data processing and counseling system in accordance with an embodiment of the invention. Specifically in these figures, interfaces showing information relating to diagnosing a specific disease type (in the example shown it is a cancer diagnosis). FIG. 5A shows a tab-based interface screen with the Diagnosis tab shown as active. This diagnosis process flow is suitable for collecting diagnosis information or diagnosis parameters relative to a patient that has a condition. In turn, this information can be used in conjunction with payer plan language encoded in a database and the evidence-based treatment options discussed herein to generate a patient specific treatment guidelines and a plan code as discussed in more detail below with respect to FIGS. 7A-9M.

The other tabs (not shown) include an admin tab, a notes tab, a status tab, a savings tab, and a reports tab. The admin tab includes general patient administrative information which can include client, primary risk management personnel (such as their nurse) contact information and health plan information. The notes tab includes a collection of uploaded files to be stored as part of the risk management process. Notes can include referral documents, release of medical records documents, medical documents, plan documents, and any other computer storable file type. The status tab includes a date record collection of the patient's progression through the risk management process, i.e. date referred, date enrolled, and date discharged. The savings tab includes a tab collecting all cost savings earned through the risk management process. The reports tab collects risk management reports generated for the patient. In some embodiments, these tabs include more or less information than discussed above.

As a patient is diagnosed, a care provider or other system user can input various diagnosis related information using the on-screen interfaces of FIGS. 5A-5E. In turn, the knowledge base, and analysis functions of the various systems and methods described herein can use the diagnosis information to populate a treatment plan, or generate other on-screen guidance for a system user.

Figures 6C, 6D:
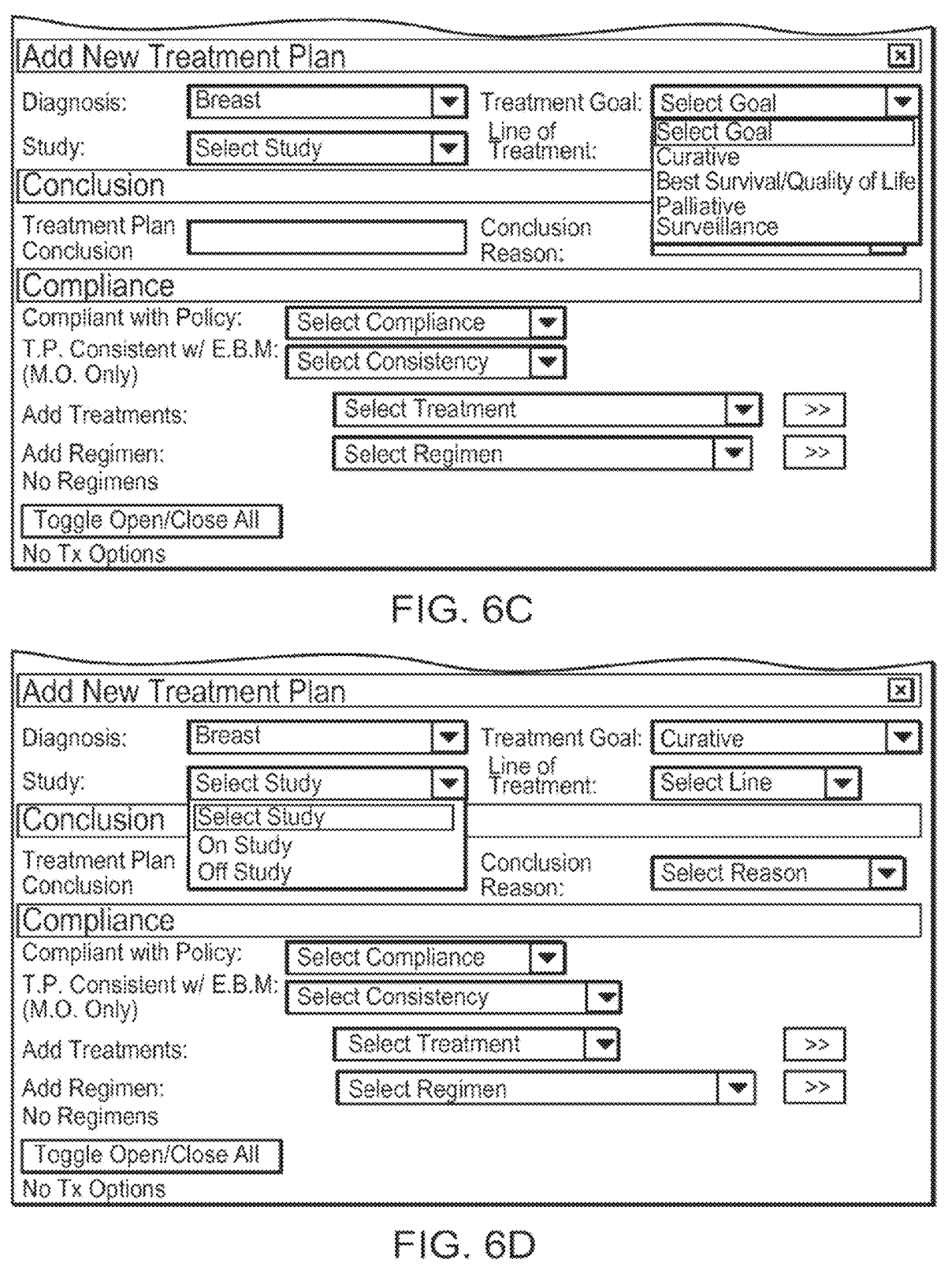
Figures 6E, 6F:
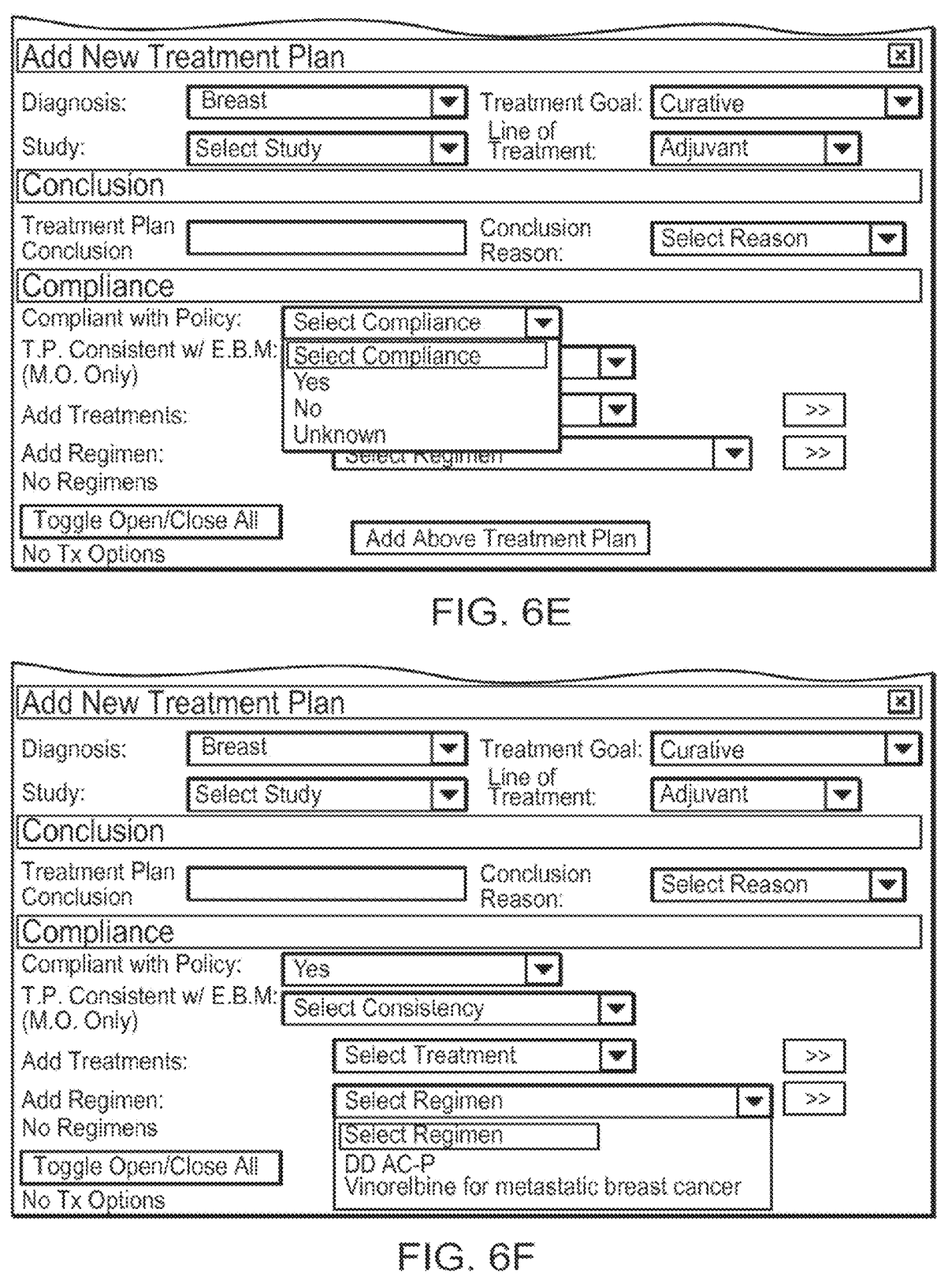

FIGS. 6A-6G are a series of on-screen representations relating to a computer-based treatment plan as implemented in an automated medical data processing and counseling system in accordance with an embodiment of the invention. FIG. 6A shows the initial screen for adding a new treatment plan. In some embodiments, the treatment plan is automatically generated with the option of modification by the user in response to the diagnosis information input with respect to particular patient. FIGS. 6B-6E show different information being added with respect to a particular treatment plan.

Of note, each on-screen interface includes a "compliant with policy" drop down menu. During circumstances wherein the treatment plan is non-compliant with a given policy, the automated medical counseling system can generate a comparison with a given policy (using the comparator described above in one embodiment) and forecast the benefits of selecting a non-compliant plan as discussed above. Under certain circumstances, selecting a non-compliant treatment plan is in the best interest of the patient and the insurance provider.

In order to model future risk exposure, the system uses a combination of neural networks, Markov chains and a simulation populated with known clinical statistics, in one embodiment. In general any computer based approach to estimate (1) future disease progression/co-morbidities, or (2) correlated costs with respect to known current diagnosis that is based on current diagnosis and treatment can be used.

In one specific embodiment, the automated systems and related data processing techniques can be used to model future exposure based upon diagnosis data, treatment data, and prognosis data. In part, using such a system and historic data, it is possible to demonstrate scenarios in which initially establishing the correct treatment plan, even if it includes recommendations that are non-compliant with an existing plan, result in long term benefits relative to a scenario if the compliant treatment plan was followed.

EXAMPLE

In one specific example of exposure modeling, a patient is a 61 year old male, with limited stage, small cell lung cancer. The patient receives chemo/radiation therapy, concurrently. Further, based on the chemo/radiation therapy treatment, the patient has the following probabilities of future costs: (Disease Progression=60% with an Estimated cost of progression=$33,000). In this example the disease progression rate associated with a first treatment is about 0.60.

The patient's doctor has the option of giving an additional follow on treatment after chemo/radiation therapy, which has the following outcomes and associated probabilities: Progression=about 33%. In this example the disease progression rate associated with a second treatment (the follow on treatment) is about 0.33. This is cumulative to the chemo/radiation therapy probabilities, changing the overall outcome/probability as follows: Progression=about 60%× about 33%=approximately 20%. In this example the combined diseases progression rate associated with a combination treatment is about 0.20.

The automated system and methods described herein can use this data to perform simplified or complex models relating to expected exposure calculations. Without follow on treatment the expected cost=0.6×$33,000=about $20,000. This is the product of the first disease progression rate with a first estimated cost of progression. However, other functional relationships with weights and other parameters can be used. In contrast, with follow on treatment the expected cost=0.2×$33,000=about $6500. This is the product of the combined diseases progression rate with a first estimated cost of progression. As a result, using this future exposure model, the expected value of the follow on treatment is about $13,500 (or the difference of $20,000 and $6,500).

These models can be implemented using various APIs and other software modules as discussed throughout. In general, the data used to populate these models is taken from the databases discussed herein or entered by a system user.

Evidence-Based Medicine and Payer Plan Language Compliant Treatment Plan Embodiments As mentioned above, various embodiments of the invention relate to automated generation of treatment plans that comply with evidence-based medicine guidelines and also satisfy the plan language requirements of a payer. A schematic diagram illustrating a system 190 that uses programming logic such as software modules to instruct a processor is shown in FIG. 7A.

Figure 7A:
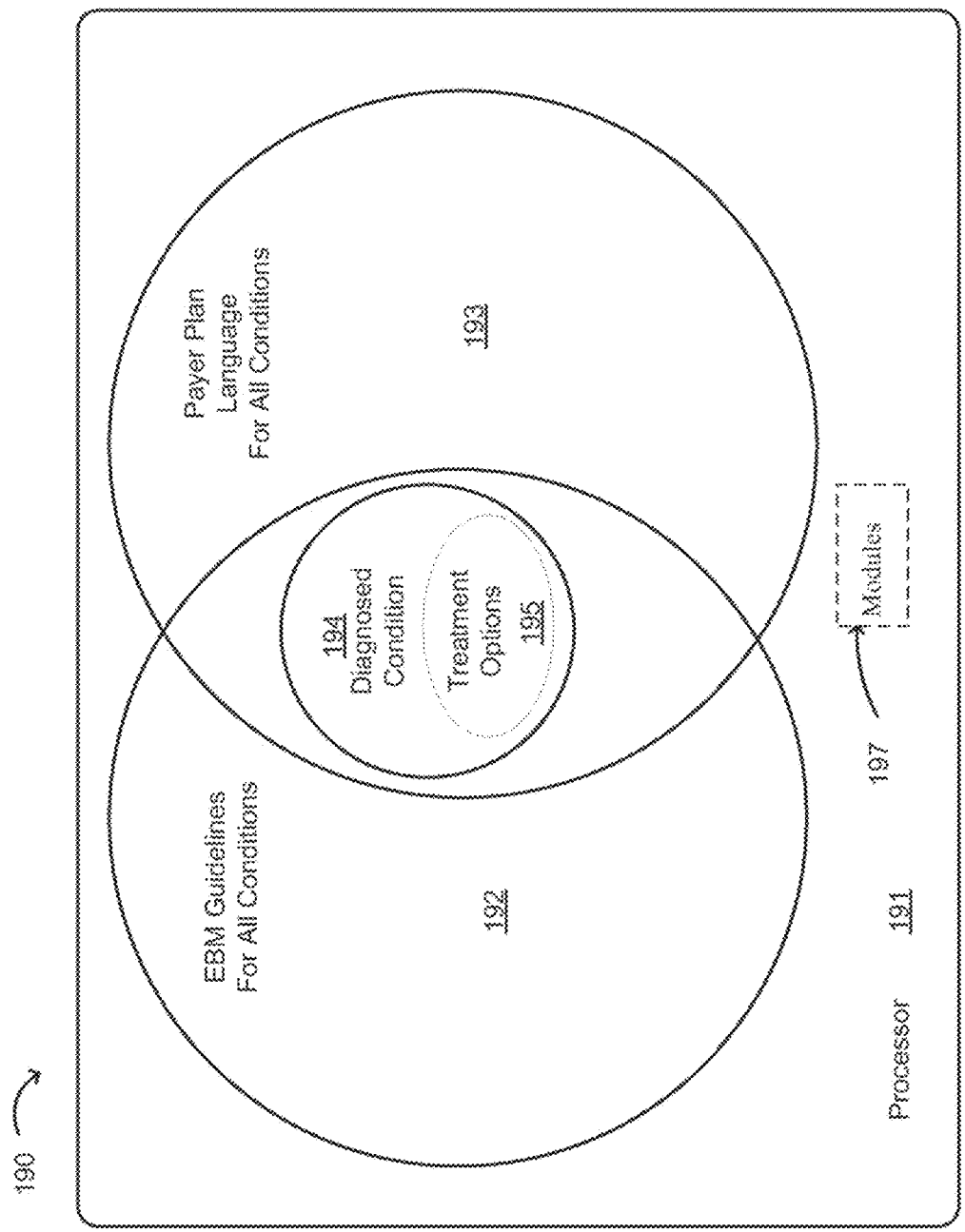
FIG. 7A is a schematic diagram of a processor-based system that is programmed to perform a query and filter different categories of information, in accordance with an embodiment of the invention.

In FIG. 7A, a system 190 for performing logical analysis and queries using a database (not shown) and an electronic processor 191 is shown. The processor shown in FIG. 7A can be part of a computer system that includes an electronic memory device with the electronic processor in communication with the memory device. In turn, in one embodiment, the memory device includes instructions that when executed by the processor cause the processor to display fields and receive patient diagnosis information and treatment options, and generate a treatment plan constructed in response to the diagnosis information and the treatment options.

In further detail, such a system 190 can be used as part of a client server based system as discussed above with respect to FIG. 1A. In FIG. 7A, the processor 191 is programmed with certain modules or logic to query one or more databases and filter the results based upon a particular criteria or constraint. Typically, the processor is programmed to query a set of evidence-based medicine guidelines 192 and a set of payer plan language portions or guidelines 193 based on the diagnosis information 194 associated with a patient. As a result, the intersection of the evidence-based medicine guidelines 192 relative to the set of payer plan language 193 is determined and further filtered with respect to a set of medical-condition specific treatment options 194,195 that satisfy the conditions of both sets 192, 193.

In one embodiment, a medical services provider may further select from the set of candidate treatment options 194 and select a subset of treatment options 195 such that a system module can generate a treatment plan. In one embodiment, the subset of treatment medical condition specific options 194 and the subset of selected treatment options 195 are the same. In addition, with respect to FIG. 7A, various software modules 197 suitable for processing data and generating a treatment plan and auxiliary features relating thereto can be implemented. These modules 197 can include, but are not limited to those described herein and with respect to FIG. 8A.

With respect to FIG. 7A, as an example, the evidence-based medicine guidelines can relate to various medical conditions, such as oncological conditions, cardiac related conditions, renal related conditions, neurological conditions, etc. Similarly, the payer plan language portions such as guidelines and definitions that specify which types of treatments will be settled when presented to the payer can include definitions, rules, business logic, thresholds, contractual language that has been converted to logical operations, and other types of transformed or converted payer plan language. In one embodiment, the intersection of these two sets of guidelines is constrained to be medical condition specific, once a patient diagnosis is made. Further, since certain treatment options recite specific details such as dosage ranges, delivery times, etc., the set of possible candidate options can be further limited by selections made by a medical services provider using a user interface.

Although the filtering of the various sets of information depicted in FIG. 7A is described as being processed in a particular order, it is not necessary to limit the manner in which a set of treatment options is generated based on time steps or sequential ordering relative to the querying or filtering of sets (or subsets) 192, 193, 194, and 195. Thus, in one embodiment, the various sets of information and guidelines can be stored and indexed in the same database and accessed using a local or remote query interface. As a result, the query can be performed simultaneously or at different points in time among various tables in the database relating to the various sets of information depicted in FIG. 7A.

Figure 7B:
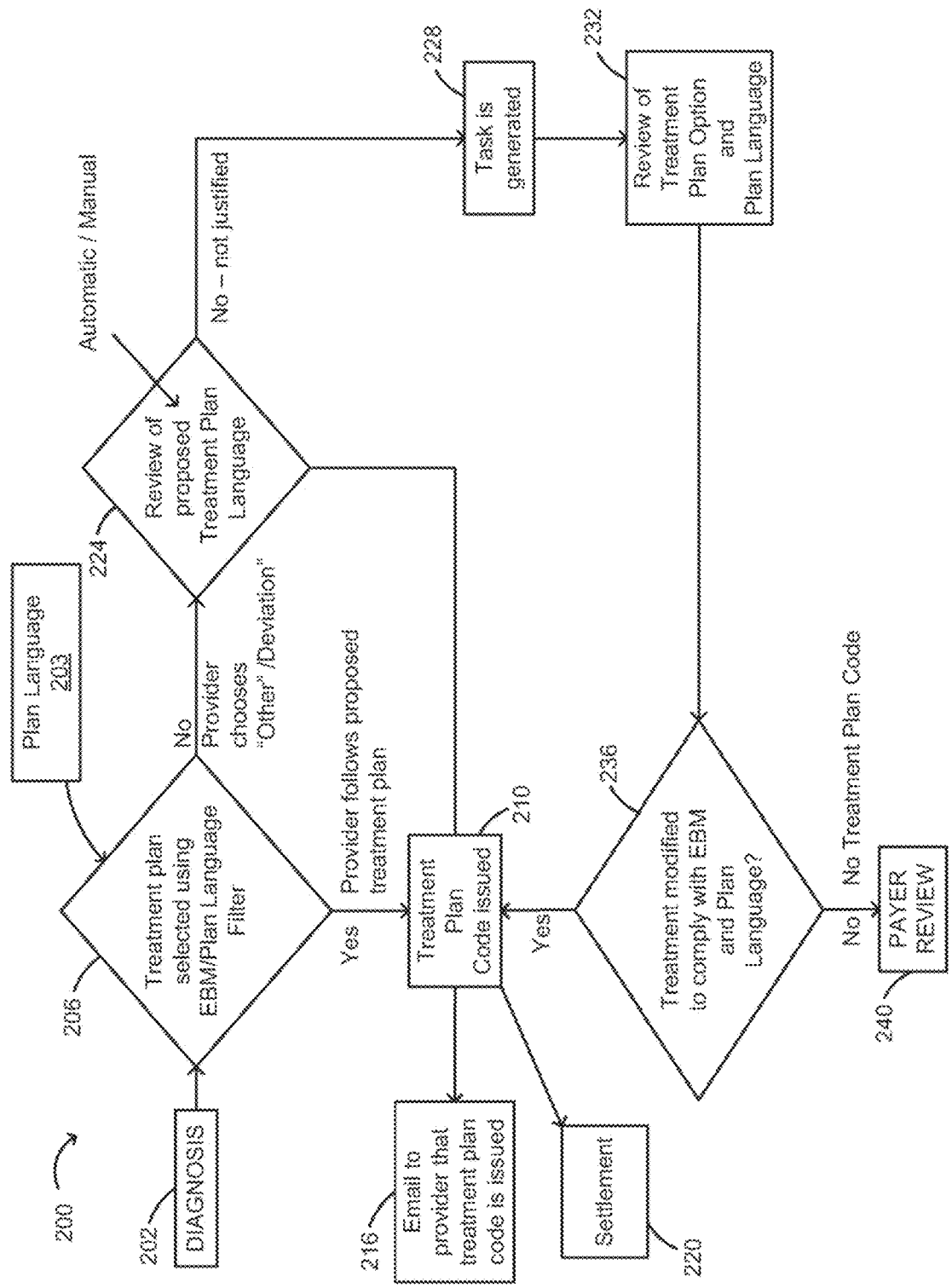
FIG. 7B is a process flow depicting various steps for generating a treatment plan, in accordance with an embodiment of the invention.

FIG. 7B shows a process flow embodiment of a system 200 suitable for generating treatment plans. In one embodiment, the program logic referenced with respect to FIG. 7A is used. In contrast with some of the other embodiments described herein a medical services provider, such as doctor, nurse, technician, etc., enters information relating to a patient using an interface that is part of the overall system 200. In one embodiment, the automated systems and methods described herein determine patient eligibility for processing using the system 200. If the patient is eligible, the interface can be used to collect diagnosis information during the diagnosis stage 202.

As mentioned above, the system depicted 200 in FIG. 7B describes various steps and stages that facilitate treatment plan creation such that the resultant plan satisfies or complies with multiple conditions, requirements, logical relationships or constraints. Specifically, the conditions of interest include, but are not limited to, complying with evidence-based medicine guidelines; complying with the payment requirements of a payer, such as payer plan language; and selection of: filtered treatment options by a provider, diagnosed medical condition of patient, patient information, diagnosis information and others.

In FIG. 7B the system 200 includes a diagnostic stage, where a diagnosis is performed by a physician and the diagnosis information and other information obtained relating to the patient are input to a user interface. This diagnosis stage 202 allows a provider to evaluate a patient and input information electronically. Once input, the system may automatically process the diagnosis information to generate treatment options that are pre-filtered in accordance with evidence-based medicine procedures and payer plan language. Thus, the system uses computer logic to interpret or identify the specific treatment options that a payer will pay for or otherwise settle when presented. Once identified, the provider can select from this filtered set of options using menus, list, buttons, etc. displayed as part of the interface.

With respect to the system 200, in one embodiment, the initial input is diagnosis information. This is in contrast to some of the embodiments discussed above wherein the first input is a treatment plan which will be subsequently reviewed for errors and compliance issues. Thus, the system 200 receives a diagnosis using a graphic user interface or GUI. Next, the system 200 uses the diagnosis and stored plan language 203 to filter a knowledge base (see FIG. 1B) to generate a set of options that meets both the plan language and the evidence-base medicine guidelines. This filtering results in a set of treatment options which can be selected at the option review or selection stage 206.

With the diagnosis information of the patient stored in the applicable database and the option filtering complete, a provider selects treatment plan options 206 and provides certain variable patient-specific treatment information (e.g., drug dosage ranges, drugs, procedures, etc.). In one embodiment, a single search or query is performed relative to a local or remote database that includes patient diagnosis information, evidence-based medicine guidelines, and optionally, other patient data.

In step 206 a treatment plan is selected using evidence-based medicine and a plan language filter. Plan language from the payer is considered relative to evidence-based medicine guidelines in light of the diagnosis information which is specific to a medical condition to generate a set of treatment options which a medical provider can select from. The treatment options with respect to which the medical provider can select are constrained such as they comply with the medical condition at issue, the evidence-based medicine guidelines as well as payer plan language portions. Non-limiting examples of payer plan language portions include a definition of medical necessity, a definition of experimental/investigational medicine, and a definition of unproven medical treatment, which are discussed in more detail below.

The term medical necessity relates to medical interventions that are truly necessary and therefore will likely be reimbursed by the payer. The boundaries are typically set using levels of medical evidence, endorsement by national governmental agencies/consensus groups, medical literature, databases of ongoing medical trials, and current medical practice, and the like. Examples of medical necessities include: services, drugs, supplies or equipment provided by a hospital or covered provider of the health care services that the plan determines are appropriate to diagnose or treat the patient's condition, illness or injury; are consistent with standards of good medical practice in the United States; are not primarily for the personal comfort or convenience of the patient, the family, or the provider; are not a part of or associated with the scholastic education or vocational training of the patient; and in the case of inpatient care, cannot be provided safely on an outpatient basis. The fact that a covered provider has prescribed, recommended, or approved a service, supply, drug or equipment does not, in itself, make it medically necessary.

The term experimental/investigational medicine relates to medical interventions that are not standard of care but are under study or require further study to truly be considered standard of care. The boundaries are typically set using levels of medical evidence, endorsement by national governmental agencies/consensus groups, medical literature, databases of ongoing medical trials, and current medical practice and the like. Examples of experimental or investigational medicine include: a drug, device, or biological product is experimental or investigational if the drug, device, or biological product cannot be lawfully marketed without approval of the U.S. Food and Drug Administration (FDA) and approval for marketing has not been given at the time it is furnished. Approval means all forms of acceptance by the FDA. A medical treatment or procedure, or a drug, device, or biological product is experimental or investigational if: 1) reliable evidence shows that it is the subject of ongoing phase I, II, or III clinical trials or under study to determine its maximum tolerated dose, its toxicity, its safety, its efficacy, or its efficacy as compared with the standard means of treatment or diagnosis; or 2) reliable evidence shows that the consensus of opinion among experts regarding the drug, device, or biological product or medical treatment or procedure is that further studies or clinical trials are necessary to determine its maximum tolerated dose, its toxicity, its safety, its efficacy, or its efficacy as compared with the standard means of treatment or diagnosis. Reliable evidence means published reports and articles in the authoritative medical and scientific literature; the written protocol or protocols used by the treating facility or the protocol(s) of another facility studying substantially the same drug, device, or medical treatment or procedure; or the written informed consent used by the treating facility or by another facility studying substantially the same drug, device, or medical treatment or procedure. Determination of experimental/investigational status may require review of appropriate government publications such as those of the National Institute of Health, National Cancer Institute, Agency for Health Care Policy and Research, Food and Drug Administration, and National Library of Medicine. Independent evaluation and opinion by Board Certified Physicians who are professors, associate professors, or assistant professors of medicine at recognized United States Medical Schools may be obtained for their expertise in subspecialty areas.

The term unproven medical treatment relates to those treatments that are not supported by medical evidence (endorsement by national governmental agencies/consensus groups, medical literature, databases of ongoing medical trials, and the like) to a degree required by a certain payer to justify reimbursement. Examples of unproven medical treatments include any medical procedure or drug that does not have scientific evidence that permits conclusions as to its effects on health outcomes. Scientific evidence is evidence that is obtained from well designed and soundly conducted studies. Such studies must have been published in peer-reviewed journals. The study must show a measurable effect on health outcomes that can be duplicated outside of the study's setting. Decisions to cover or exclude a treatment will be based on the conclusions of prevailing medical research. Further examples include: the use of a drug, substance or device that has not been approved by the US FDA, or which has been conditionally approved for limited diagnosis or treatment of conditions other than those for which a covered individual is receiving service, supply or treatment (off label or unlabeled use), or which has not been designated as efficacious by NCCN or NIH guidelines.

As an example, if a patient has been diagnosed with a renal condition or a cancer condition, the evidence-based guidelines would be constrained, based on the condition, and the payer plan language would be filtered relative to that. As a result, the treatment options, which are represented to the provider in the form of dropdown menus or fillable forms would be constrained relative to that guidance. In addition, if a drug is a treatment option the range of dosage units would be selectable, for example, from A mg to Z mg such that the range is established based on evidence based medicine guidelines from a knowledge base.

In addition, when a provider inputs a diagnosis and later starts choosing treatments, any treatment selection is a further input that results in changes to the options and choices which are subsequently displayed using the interface. Thus, if the diagnosis is for a type of cancer, and the first treatment option is for chemotherapy, the logic of the overall system may next present treatment options relating to drugs that reduce side effects or other evidence based medicine treatment options that logically follow based on prior provider selections. In addition, the provider has the opportunity to deviate from the treatment options presented. Prior to discussing the deviation from automated treatment plan generation, it is useful to consider the steps which follow plan acceptance. In one instance, the payer is part of the group which includes insurers, third party payment providers, employers, and governmental entities.

While answering questions and inputting treatment options, selecting the treatment options, and entering variable treatment information, all choices comply with evidence-based guidelines. The medical provider has the opportunity to approve the overall plan, in which case a code is issued 210, which is a plan code. In step 210, a treatment plan is issued in one embodiment. Following the issuance of a treatment plan, in one embodiment, an e-mail is sent to the provider step 216 indicating that a treatment code has been issued and also the treatment plan is sent to the payer. Once the treatment plan code has been generated for a patient that code can be used to settle certain costs associated with the plan. In one embodiment, a settlement 220 occurs when a plan code is presented to a payer such that some or all of the costs of the plan for a particular patient are paid. As used herein, the term "settlement" refers to the exchange of financial consideration, information, or other considerations to compensate a party for services or materials.

Alternatively, in another embodiment, the medical provider has the option to opt out of the pre-populated, pre-constrained treatment options of stage 206 and decide to deviate from the automated treatment plan generation process. If the provider deviates from the plan, a manual or automated review of the proposed treatment plan language occurs 224. There can be an automatic or manual evaluation of whether or not the deviation from the plan complies with evidence-based medicine guidelines. The plan review embodiments discussed above with respect to FIGS. 1 and 1B can be used. In one embodiment, a database of expected deviations is provided, such that the deviations identified also comply with evidence-based medicine guidelines and can be further indexed to indicate whether they comply with payer guidelines.

If the proposed deviation is not justified, the next step is for a task code to be generated 228. In one embodiment, a task code refers to a notice to a third party or other system user such as a medical office staff member notifying them that a manual treatment plan review is needed. Essentially, this part of the process indicates that further review of the proposed deviation is necessary. Following that, the review of the treatment plan option and plan language occur in Step 232 by a third party service provider. Next, a decision is made as to whether the deviation from the treatment plan options can be modified to comply with evidence-based medicine or the payer plan language. If it is properly modified, a treatment plan code is issued 210. However, if the deviation is unacceptable and cannot be reconciled with evidence-based medicine, the treatment deviation is referred to the payer for review 240.

Figure 8A:
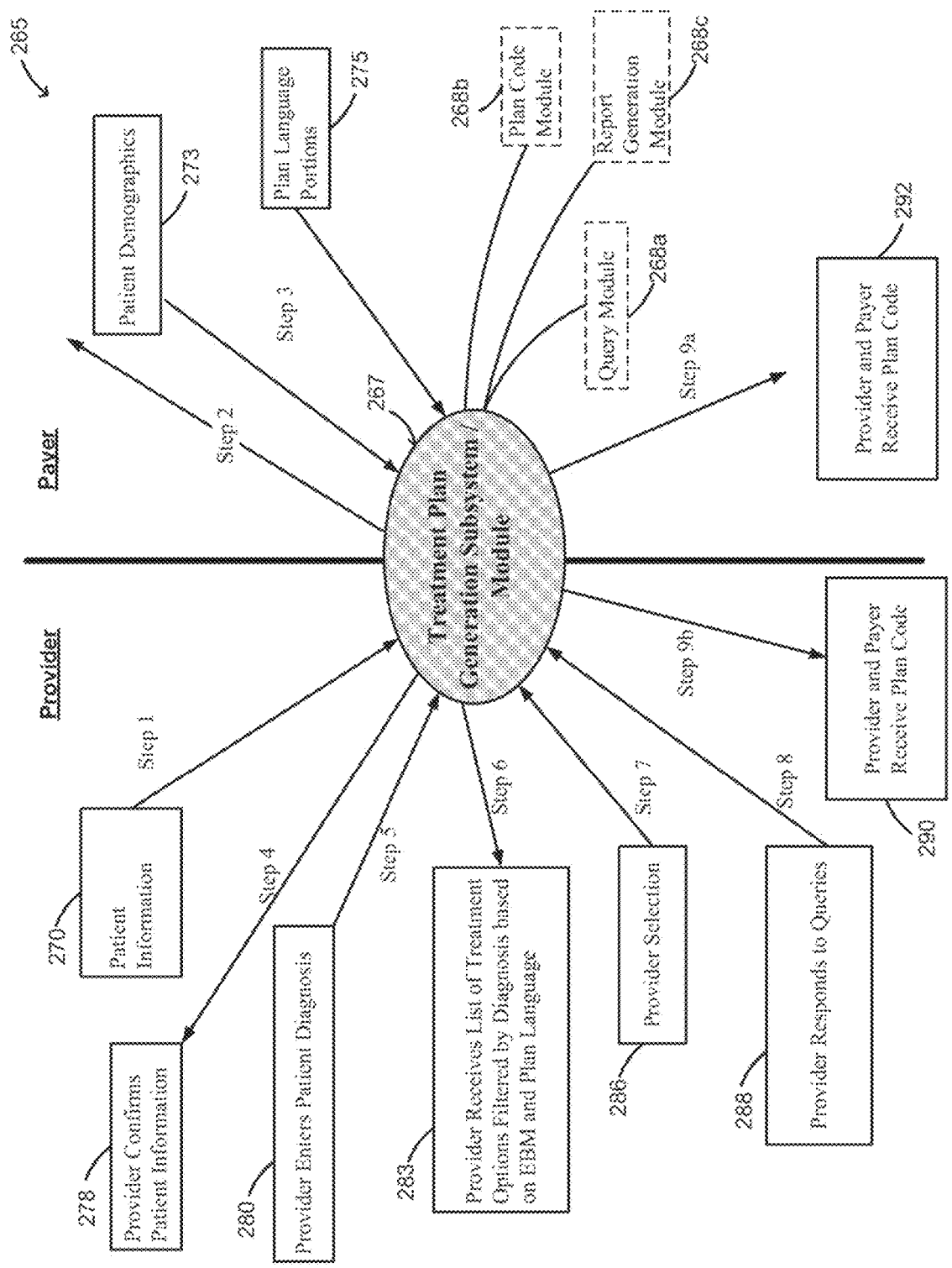
FIG. 8A is a schematic diagram of a treatment plan generation subsystem or module with various payer and provider inputs and outputs, in accordance with an embodiment of the invention.

FIG. 8A shows a schematic diagram that depicts an overall system 265 that includes a treatment plan generation subsystem/module 267. As used herein, the treatment plan generation module/subsystem 267 refers to one or more software modules or computer-based logical subsystems suitable for generating a treatment plan. Thus, the processor embodiment executing certain instructions shown in FIG. 7A is one example of such a subsystem. Alternatively, a particular software application (or multiple applications) running on the processor can also be an example of the module 267. The treatment plan generation module 267 can be used to receive inputs from (and transmit data to) two sides of the system, the provider side and the payer side. The provider side is shown on the left portion of FIG. 8A and the payer side is shown on the right side of FIG. 8A.

In addition, various software modules such as a query module 268a, a plan code module 268b, and a report generation module 268c can also be used in the system either as stand alone modules or as part of the treatment plan module/subsystem 267. These modules and others not shown in the figure provide features that streamline a medical provider's day to day diagnosis, reporting and treatment plan creation by providing a sequence of automated stages of data processing that are efficient and intuitive.

Initially, in Step 1, patient information 270 such as a patient name or patient identifier is input into the overall treatment plan generation module 267 to begin the process for generating a treatment plan. Next, in Step 2, an information request is relayed to the payer to verify the patient information input by the provider. In Step 2, the patient's demographic information 273 that was requested is relayed to the treatment plan generation module 267. In one embodiment, the demographic information 273 includes payer census data that is automatically queried to determine patient eligibility when a provider enters the patient's name using the interface. In Step 3, plan language portions 275 are transmitted to the treatment plan generation module 267. The requests and transmissions are typically performed using a client server environment using one of the GUI's described herein.

In these steps, the payer verifies the eligibility of the patient. If the eligibility is valid, the patient is located in the database and the payer returns the patient's demographics and the payer language to the subsystem 267. In one embodiment, the user interface displays certain parts of the patient's insurance plan/payer plan for the provider to review. Co-pays, patient information, patient demographics, prior treatments, and prior plans can all be displayed to providers as reports created using a report generation module 268c.

In Step 4, the provider confirms the patient information 278. The patient information is relayed to the provider through a browser or other graphic user interface in response to the information transmitted by the payer to the treatment plan subsystem 267. Next, the provider enters the patient diagnosis 280 at Step 5. Further, with respect to Step 6, the provider receives a list of treatment options 283 specific to a diagnosis and filtered based upon evidence-based medicine guidelines and payer plan language. In Step 7, the provider makes a selection of one or more of the treatment options 286. Any selected options are transmitted to the treatment plan module. In addition to the option of selecting from the treatment options displayed using the interface, the provider has the parallel option to opt out of the proposed treatment plan options and enter options that deviated from those presented. In one embodiment, this opt out decision is handled using the process flow of FIG. 1 starting at input 14.

With respect to FIG. 8A, in Step 8 the provider responds to various queries as part of an automated wizard 288 that proposes questions that change based on the prior answers to complete the data collection process such that a treatment plan is generated with all of the requisite details relating to dosage level, drugs, therapies, procedures, etc. Next, the treatment plan module can issue a plan code to one or both of the payer 290 and the provider 292. In Step 9a, the provider and payer receive a plan code and in Step 9b, the provider and payer receive a plan code. These steps can occur together, separately, or result in the code only being sent to one of the provider or payer in one embodiment. As discussed above, the plan code can be used as token or consideration that when presented to a payer results in the settlement of some or all of the costs associated with the treatment plan linked to the respective plan code.

As discussed above, various software modules such as a query module 268a, a plan code module 268b, and a report generation module 268c perform various functions in the overall system. For example, in one embodiment the query module 268a receives information from the payer or provider and queries databases with information for creating the treatment plans. The plan code module 268b can perform multiple functions such as generating a plan code for both a payer and a provider and processing a plan code when it is sent to a payer for settlement. In turn, the report generation module 268c can generate any suitable reports, alerts, or information displays of interest such as checklists for users entering data using the interface.

Figure 8B:
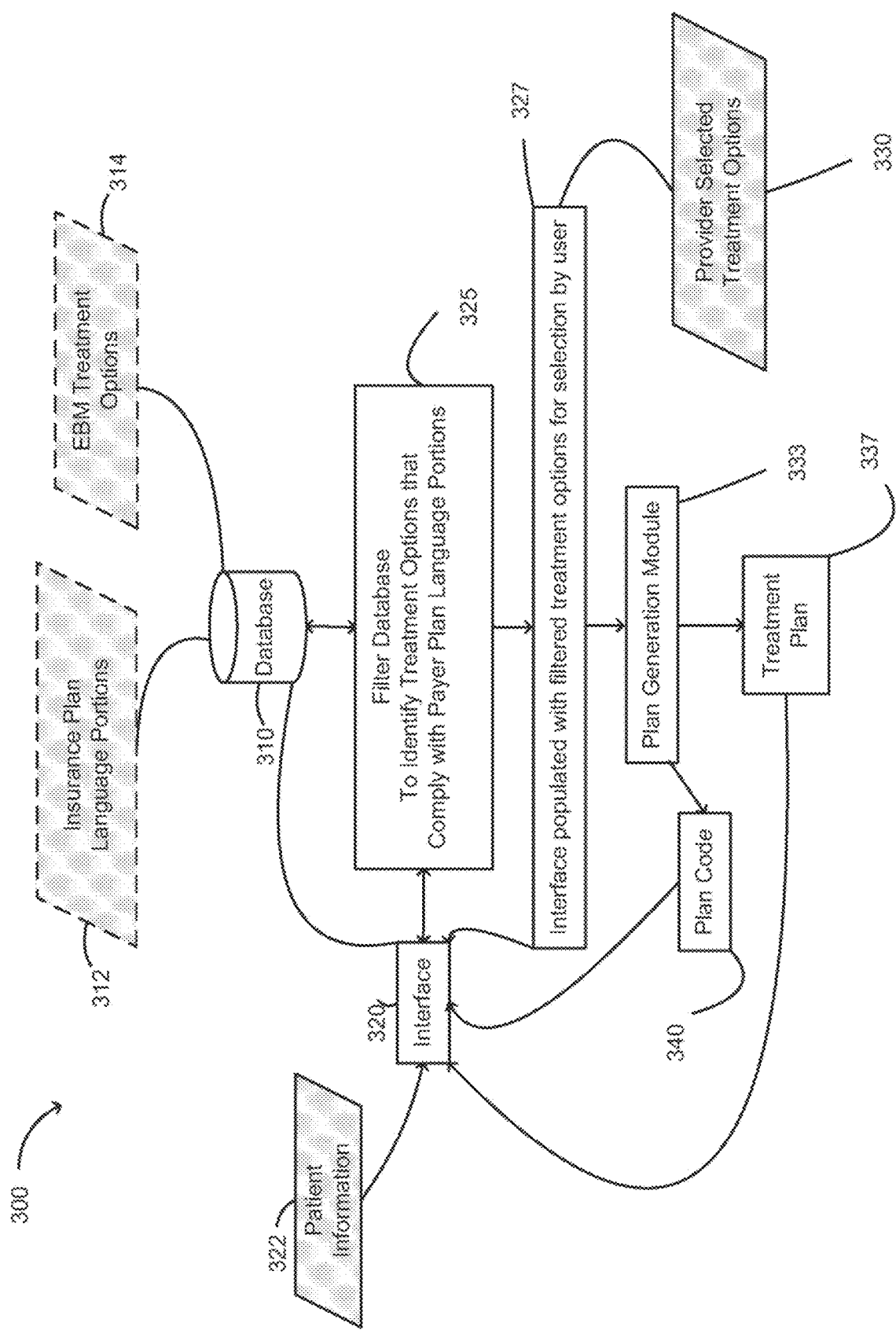
FIG. 8B is a schematic diagram of an exemplary system with various operational phases for transforming a patient diagnosis into a treatment plan, in accordance with an embodiment of the invention.

FIG. 8B shows an overall system 300 that provides additional details of a specific embodiment of user interface-based system for collecting information and transforming it into a treatment plan. The system 300 includes a database 310 which can include one or more of plan language portions 312 and a plurality of evidence-based medicine accepted treatment options 314. An interface 320, which is typically implemented using a browser is accessible by a provider (and payer), such as a doctor or nurse or other end user, and is used to collect information and display it. The interface 320 receives patient information 322 from the provider and/or the payer. Thus, patient demographic information may be indexed by the payer and sent to the browser in response to an identifier or code associated with the patient.

In turn, the different types of patient information 322 are relayed to a computer which can be either locally based with the medical provider or remotely located. The computer queries the database 310, which may be one or more databases, using a query module or other software applicable to filter the database. Following this filtering stage 325, treatment options that comply with payer plan language and evidence-based medicine guidelines are identified. These options are also constrained in response to the diagnosis information or other patient information 322 provided via the interface or from the payer.

In the next stage 327, the user interface 320 is populated with user selectable treatment options that result from the filtering of the database 310 to identify evidence-based medicine treatment options that are consistent with payer plan language portions. The provider selects the various treatment options 330 and those treatment options can be relayed to the plan generation module 333 which is stored locally or on a remote server. In one embodiment, the plan generation module tracks the filtered provider selected treatment options 330 as well as any manual inputs (dosages, procedures, etc.) input by the provider. Typically, an automated wizard with various types of logical tiered questions and inputs is used to expedite selection of appropriate treatment plan options from the interface.

Next, a treatment plan is generated by the plan generation module 333. In some embodiments, this module 333 also generates a plan code 340. As a result, a treatment plan 337 and a plan code 340 can be generated. An email can be sent by the system to confirm the completion of the process or an alert window integrated with the user interface 320 can inform the provider of the plan code. An alert can also be generated indicating that the plan code 340 has been sent to the payer. This process can be opted out of according to the secondary process flow described with respect to FIG. 7B.

With the various process flows, stages, and different system embodiments discussed above, it is also useful to consider some exemplary non-limiting embodiments of various user interface screens and other features of the invention. FIGS. 9A to 9M depict various exemplary interfaces corresponding to different steps and provider system interactions from the process flows discussed above.

Figure 9A:
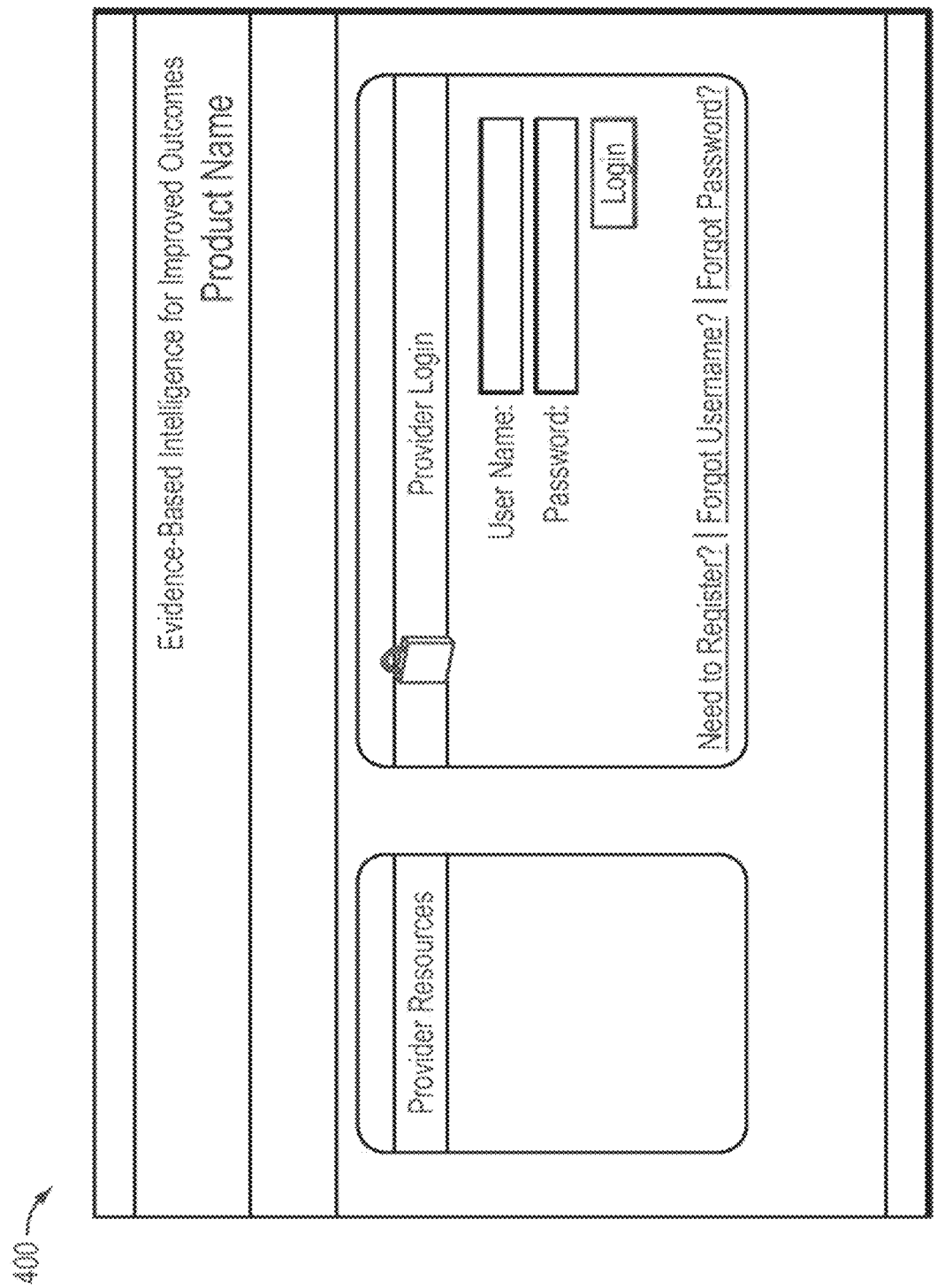

FIG. 9A shows an exemplary user interface 400 for logging in and accessing a data collection and treatment plan generation system with a username and secure password. This interface allows a provider or other user to query one or more databases and generate evidence-based medicine treatment options for a payer plan compliant treatment plan. The system or subsystem used to generate treatment plans is generically identified as "Product Name." An interface window for listing various provider resources is shown to the left while a provider login screen is shown to the right. In one embodiment, providers access the user interface to facilitate and streamline treatment plan creation in their respective practices.

FIG. 9B shows an exemplary user interface 420 that shows the selection of patient information as the active screen. This high level interface view also indicates that diagnosis and treatment interface screens are available under other selectable tabs. As shown, various basic patient identifiers can be collected for validation by the payer and for other uses. In one embodiment, the systems and methods that use the interface 420 to exchange data between a payer and a provider will automatically provide the insurance name, group number, or policy number (or other payer information of interest) after the system confirms with a payer system that the patient is eligible.

Figure 9C:
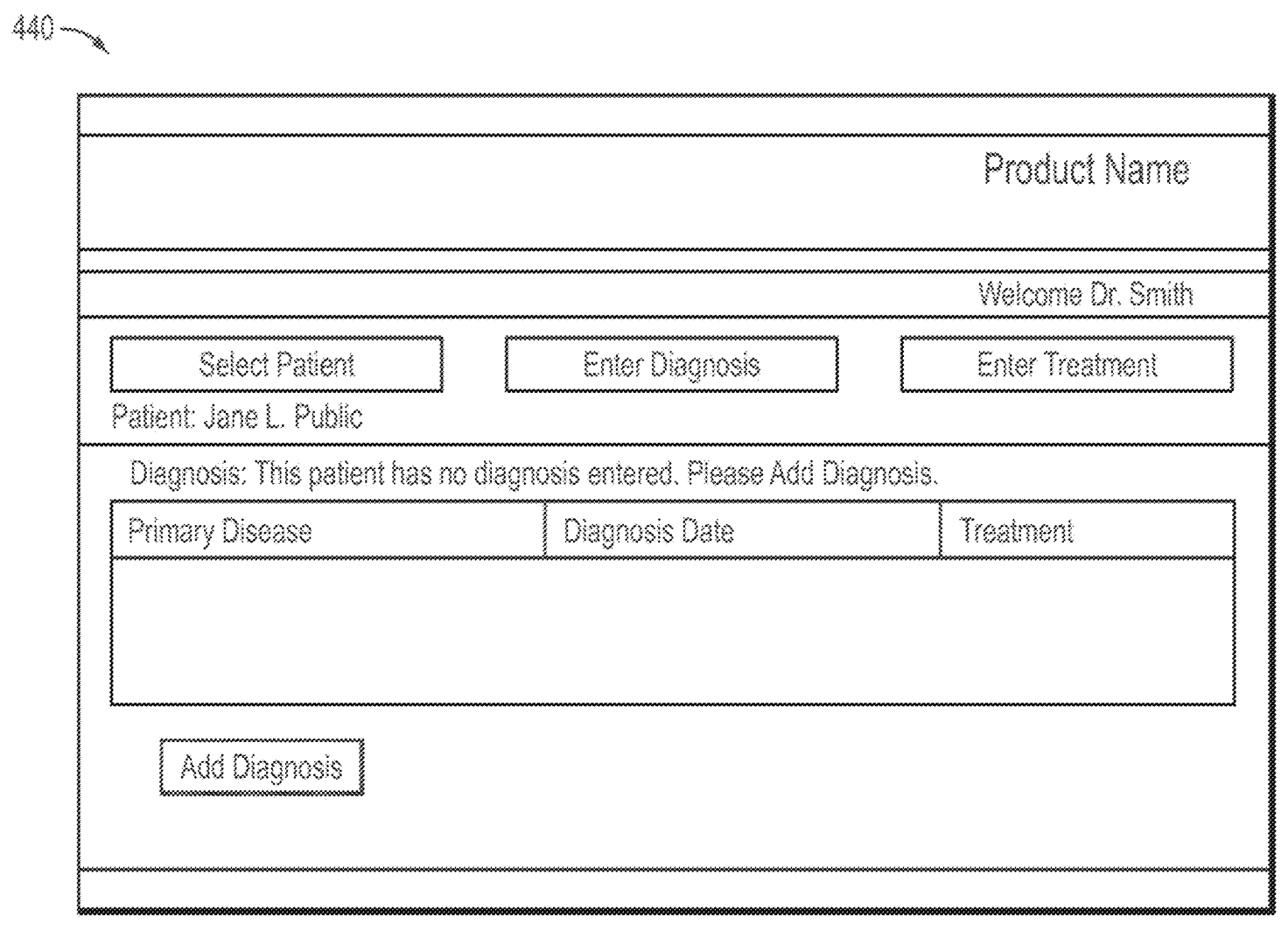

FIG. 9C shows an exemplary user interface 440 in which the patient has been selected. However, no diagnosis information has been provided. At this stage in the process the diagnosis needs to be entered. This diagnosis information will be relayed to the plan generation modules and related software to provide treatment options which can be used to generate a treatment plan.

Figure 9D:
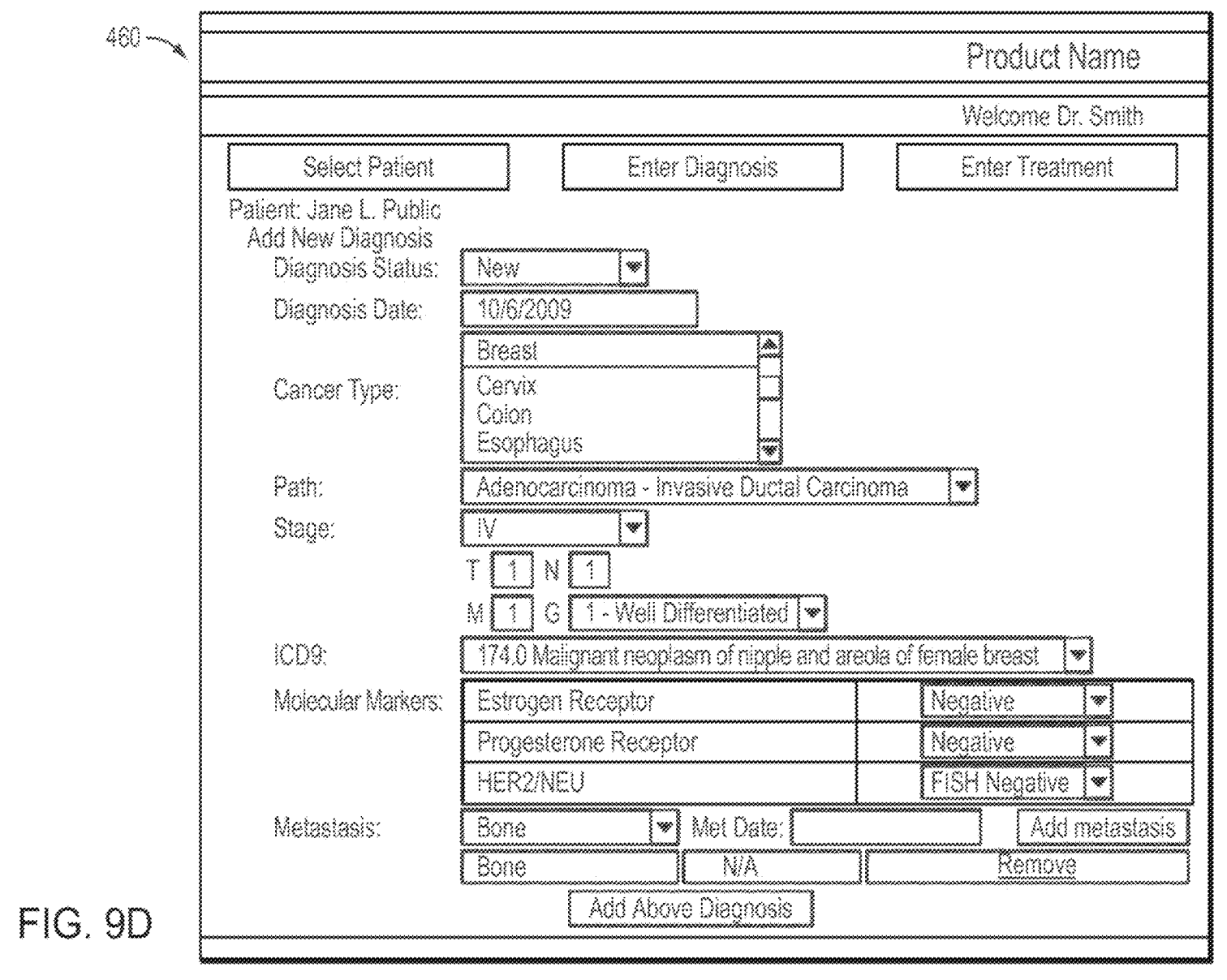
Figure 9E:
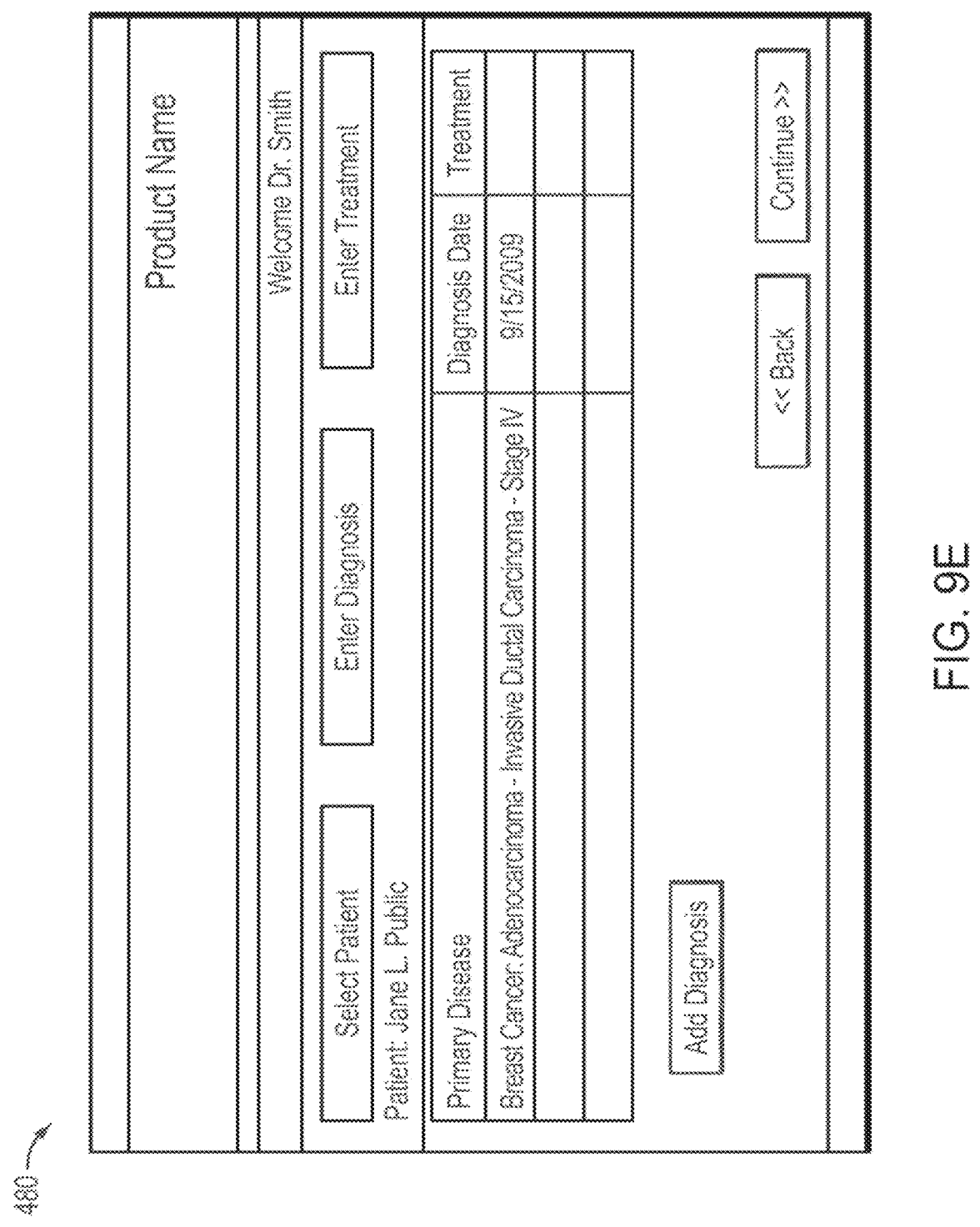

FIG. 9D shows an exemplary user interface 460 of the user interface in which diagnosis information including diagnosis status, diagnosis date, cancer-type path, stage, ICD9 code, molecular markers and the nature of any metastasis are displayed. In turn, FIG. 9E shows an exemplary user interface 480 that shows a patient that has been enrolled in the system. In addition, as shown in FIG. 9D, certain diagnosis information has been collected and stored in a database using the user interface 460.

FIG. 9F shows an exemplary user interface 500 in which a treatment plan option wizard is about to begin. As shown, various treatment options have been selected from a drop-down list. This list is pre-populated based on the filtering of the database based on the payer plan language and evidence-based guidelines. This interface screen 500 shows the selection of treatment plan options. Since a wizard is used in one embodiment, one choice of options triggers various other downstream treatment options for consideration by the provider.

FIG. 9G shows an interface 520 with additional treatment plan options. In this embodiment, a variable treatment option in the form of a dosage limit is being specified for the drug Paclitaxel. As shown, in light of the evidence based guidelines in the knowledge base, the dosage range is limited from 234 mg/m2 to 286 mg/m2. However, a provider could opt out of these choices and seek approval for the deviation as discussed above. In turn, FIG. 9H shows an interface 540 indicating additional information for a treatment option 540 with constraints associated with a drug identified as a candidate treatment option. In FIG. 9H the provider is outside the allowed range permitted by the system. However, in FIG. 9I in the interface screen 560 shown, the user has elected to return to allowed range and not opt out.

FIG. 9J shows an interface 580 that demonstrates the drop down menu function that can be used with a wizard to select treatment options. In the example shown, the provider is informed of the low emetogenecity of the proposed regimen and given the choice to supplement with another drug. An interface screen 600 showing additional supportive drugs which can be selected as part of a treatment plan is shown in FIG. 9K. FIG. 9L shows an interface 620 that includes the treatment plan describing various treatment options that have been selected based on the prior comments in the wizard. In turn, FIG. 9M shows a user interface 640 that displays a plan code which has been generated after the selection of treatment plan options. These various screenshot and interfaces provide further detail relative to the other embodiments discussed herein.

Non-Limiting Software Features for Implementing Embodiments of the Invention

It will be apparent to one of ordinary skill in the art that some of the embodiments as described hereinabove may be implemented in many different embodiments of software, firmware, and hardware in the entities illustrated in the figures. The actual software code or specialized control hardware used to implement some of the present embodiments is not limiting of the invention.

The computer and software based embodiments described herein and claimed transform specific classes of data corresponding to real world information (such as symptoms, patient data, treatment plans, drug information, treatment best practices, insurance data, and other types of data) and otherwise modify that data to generate output data and reports as part of a computer-based tool to aid the insurance, financial, and medical industries.

Moreover, the processes associated with some of the present embodiments may be executed by programmable equipment, such as computers. Software that may cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable medium later. Such a medium may include any of the forms listed above with respect to storage devices and may further include, for example, a carrier wave modulated, or otherwise manipulated, to convey instructions that can be read, demodulated/decoded and executed by a computer.

Software of the server and other modules herein may be implemented in various languages, such as, for example, ColdFusion, Ruby on Rails, ASP, ASP.NET, SQL, PL-SQL, T-SQL, DTS, HTML, DHTML, XML, ADO, Oracle database technology, JavaScript, JSP, Java, Flash, Flex, and C #. In addition, software at the application server may be added or updated to support additional device platforms.

A "computer" or "computer system" may be, for example, a wireless or wireline variety of a microcomputer, minicomputer, laptop, personal data assistant (PDA), wireless e-mail device (e.g., BlackBerry), cellular phone, a smartphone, a mobile device, pager, processor, or any other programmable device, which devices may be capable of configuration for transmitting and receiving data over a network. Computer devices disclosed herein can include data buses, as well as memory for storing certain software applications used in obtaining, processing and communicating data. It can be appreciated that such memory can be internal or external. The memory can also include any means for storing software, including a hard disk, an optical disk, floppy disk, ROM (read only memory), RAM (random access memory), PROM (programmable ROM), EEPROM (electrically erasable PROM), and other computer-readable media.

In some embodiments, the data processing device may implement the functionality of the methods of the invention as software on a general purpose computer. In addition, such a program may set aside portions of a computer's random access memory to provide control logic for operating a rules engine or other software modules. In such an embodiment, the program is written in any one of a number of high-level languages, such as FORTRAN, PASCAL, DELPHI, C, C++, C #, VB.NET, or BASIC. Furthermore, in various embodiments the program is written in a script, macro, or functionality embedded in commercially available software, such as VISUAL BASIC. Additionally, the software in one embodiment is implemented in an assembly language directed to a microprocessor resident on a computer. The software may be embedded on an article of manufacture including, but not limited to, "computer-readable program means" such as a floppy disk, a hard disk, a downloadable file, an optical disk, a magnetic tape, a PROM, an EPROM, or CD-ROM.

Various examples of suitable processing modules are discussed below in more detail. Notwithstanding other definitions used herein, a module can also refer to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as patient information, payer plan, language, treatment regimen, treatment options, evidence-based medicine guidelines, and other information of interest described herein.

In a typical embodiment of the present invention, some or all of the processing of the diagnosis and treatment data collected using the interface along with the processor-based system is implemented as a set of computer program instructions that is converted into a computer executable form, stored as such in a computer readable medium, and executed by a microprocessor under the control of an operating system. Thus, query, response, and input data are transformed into processor understandable instructions suitable for generating a database of patient information, diagnosis information, and payer plan language, and otherwise detecting or displaying any of the foregoing and all of the other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

While the invention has been described in terms of certain exemplary preferred embodiments, it will be readily understood and appreciated by one of ordinary skill in the art that it is not so limited and that many additions, deletions and modifications to the preferred embodiments may be made within the scope of the invention as hereinafter claimed. Accordingly, the scope of the invention is limited only by the scope of the appended claims.

It should be understood that the above-described embodiments and the following examples are given by way of illustration, not limitation. Various changes and modifications within the scope of the present invention will become apparent to those skilled in the art from the present description.

What is claimed is:

1. A system configured to compare a treatment plan with evidence-based medicine criteria to determine if a treatment of a patient's medical condition adheres to best practices, the system comprising:

at least one computing device having at least one computer processor configured to execute software instructions;

a memory interconnected to said computer processor for storing software instructions; and wherein said processor executes steps comprising:

determining a diagnosis for a patient based upon, at least in part, a condition associated with a plurality of diagnosis possibilities for the patient and a treatment plan;

storing, at the one or more computing devices, a set of anticipated treatment plans associated with each of the plurality of diagnosis possibilities, at least a portion of the anticipated treatment plans deviating from the evidence-based medicine criteria;

receiving a configuration at the one or more computing devices, the configuration indicating which of a plurality of analyzer rules to run, each of the plurality of analyzer rules including a parameter list specifying input data of the rule and a list of one or more flags, wherein each of the one or more flags includes customizable flag text for describing a violation of the evidenced-based medicine criteria, a pre-defined error code associated with the violation, an identification of target data in the treatment plan, and an identification of reference data in the evidence-based medicine criteria to which the target data is compared to determine whether the violation has occurred;

displaying a user interface for customizing the customizable flag text of the one or more flags of each of the plurality of analyzer rules, the user interface allowing customization of the customizable flag text after compilation;

running two or more of the plurality of analyzer rules in parallel based upon the configuration, the two or more analyzer rules being run at the one or more computing devices without first receiving a selection of the determined diagnosis, at least one of the two or more analyzer rules including a flag whose pre-defined error code is associated with a violation of a dose associated with the treatment plan for the determined diagnosis;

for each of the two or more analyzer rules, transferring to a master flag list the flags whose error codes are associated with violations occurring during said running of the two or more analyzer rules; and displaying the customizable flag text of each flag in the master flag list.

2. The system of claim 1, wherein the steps performed by the processor further comprise:

receiving, at the one or more computing devices, a corrected candidate treatment and regimen.

3. The system of claim 2, wherein the steps performed by the processor further comprise:

generating an evidence-based medicine treatment plan using the one or more computing devices, for the patient, consistent with payment guidelines of a payer in response to receiving the corrected candidate treatment and regimen; and generating a treatment plan code, using the one or more computing devices, the treatment plan code associated with the evidence-based medicine treatment plan generated for the patient, wherein the treatment plan code is unique and specific to the patient and the evidence-based medicine treatment plan.

4. The system of claim 1, wherein at least one of the two or more analyzer rules includes a flag whose pre-defined error code is associated with a violation of at least one of a treatment cycle, drug, or drug group associated with the evidence-based medicine criteria.

5. The system of claim 1, wherein the computer processor is further configured to:

store, at the one or more computing devices, data representative of parameters tied to a patient associated with the running of analyzer rules, and a number of flags generated.

6. The system of claim 1, wherein the computer processor is further configured to analyze data related to the evidence-based medicine criteria.

7. The system of claim 1, wherein the computer processor is further configured to analyze, at the one or more computing devices, one or more properties of the treatment plan for the determined diagnosis.

8. The system of claim 1, wherein the computer processor is further configured to analyze, at the one or more computing devices, one or more drugs or drug groups associated with the treatment plan for the determined diagnosis.

9. The system of claim 1, wherein the steps performed by the processor further comprise displaying, at the one or more computing devices, one or more outputs selected from the group consisting of: exposure estimates, risks and prognosis, cost savings opportunities, and actionable information/interventions.

10. The system of claim 1, wherein at least one of the two or more analyzer rules includes a flag whose pre-defined error code is associated with a violation of identified insurance policy language, and the steps performed by the processor further comprise transmitting the identified language to an insurer.

11. The system of claim 1, wherein the steps performed by the processor further comprise identifying, at the one or more computing devices, a costs savings opportunity in relation to the treatment plan, the costs savings opportunity including either one or both of a less expensive supplier of a medication and data for negotiating a cost savings with a medical good or drug supplier.

12. The system of claim 1, wherein the steps performed by the processor further comprise reporting cost avoidance data associated with the treatment plan.

13. The system of claim 1, wherein the one or more computing devices includes a common framework API, a clinical API, and a user, payer, patient, and provider API.

14. The system of claim 1, wherein the steps performed by the processor further comprise:

receiving, at the one or more computing devices, a selection of the condition associated with the plurality of diagnosis possibilities for the patient;

determining, at the one or more computing devices, one or more candidate regimens based upon, at least in part, the condition associated with the plurality of diagnosis possibilities for the patient, each of the one or more candidate regimens associated with a plurality of candidate treatment options;

comparing the candidate treatment options associated with the one or more candidate regimens and generating a consolidated list of candidate treatment options in which identical candidate treatment options among the plurality of candidate treatment options are merged to appear only once;

displaying, at the one or more computing devices, the consolidated list of candidate treatment options; and receiving, at the one or more computing devices, a selection of the treatment plan from the consolidated list of candidate treatment options displayed.

15. The system of claim 1, wherein the configuration further indicates in which order to run the two or more analyzer rules, and said running of the two or more analyzer rules includes running the two or more analyzer rules in an order based upon the configuration.

16. The system of claim 1, wherein the steps executed by the processor further comprise gathering performance metrics on the two or more analyzer rules.

17. The system of claim 1, wherein the steps executed by the processor further comprise storing an analyzer run including data representative of the configuration and results of said running of the two or more analyzer rules.

18. The system of claim 17, wherein the stored analyzer run includes the flags whose error codes are associated with violations occurring during said running of the two or more analyzer rules.

19. A method of comparing a treatment plan with evidence-based medicine criteria to determine if a treatment of a patient's medical condition adheres to best practices, the method comprising:
- determining a diagnosis for a patient based upon, at least in part, a condition associated with a plurality of diagnosis possibilities for the patient and a treatment plan;
- storing, at one or more computing devices, a set of anticipated treatment plans associated with each of the plurality of diagnosis possibilities, at least a portion of the anticipated treatment plans deviating from the evidence-based medicine criteria;
- receiving a configuration at the one or more computing devices, the configuration indicating which of a plurality of analyzer rules to run, each of the plurality of analyzer rules including a parameter list specifying input data of the rule and a list of one or more flags, wherein each of the one or more flags includes customizable flag text for describing a violation of the evidenced-based medicine criteria, a pre-defined error code associated with the violation, an identification of target data in the treatment plan, and an identification of reference data in the evidence-based medicine criteria to which the target data is compared to determine whether the violation has occurred;
- displaying a user interface for customizing the customizable flag text of the one or more flags of each of the plurality of analyzer rules, the user interface allowing customization of the customizable flag text after compilation;
- running two or more of the plurality of analyzer rules in parallel based upon the configuration, the two or more analyzer rules being run at the one or more computing devices without first receiving a selection of the determined diagnosis, at least one of the two or more analyzer rules including a flag whose pre-defined error code is associated with a violation of a dose associated with the treatment plan for the determined diagnosis;
- for each of the two or more analyzer rules, transferring to a master flag list the flags whose error codes are associated with violations occurring during said running of the two or more analyzer rules; and
- displaying the customizable flag text of each flag in the master flag list.

20. A non-transitory computer-readable medium on which are stored instructions executable by a processor or programmable circuit to perform operations for comparing a treatment plan with evidence-based medicine criteria to determine if a treatment of a patient's medical condition adheres to best practices, the operations comprising:
- determining a diagnosis for a patient based upon, at least in part, a condition associated with a plurality of diagnosis possibilities for the patient and a treatment plan;
- storing, at one or more computing devices, a set of anticipated treatment plans associated with each of the plurality of diagnosis possibilities, at least a portion of the anticipated treatment plans deviating from the evidence-based medicine criteria;
- receiving a configuration at the one or more computing devices, the configuration indicating which of a plurality of analyzer rules to run, each of the plurality of analyzer rules including a parameter list specifying input data of the rule and a list of one or more flags, wherein each of the one or more flags includes customizable flag text for describing a violation of the evidenced-based medicine criteria, a pre-defined error code associated with the violation, an identification of target data in the treatment plan, and an identification of reference data in the evidence-based medicine criteria to which the target data is compared to determine whether the violation has occurred;
- displaying a user interface for customizing the customizable flag text of the one or more flags of each of the plurality of analyzer rules, the user interface allowing customization of the customizable flag text after compilation;
- running two or more of the plurality of analyzer rules in parallel based upon the configuration, the two or more analyzer rules being run at the one or more computing devices without first receiving a selection of the determined diagnosis, at least one of the two or more analyzer rules including a flag whose pre-defined error code is associated with a violation of a dose associated with the treatment plan for the determined diagnosis;
- for each of the two or more analyzer rules, transferring to a master flag list the flags whose error codes are associated with violations occurring during said running of the two or more analyzer rules; and
- displaying the customizable flag text of each flag in the master flag list.

\* \* \* \* \*